United States Patent
Langer et al.

(10) Patent No.: US 11,850,034 B2
(45) Date of Patent: Dec. 26, 2023

(54) GASTRORETENTIVE ARTICLES FOR ALCOHOL SENSING

(71) Applicants: Massachusetts Institute of Technology, Cambridge, MA (US); The Brigham and Women's Hospital, Inc., Boston, MA (US); The General Hospital Corporation, Boston, MA (US)

(72) Inventors: Robert S. Langer, Newton, MA (US); Carlo Giovanni Traverso, Newton, MA (US); Malvika Verma, Cambridge, MA (US); Feyisope Eweje, Jacksonville, NC (US); Christoph Winfried Johannes Steiger, Cambridge, MA (US); Junwei Li, Cambridge, MA (US); Nhi Phan, Somerville, MA (US); Hen-Wei Huang, Cambridge, MA (US); Jacqueline Chu, Boston, MA (US); John Ashraf Fou Salama, Cambridge, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 219 days.

(21) Appl. No.: 17/318,040

(22) Filed: May 12, 2021

(65) Prior Publication Data

US 2021/0353174 A1   Nov. 18, 2021

Related U.S. Application Data

(60) Provisional application No. 63/023,280, filed on May 12, 2020.

(51) Int. Cl.
  *A61B 5/07* (2006.01)
  *A61B 5/00* (2006.01)

(52) U.S. Cl.
  CPC ............ *A61B 5/073* (2013.01); *A61B 5/4845* (2013.01); *A61B 2562/02* (2013.01); *A61B 2562/162* (2013.01); *A61B 2562/164* (2013.01)

(58) Field of Classification Search
  CPC ... A61B 5/073; A61B 5/4845; A61B 2562/02; A61B 2562/162; A61B 2562/164;
  (Continued)

(56) References Cited

U.S. PATENT DOCUMENTS

| | | | |
|---|---|---|---|
| 2005/0055039 A1* | 3/2005 | Burnett | A61B 17/12022 606/151 |
| 2009/0137866 A1* | 5/2009 | Boyden | A61B 5/4839 600/102 |

(Continued)

OTHER PUBLICATIONS

Witkiewitz et al., Advances in the science and treatment of alcohol use disorder. Science Advances. Sep. 2, 20195;5:eaax4043. 11 pages.

(Continued)

*Primary Examiner* — Eric F Winakur
*Assistant Examiner* — Jonathan Drew Moroneso
(74) *Attorney, Agent, or Firm* — Wolf, Greenfield & Sacks, P.C.

(57) ABSTRACT

Drug delivery articles, resident articles, and retrieval systems e.g., for gram-level dosing, are generally provided. In some embodiments, the residence articles are configured for transesophageal administration, transesophageal retrieval, and/or gastric retention to/in a subject. In certain embodiments, the residence article includes dimensions configured for transesophageal administration with a gastric resident system. In some cases, the residence article may be configured to control drug release e.g., with zero-order drug (Continued)

kinetics with no potential for burst release for weeks to months. In some embodiments, the residence articles described herein comprise biocompatible materials and/or are safe for gastric retention. In certain embodiments, the residence article includes dimensions configured for transesophageal retrieval. In some cases, the residence articles described herein may comprise relatively large doses of drug (e.g., greater than or equal to 1 gram).

19 Claims, 44 Drawing Sheets

(58) Field of Classification Search
CPC ....... A61B 5/0002; A61B 5/01; A61B 5/6861; A61B 5/6871; A61B 5/7435; Y02A 90/10; A61M 31/00; G16H 20/10; G16H 20/60; G16H 20/70; G16H 40/63; G16H 50/20
See application file for complete search history.

(56) References Cited

U.S. PATENT DOCUMENTS

| | | | |
|---|---|---|---|
| 2015/0150561 A1 | 6/2015 | Burnett et al. | |
| 2016/0198978 A1* | 7/2016 | Nemoto | A61B 5/7435 600/302 |
| 2017/0106099 A1* | 4/2017 | Bellinger | A61M 31/002 |
| 2017/0266112 A1* | 9/2017 | Bellinger | A61K 47/10 |
| 2019/0209090 A1 | 7/2019 | Langer et al. | |
| 2019/0351202 A1* | 11/2019 | Melamud | A61B 5/14539 |
| 2022/0071559 A1* | 3/2022 | Jones | C12Q 1/00 |

OTHER PUBLICATIONS

Xu et al., Advances in understanding addiction treatment and recovery. Science Advances. Oct. 1, 20196;5:eaaz6596. 3 pages.
International Search Report and Written Opinion for International Application No. PCT/US2021/031759, dated Sep. 10, 2021.
[No Author Listed], Aasld/Idsa Hcv Guidance: Recommendations for Testing, Managing, and Treating Hepatitis C. Clin Liver Dis (Hoboken). Nov. 2018; 12(5):117. Epub Dec. 14, 2018.
[No Author Listed], Bringing innovation to the front line for impact: Long-acting technologies for the prevention and treatment of major infectious diseases Compendium of Technical and Market Information. Unitaid. World Health Organization. Geneva, Switzerland. Nov. 2018:174 pages.
[No Author Listed], Digimeds to Optimize Adherence in Patients With Hepatitis C and Increased Risk for Nonadherence (DASH). Clinical Trials Identifier NCT03164902. Proteus Digital Health, Inc. Dec. 13, 2018. Last accessed Dec. 29, 2021 from <https://clinicaltrials.gov/ct2/show/record/NCT03164902>. 6 pages.
[No Author Listed], Global Hepatitis Report, 2017. World Health Organization. Global Hepatitis Porgramme. Geneva, Switzerland. Apr. 2017:83 pages.
[No Author Listed], Guidelines for the care and treatment of persons diagnosed with chronic hepatitis C virus infection. Global Hepatitis Programme. World Health Organization. Geneva, Switzerland. Jul. 2018:108 pages.
[No Author Listed], Impact Story: Paving the Way to Hepatitis C Elimination. Unitaid. World Health Organization. Geneva, Switzerland. Aug. 2018:4 pages.
[No Author Listed], Ledipasvir-Sofosbuvir (Harvoni). Hepatitis C Online. University of Washington. Accessed Dec. 29, 2021 as available Jun. 16, 2019 from <https://web.archive.org/web/20190616120401/https://www.hepatitisc.uw.edu/page/treatment/drugs/ledipasvir-sofosbuvir>. 3 pages.
[No Author Listed], Patient Engagement. Technical Series on Safer Primary Care. World Health Organization. Geneva, Switzerland. 2016:26 pages.
[No Author Listed], Progress Report on Access to Hepatitis C Treatment: Focus on Overcoming Barriers in Low- and Middle-income Countries. World Health Organization. Geneva, Switzerland. Mar. 2018:68 pages.
Abdel-Razek, LBP-08-The World's Largest Hepatitis C Screening Program in Egypt. International Liver Congress. Vienna, Austria. Apr. 10-14, 2019:1 page.
Afdhal et al., Ledipasvir and sofosbuvir for untreated HCV genotype 1 infection. N Engl J Med. May 15, 2014;370(20):1889-98. doi: 10.1056/NEJMoa1402454. Epub Apr. 11, 2014.
Akiyama et al., Intensive Models of Hepatitis C Care for People Who Inject Drugs Receiving Opioid Agonist Therapy: A Randomized Controlled Trial. Ann Intern Med. May 7, 2019;170(9):594-603. doi: 10.7326/M18-1715. Epub Apr. 9, 2019. Author manuscript provided. 25 pages.
Babaee et al., Temperature-responsive biometamaterials for gastrointestinal applications. Science Translational Medicine. Apr. 17, 2019;11(488):13 pages.
Babusis et al., Sofosbuvir and Ribavirin Liver Pharmacokinetics in Patients Infected with Hepatitis C Virus. Antimicrob Agents Chemother. Apr. 26, 2018;62(5):e02587-17. doi: 10.1128/AAC.02587-17. 11 pages.
Barua et al., Restrictions for Medicaid Reimbursement of Sofosbuvir for the Treatment of Hepatitis C Virus Infection in the United States. Ann Intern Med. Aug. 4, 2015;163(3):215-23. doi: 10.7326/M15-0406.
Bellinger et al., Oral, ultra-long-lasting drug delivery: Application toward malaria elimination goals. Sci Transl Med. Nov. 16, 2016;8(365):365ra157. doi: 10.1126/scitranslmed.aag2374. Author manuscript provided. 25 pages.
Bellows et al., Cost-effectiveness of emergency contraception options over 1 year. Am J Obstet Gynecol. May 2018;218(5):508.e1-508.e9. doi: 10.1016/j.ajog.2018.01.025. Epub Feb. 1, 2018. Author manuscript provided. 18 pages.
Bethea et al., Should we treat acute hepatitis C? A decision and cost-effectiveness analysis. Hepatology. Mar. 2018;67(3):837-46.
Beusterien et al., Societal preference values for advanced melanoma health states in the United Kingdom and Australia. Br J Cancer. Aug. 4, 2009;101(3):387-9. doi: 10.1038/sj.bjc.6605187. Epub Jul. 14, 2009.
Bose et al., Effects of polycaprolactone on alendronate drug release from Mg-doped hydroxyapatite coating on titanium. Mater Sci Eng C Mater Biol Appl. Jul. 1, 2018;88:166-171. doi: 10.1016/j.msec.2018.02.019. Epub Feb. 24, 2018. Author manuscript provided. 19 pages.
Bosworth et al., Physicochemical characterisation of degrading polycaprolactone scaffolds. Polymer Degradation and Stability. Dec. 2010;95(12):2269-76. Epub Oct. 1, 2010.
Bresnick, High-cost hepatitis C pill sees 8% non-adherence rate. Health IT Analytics. Xtelligent Healthcare Media, LLC. Danvers, MA. Sep. 18, 2014:4 pages.
Brown et al., Medication adherence: WHO cares? Mayo Clin Proc. Apr. 2011;86(4):304-14. doi: 10.4065/mcp.2010.0575. Epub Mar. 9, 2011.
Chhatwal et al., Cost-effectiveness and budget impact of hepatitis C virus treatment with sofosbuvir and ledipasvir in the United States. Ann Intern Med. Mar. 17, 2015;162(6):397-406. doi: 10.7326/M14-1336. Author manuscript provided. 22 pages.
Cooke et al., Accelerating the elimination of viral hepatitis: a Lancet Gastroenterology & Hepatology Commission. Lancet Gastroenterol Hepatol. Feb. 2019;4(2):135-184.
Duerig et al., An overview of nitinol medical applications. Materials Science and Engineering: A. Dec. 15, 1999;273-5:149-60. Epub Dec. 14, 1999.
Falade-Nwulia et al., Oral Direct-Acting Agent Therapy for Hepatitis C Virus Infection: A Systematic Review. Ann Intern Med. May 2, 2017;166(9):637-648. doi: 10.7326/M16-2575. Epub Mar. 21, 2017. Author manuscript provided. 20 pages.
Finkelstein et al., Incremental cost-effectiveness of evidence-based non-surgical weight loss strategies. Clin Obes. Apr. 2019;9(2):e12294. doi: 10.1111/cob.12294. Epub Jan. 24, 2019. 10 pages.

(56) References Cited

OTHER PUBLICATIONS

Flexner et al., Creating demand for long-acting formulations for the treatment and prevention of HIV, tuberculosis, and viral hepatitis. Current Opinion in HIV and AIDS. Jan. 2019;14(1):13-20.

Foreman et al., Forecasting life expectancy, years of life lost, and all-cause and cause-specific mortality for 250 causes of death: reference and alternative scenarios for 2016-40 for 195 countries and territories. Lancet. Nov. 10, 2018;392(10159):2052-2090. doi: 10.1016/S0140- 6736(18)31694-5. Epub Oct. 16, 2018.

Fu et al., Drug release kinetics and transport mechanisms from semi-interpenetrating networks of gelatin and poly(ethylene glycol) diacrylate. Pharm Res. Sep. 2009;26(9):2115-24. doi: 10.1007/s11095-009-9923-1. Epub Jun. 25, 2009. Author manuscript provided. 27 pages.

Goyanes et al., Effect of geometry on drug release from 3D printed tablets. Int J Pharm. Oct. 30, 2015;494(2):657-663. doi: 10.1016/j.ijpharm.2015.04.069. Epub Apr. 28, 2015.

Grebely et al., Direct-acting antiviral agents for HCV infection affecting people who inject drugs. Nat Rev Gastroenterol Hepatol. Nov. 2017;14(11):641-651. doi: 10.1038/nrgastro.2017.106. Epub Aug. 23, 2017.

Gritsenko et al., Ledipasvir/Sofosbuvir (harvoni): improving options for hepatitis C virus infection. P&T. Apr. 2015;40(4):256-9, 76.

Hutchins et al., Quantifying the utility of taking pills for preventing adverse health outcomes: a cross-sectional survey. BMJ Open. May 11, 2015;5(5):e006505. doi: 10.1136/bmjopen-2014-006505. 9 pages.

Jutabha et al., Randomized study comparing banding and propranolol to prevent initial variceal hemorrhage in cirrhotics with high-risk esophageal varices. Gastroenterology. Apr. 2005;128(4):870-81. doi: 10.1053/j.gastro.2005.01.047.

Kalantar-Zadeh et al., A human pilot trial of ingestible electronic capsules capable of sensing different gases in the gut. Nature Electronics. 2018;1:79-87. Epub Jan. 8, 2018.

Kanasty et al., A pharmaceutical answer to nonadherence: Once weekly oral memantine for Alzheimer's disease. Journal of Controlled Release. Jun. 2019;303:34-41. Epub Mar. 27, 2019.

Kim et al., Life satisfaction and frequency of doctor visits. Psychosom Med. Jan. 2014;76(1):86-93. doi: 10.1097/PSY.0000000000000024. Epub Dec. 12, 2013. Author manuscript provided. 19 pages.

Kini et al., Interventions to Improve Medication Adherence: A Review. JAMA. Dec. 18, 2018;320(23):2461-2473. doi: 10.1001/jama.2018.19271.

Kirby et al., Pharmacokinetic, Pharmacodynamic, and Drug-Interaction Profile of the Hepatitis C Virus NS5B Polymerase Inhibitor Sofosbuvir. Clin Pharmacokinet. Jul. 2015;54(7):677-90. doi: 10.1007/s40262-015-0261-7.

Kirtane et al., Development of an oral once-weekly drug delivery system for HIV antiretroviral therapy. Nat Commun. Jan. 9, 2018;9(1):2. doi: 10.1038/s41467-017-02294-6. 12 pages.

Klooster et al., Pharmacokinetics and disposition of rilpivirine (TMC278) nanosuspension as a long-acting injectable antiretroviral formulation. Antimicrob Agents Chemother. May 2010;54(5):2042-50. doi: 10.1128/AAC.01529-09. Epub Feb. 16, 2010.

Kong et al., 3D-Printed Gastric Resident Electronics. Adv Mater Technol. 2019;4(3):1800490. doi: 10.1002/admt.201800490. Epub Dec. 13, 2018. 11 pages.

Kreek et al., Current status of opioid addiction treatment and related preclinical research. Sci Adv. Oct. 2, 2019;5(10):eaax9140. doi: 10.1126/sciadv.aax9140. eCollection Oct. 2019. 11 pages.

Lawitz et al., Short-duration treatment with elbasvir/grazoprevir and sofosbuvir for hepatitis C: A randomized trial. Hepatology. Feb. 2017;65(2):439-450. doi: 10.1002/hep.28877. Epub Dec. 19, 2016.

Leffingwell et al., Continuous objective monitoring of alcohol use: twenty-first century measurement using transdermal sensors. Alcohol Clin Exp Res. Jan. 2013;37(1):16-22. doi: 10.1111/j.1530-0277.2012.01869.x. Epub Jul. 23, 2012. Author manuscript provided. 14 pages.

Lok et al., Benefits of Direct-Acting Antivirals for Hepatitis C. Ann Intern Med. Dec. 5, 2017;167(11):812-813. doi: 10.7326/M17-1876. Epub Oct. 17, 2017.

Machytka et al., Elipse, the first procedureless gastric balloon for weight loss: a prospective, observational, open-label, multicenter study. Endoscopy. Feb. 2017;49(2):154-160. doi: 10.1055/s-0042-119296. Epub Dec. 12, 2016.

Martin et al., Hepatitis C virus treatment for prevention among people who inject drugs: Modeling treatment scale-up in the age of direct-acting antivirals. Hepatology. Nov. 2013;58(5):1598-609. doi: 10.1002/hep.26431. Epub Aug. 26, 2013.

Mathus-Vliegen et al., Intragastric balloon for treatment-resistant obesity: safety, tolerance, and efficacy of 1-year balloon treatment followed by a 1-year balloon-free follow-up. Gastrointest Endosc. Jan. 2005;61(1):19-27. doi: 10.1016/s0016-5107(04)02406-x.

Matza et al., Health state utilities associated with attributes of treatments for hepatitis C. Eur J Health Econ. Dec. 2015;16(9):1005-18. doi: 10.1007/s10198-014-0649-6. Epub Dec. 7, 2014.

McClintock et al., Treatment completion for latent tuberculosis infection: a retrospective cohort study comparing 9 months of isoniazid, 4 months of rifampin and 3 months of isoniazid and rifapentine. BMC Infect Dis. Feb. 14, 2017;17(1):146. doi: 10.1186/s12879-017-2245-8. 8 pages.

Meltzer et al., The cost-effectiveness analysis of video capsule endoscopy compared to other strategies to manage acute upper gastrointestinal hemorrhage in the ED. Am J Emerg Med. Aug. 2014;32(8):823-32. doi: 10.1016/j.ajem.2013.11.012. Epub Nov. 13, 2013. Author manuscript provided. 26 pages.

Moore et al., Cost-effectiveness of directly observed versus self-administered therapy for tuberculosis. Am J Respir Crit Care Med. Oct. 1996; 154(4 Pt 1):1013-9. doi: 10.1164/ajrccm.154.4.8887600.

Nelson et al., All-Oral 12-Week Treatment With Daclatasvir Plus Sofosbuvir in Patients With Hepatitis C Virus Genotype 3 Infection: ALLY-3 Phase III Study. Hepatology. Apr. 2015;61(4):1127-1135.

Neumann et al., Updating cost-effectiveness—the curious resilience of the $50,000-per-QALY threshold. N Engl J Med. Aug. 28, 2014;371(9):796-7. doi: 10.1056/NEJMp1405158.

O'Shea et al., Alcoholic liver disease. Hepatology. Jan. 2010;51(1):307-28. doi: 10.1002/hep.23258.

Osterberg et al., Adherence to medication. N Engl J Med. Aug. 4, 2005;353(5):487-97. doi: 10.1056/NEJMra050100.

Quinlan, Gastric Balloon Cost, Insurance & Discounts. Bariatric Surgery Source. Jacksonville, FL. Jan. 4, 2019:8 pages. Last accessed Dec. 30, 2021 from <https://www.bariatric-surgery-source.com/gastric-balloon-cost.html#>.

Roland, Hepatitis C Cure Rate: Know the Facts. Healthline. Jun. 25, 2018:16 pages. Last accessed Dec. 3, 20210 from <https://www.healthline.com/health/hepatitis-c/hepatitis-c-cure-rate#outlook>.

Saab et al., Toward the elimination of hepatitis C in the United States. Hepatology. Jun. 2018;67(6):2449-2459. doi: 10.1002/hep.29685.

Salomon et al., Cost-effectiveness of treatment for chronic hepatitis C infection in an evolving patient population. JAMA. Jul. 9, 2003;290(2):228-37. doi: 10.1001/jama.290.2.228.

San Miguel et al., Cost-effectiveness analysis of sofosbuvir-based regimens for chronic hepatitis C. Gut. Aug. 2015;64(8):1277-88. doi: 10.1136/gutjnl-2014-307772. Epub Oct. 13, 2014.

Sarpel et al., Non-adherence is the most important risk factor for ledipasvir/sofosbuvir HCV treatment failure in the real world. NATAP Conference Report. Boston, MA. Nov. 2016:6 pages.

Scutti, Weight loss balloons now linked to 12 deaths. CNN. Jun. 4, 2018:5 pages. Last accessed Dec. 3, 20210 from <https://www.cnn.com/2018/06/04/health/weight-loss-balloon-deaths-bn/index.html#:~:text=An%20additional%20five%20patients%20have,said%20in%20an%20alert%20Monday.>.

Shah et al., Carvedilol vs. esophageal variceal band ligation in the primary prophylaxis of variceal hemorrhage: a multicentre randomized controlled trial. J Hepatol. Apr. 2014;60(4):757-64. doi: 10.1016/j.jhep.2013.11.019. Epub Nov. 28, 2013.

Sharma et al., A national study of cardiopulmonary unplanned events after GI endoscopy. Gastrointest Endosc. Jul. 2007;66(1):27-34. doi: 10.1016/j.gie.2006.12.040.

Shepardson et al., Cost-effectiveness of a 12-dose regimen for treating latent tuberculous infection in the United States. Int J Tuberc Lung Dis. Dec. 2013;17(12):1531-7. doi: 10.5588/ijtld.13.0423. Author manuscript provided. 42 pages.

(56) References Cited

OTHER PUBLICATIONS

Stahmeyer et al., Cost-Effectiveness of Treating Hepatitis C with Sofosbuvir/Ledipasvir in Germany. PLOS One. Jan. 3, 2017;12(1):e0169401. doi: 10.1371/journal.pone.0169401. eCollection 2017. 18 pages.

Thein et al., Estimation of utilities for chronic hepatitis C from SF-36 scores. Am J Gastroenterol. Mar. 2005;100(3):643-51. doi: 10.1111/j.1572-0241.2005.40976.x.

Thomas, Global Elimination of Chronic Hepatitis. N Engl J Med. May 23, 2019;380(21):2041-2050. doi: 10.1056/NEJMra1810477.

Triantos et al., Primary prophylaxis of variceal bleeding in cirrhotics unable to take beta-blockers: a randomized trial of ligation. Aliment Pharmacol Ther. Jun. 15, 2005;21(12):1435-43.

Trussell et al., Cost effectiveness of contraceptives in the United States. Contraception. Jan. 2009;79(1):5-14. doi: 10.1016/j.contraception.2008.08.003. Epub Sep. 25, 2008. Author manuscript provided. 22 pages.

Tuba et al., Towards the understanding of the molecular weight dependence of essential work of fracture in semi-crystalline polymers: A study on poly(s-caprolactone). Express Polymer Letters. 2014;8:869-79.

Tucker, FDA Approves 'Game Changer' Hepatitis C Drug Sofosbuvir. Medscape. New York, NY. Dec. 6, 2013:10 pages. Last accessed Dec. 30, 2021 from <https://www.medscape.com/viewarticle/817371>.

Verma et al., A gastric resident drug delivery system for prolonged gram-level dosing of tuberculosis treatment. Sci Transl Med. Mar. 13, 2019;11(483):eaau6267. doi: 10.1126/scitranslmed.aau6267. 9 pages.

Verma et al., Development of a long-acting direct-acting antiviral system for hepatitis C virus treatment in swine. PNAS. Jun. 2, 2020;117(22):11987-94.

Verma et al., Making the case: developing innovative adherence solutions for the treatment of tuberculosis. BMJ Glob Health. Feb. 1, 2019;4(1):e001323. doi: 10.1136/bmjgh-2018-001323. eCollection 2019. 4 pages.

Walsh et al., Economic impact of medication error: a systematic review. Pharmacoepidemiol Drug Saf. May 2017;26(5):481-497. doi: 10.1002/pds.4188. Epub Mar. 13, 2017.

Wang et al., Pin42 The Impact of Digital Medicine Program on Economic and Public Health Benefits For Hcv Coverage Expansion From a State Medicaid Perspective. Abstract. Value Health. May 2019;22(Supp 2):S201.

Ward et al., A Randomized Controlled Trial of Cash Incentives or Peer Support to Increase HCV Treatment for Persons With HIV Who Use Drugs: The CHAMPS Study. Open Forum Infect Dis. Apr. 9, 2019;6(4):ofz166. doi: 10.1093/ofid/ofz166. eCollection Apr. 2019. 9 pages.

Ward et al., What is Needed to Eliminate Hepatitis B Virus and Hepatitis C Virus as Global Health Threats. Gastroenterology. Jan. 2019;156(2):297-310. doi: 10.1053/j.gastro.2018.10.048. Epub Nov. 2, 2018.

Wong et al., Drugs for Chronic Hepatitis C Infection: Cost-Effectiveness Analysis. CADTH Therapeutic Review. Jan. 2016;3(1c):137 pages.

Xu et al., Deaths: Final Data for 2016. Natl Vital Stat Rep. Jul. 2018;67(5):1-76.

Zeuzem et al., Albinterferon alfa-2b dosed every two or four weeks in interferon-naïve patients with genotype 1 chronic hepatitis C. Hepatology. Aug. 2008;48(2):407-17. doi: 10.1002/hep.22403.

* cited by examiner

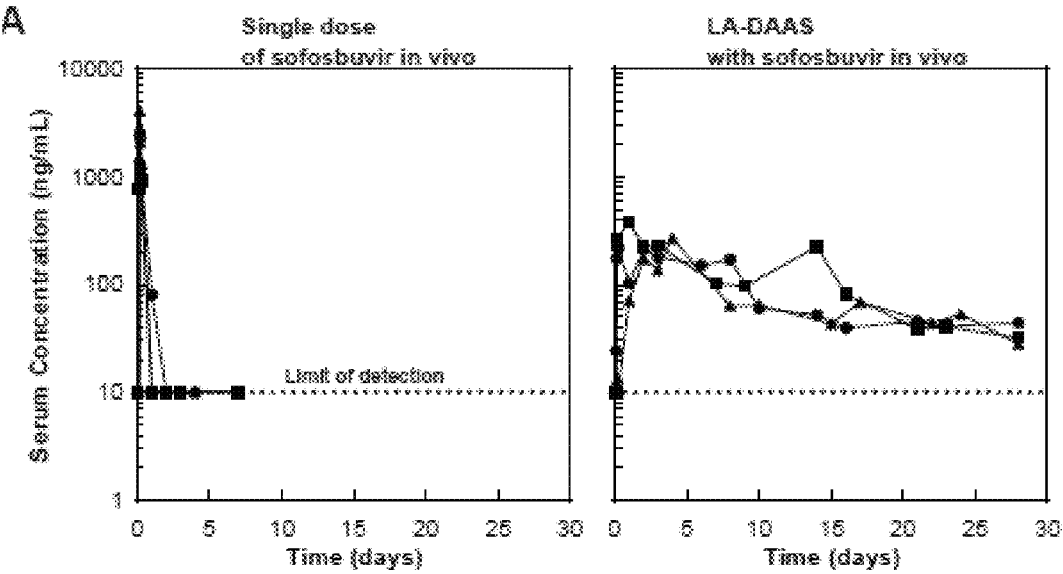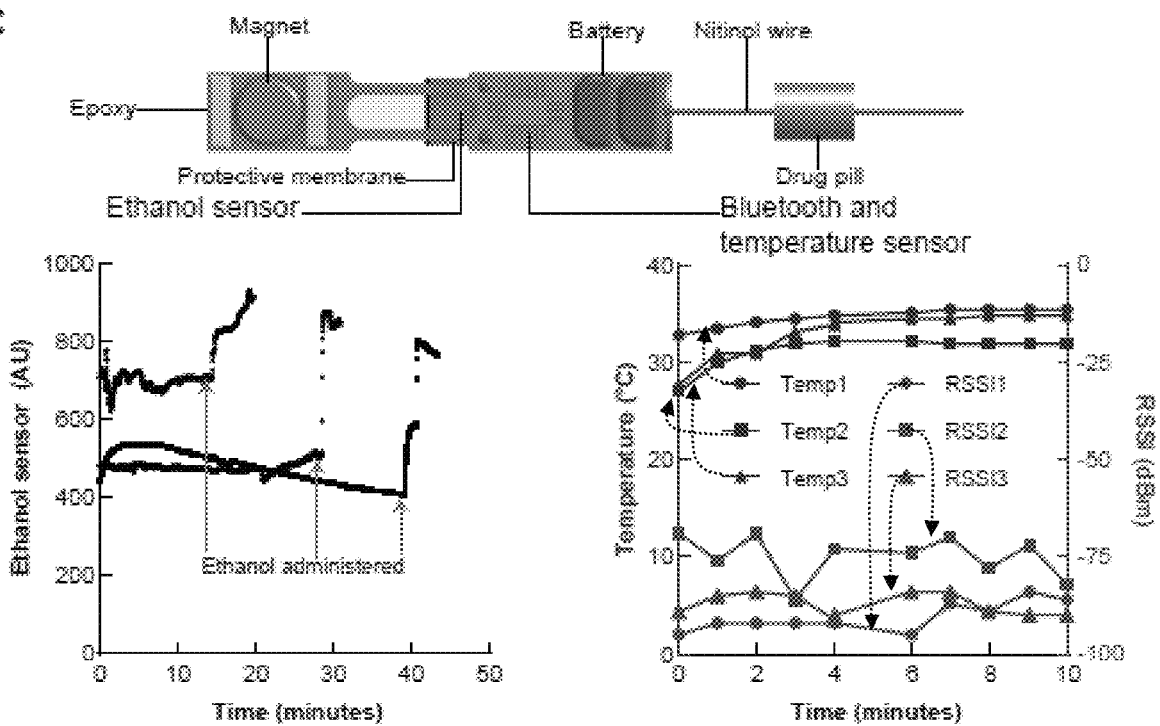
FIGs. 12A-12C

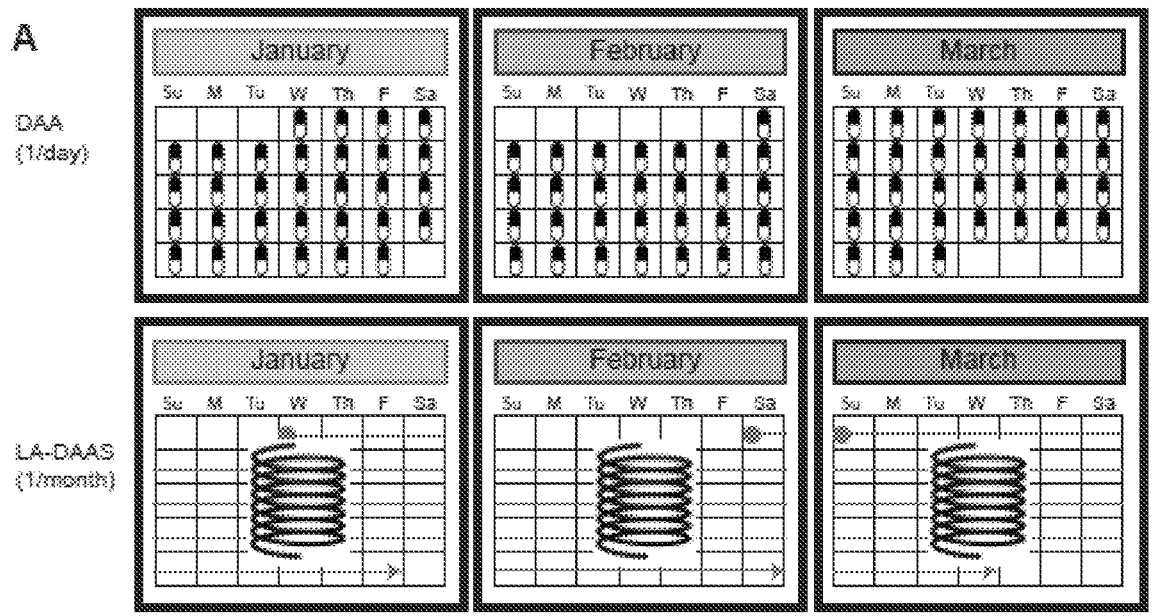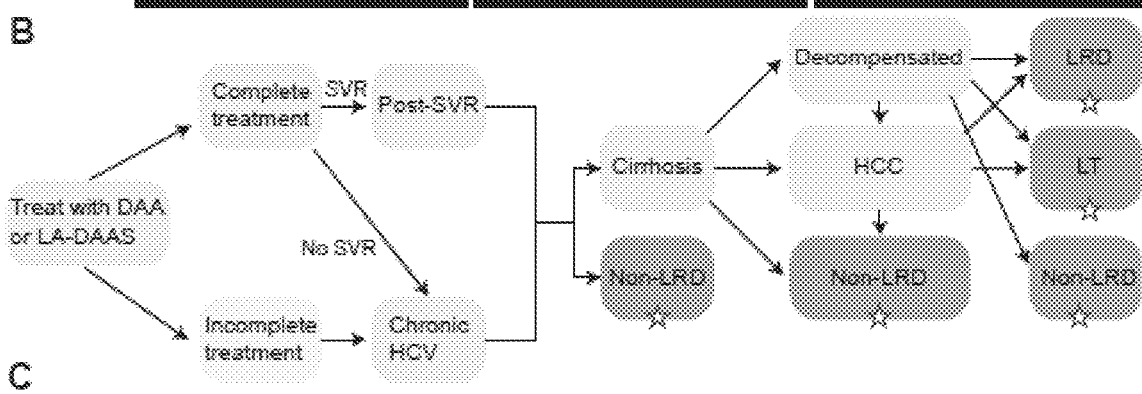
FIGs. 13A-13C

A

B

| Regression buffer length | 3 | 5 | 7 | 10 | 15 | 20 | 25 |
|---|---|---|---|---|---|---|---|
| Serrated valleys | 5 | 4 | 1 | 0 | 0 | 0 | 0 |
| Min Signal (MIN) | -16.5 | -16 | -15.5 | -14.8 | -13.2 | -11.6 | -10.2 |
| Max Noise (MAX) | -7 | -6.2 | -4.8 | -3.7 | -2.7 | -2 | -1.6 |
| SNR | 2.36 | 2.58 | 3.23 | 4 | 4.89 | 5.8 | 6.38 |

FIG. 33

GASTRORETENTIVE ARTICLES FOR ALCOHOL SENSING

RELATED APPLICATIONS

This application claims priority under 35 U.S.C. § 119(e) to U.S. Provisional Patent Application Ser. No. 63/023,280, filed May 12, 2020, and entitled "GASTRORETENTIVE ARTICLES FOR ALCOHOL SENSING," which is incorporated herein by reference in its entirety for all purposes.

FIELD

The present invention generally relates to gastroretentive articles for alcohol sensing.

BACKGROUND

Alcohol misuse affects over 16 million individuals in the United States. The morbidity of alcohol is staggering; over 88,000 people die from alcohol related causes every year. Currently, the diagnosis and treatment of alcoholism heavily rely on self-reported record of alcohol use. Due to issues such as stigma, patients often underreport their alcohol intake. Only a few technologies, such as transdermal and breath alcohol sensors, have been developed for point-of-care alcohol intake monitoring. Unfortunately, these technologies cannot provide accurate quantitative results as the captured signals are secondary information from metabolized alcohol. The inaccuracy of the available data on alcohol intake presents a huge barrier to effective treatment of alcohol use disorder.

Accordingly, improved systems, articles and methods are needed.

SUMMARY

The present invention generally relates to gastroretentive articles for alcohol sensing.

In one aspect, residence articles are provided. In some embodiments, the residence article comprises an alcohol sensor associated with a gastric residence article, the gastric residence article configured to be administered to a subject such that it is retained at a location internal to the subject for at least 24 hours.

In some embodiments, the residence article comprises a therapeutic agent associated with the residence article.

In some embodiments, the residence article is configured to dissociate such that the alcohol sensor may exit the subject.

In some embodiments, the residence article is configured to be retrieved.

In some embodiments, the residence article comprises a gas permeable membrane. In some embodiments, the gas permeable membrane comprises polytetrafluoroethylene, silicone, or combinations thereof.

In some embodiments, the residence article comprises an electronic component comprising a wireless transmitter, wherein the wireless transmitter is configured to transmit a signal from the location internal to the subject to a receiver positioned extracorporeal of the subject.

In some embodiments, the resident article comprises a degradable linker.

In some embodiments, the location internal to the subject is the stomach.

In some embodiments, the linker degrades, dissolves, disassociates, or mechanically weakens in a gastric environment which results in loss of retention shape integrity and passage out of a gastric cavity.

In some embodiments, the residence article comprises polymeric arms configured to maintain structural integrity during a residence period of the residence article.

In some embodiments, the residence article is configured for transesophageal administration.

In some embodiments, the residence article comprises a polymeric material having a reconfigurable shape and a hollow core.

In some embodiments, the residence article has a maximum dimension of greater than or equal to 28 cm.

In some embodiments, the therapeutic agent is present in the residence article in an amount greater than or equal to 1 gram.

In some embodiments, the residence article comprises an elastic wire disposed within the hollow core.

In some embodiments, the residence article comprises a magnetic component.

In some embodiments, the elastic wire comprises a superelastic alloy and/or shape memory material.

In another aspect, methods are provided. In some embodiments, the method comprises administering, to the subject, a residence article as in any preceding claim. In some embodiments, the residence article is administered orally.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 10A. (i) A nasogastric (NG) tube is placed in a patient to administer the LA-DAAS, and then the NG tube is removed. (ii) The LA-DAAS resides in the gastric cavity while releasing DAAs. (iii) The NG tube is once again placed in a patient to deploy a retrieval device for attachment and removal of the LA-DAAS from the gastric cavity. The LA-DAAS is compatible with communication with a personal device, such as a smart phone, engaging patients to track alcohol and temperature levels, how much drug is left, and schedule an appointment to receive another LA-DAAS. FIG. 10B. The LA-DAAS consists of a series of drug pills on a coiled superelastic nitinol wire with end protected with epoxy and a magnet for retrieval. One end of the LA-DAAS is equipped with a Bluetooth, temperature, and alcohol sensor. FIG. 10C. Representative radiographs of the LA-DAAS immediately after deployment and on day 30 in a swine model (n=3). Dashed circled indicate location of the LA-DAAS. FIG. 10D. Representative endoscopic images of the LA-DAAS immediately after deployment on and on day 30 in a swine model (n=3).

FIG. 11A. Drug-polymer pills are made by mixing drug with either silicone or poly(ε-caprolactone) (PCL) and then casting into a Petri dish or a three-dimensional (3-D) printed mold. Drug-silicone pills are extracted using a biopsy punch, and drug-PCL pills are extracted with a razor blade. Pills are then spray-coated with a pan coater. A cross-sectional image of a PCL-coated drug-PCL pill is shown. FIG. 11B. In vitro release of sofosbuvir from a drug pill in water with varying molecular weight of PCL. FIG. 11C. In vitro release of daclatasvir from a drug pill in water with varying molecular weight of PCL and PCL coating. FIG. 11D. In vitro release of ledipasvir from a drug pill in acetonitrile with varying silicone hardness. FIG. 11E. In vitro release of ribavirin from a drug pill in water with molecular weight of PCL and drug loading percentage. Error bars represent SD for n=3 samples.

FIGS. 12A-12C show in vivo applications of the long-acting direct-acting antiviral system (LA-DAAS), according to one set of embodiments. FIG. 12A. Left: Concentration-time profiles of the sofosbuvir metabolite GS-331007 in serum after administering a single dose of 400 mg (n=3). Right: Concentration-time profiles of the sofosbuvir metabolite GS-331007 in serum after administering the LA-DAAS, which had 11.2 g of sofosbuvir across two formulations (n=3; FIG. 12B. Area under the curve (AUC) and the duration of drug release for a single dose compared to the LA-DAAS administered in vivo, with the mean value and SD reported for n=3 samples in each group. FIG. 12C. Evaluation of the LA-DAAS electronic sensors (n=3) in euthanized swine. The analog signal of the ethanol sensor, temperature, and received signal strength indicator (RSSI) were measured after placement of the LA-DAAS in the stomach. Ethanol was administered at the time indicated by the up arrow. Temperature levels are shown above with the corresponding RSSI signal shown below for the same LA-DAAS.

FIGS. 13A-13C show monthly hepatitis C virus (HCV) treatment and cost-effectiveness of a long-acting direct-acting antiviral system (LA-DAAS), according to one set of embodiments. FIG. 13A. Illustration of two treatment strategies for HCV treatment: Current HCV treatment spans 12 weeks and involves daily administration of direct-acting antivirals (DAAs). The LA-DAAS can be administered once per month for HCV treatment. FIG. 13B. Schematic of the cost-effectiveness model for chronic HCV with two treatment strategies, DAA or LA-DAAS. Transition states are shown in blue. Starred health states indicate death states or liver transplant, after which patients exit the model. DAA: direct-acting antiviral, LA-DAAS: long-acting direct-acting antiviral system, SVR: sustained virologic response, LRD: liver-related death, non-LRD: non liver-related death, HCC: hepatocellular carcinoma, LT: liver transplant. FIG. 13C. Results for the cost-effectiveness analysis of DAA vs. LA-DAAS. Results for three cohorts are presented. In the base case, patients treated have average adherence to DAA and average likelihood of returning for NGT retreatment. In the PWID case, patients have lower adherence than the general population and are less likely to return for repeated NGT treatment. In the PWID: DOT case, patients in the DAA arm are PWID treated in a directly observed therapy (DOT) program. Cost and ICER are in United States dollars. In all cohorts, treatment with LA-DAAS was cost-effective. QALYs, quality-adjusted life-years; ICER, incremental cost-effectiveness ratio.

FIG. 14A. Design of the top half of the mold. FIG. 14B. Design of the bottom half of the mold. All units are in meters.

FIG. 15A. Diagram of the LA-DAAS. The coil height is fixed at 5 mm based on the size of the measured drug pill height, and the diameter of the LA-DAAS is kept constant at 104 mm based on the size of the nitinol fixture used. The length and weight of the ends of the device with the sensor is included as well (n=3). FIG. 15B. Calculated height of the LA-DAAS as a function of the drug weight, calculated by the number of pills that can fit on a single coil based on measurements of the pill height and diameter of the LA-DAAS. FIG. 15C. Calculated overall end-to-end length of the uncoiled LA-DAAS as a function of the drug weight. FIG. 15D. Calculated total weight of the LA-DAAS as a function of the drug weight incorporating the weight of the polymer matrix, nitinol wire, and ends of the device.

FIG. 16A. The animals' weight was measured every week from when it was brought into the animal facility until when it was euthanized. Week 0 denotes the week that the LA-DAAS was administered to the gastric cavity of the animal. At the end of week 4, the LA-DAAS was retrieved from the gastric cavity, and animal is euthanized shortly thereafter. Healthy young female Yorkshire swine are expected to gain 2-5 kg/week(1). FIG. 16B. After 4 weeks of gastric residence of the LA-DAAS, the stomach mucosa was assessed for any damage. A representative hematoxylin and eosin stain of stomach tissue at week 4 (when the LA-DAAS is retrieved and the animal is euthanized) is shown (n=3). The stomach is histologically normal, as assessed by a pathologist. There was no evidence of perforation, inflammation, or ulceration. FIG. 16C. Representative macroscopic image of the stomach tissue at the end of week 4 when a LA-DAAS was retrieved from the gastric cavity and the animal is euthanized to assess any damage to the mucosa (n=3).

FIG. 17A. Stability of sofosbuvir in SGF. FIG. 17B. Stability of daclatasvir in SGF. FIG. 17C. Stability of ribavirin in SGF. Error bars represent SD for n=3 samples in each group.

FIG. 19A. Stability of sofosbuvir. FIG. 19B. Stability of daclatasvir. FIG. 19C. Stability of ribavirin. FIG. 19D. Stability of ledipasvir. Error bars represent SD for n=3 samples in each group.

FIG. 20A. Physical parameters of pills with varying surface area to volume (SA/V) ratios. FIG. 20B. In vitro cumulative release of sofosbuvir from a drug pills in water. Drug release increases as the SA/V ratio increases. Error bars represent SD for n=3 samples in each group.

FIG. 21A. Concentration-time profiles of sofosbuvir (n=3). FIG. 21B. Concentration-time profiles of GS-331007 (n=3).

FIGS. 24A-24B shows addition of excipients to increase release rate of sofosbuvir from drug-PCL 80K pills, according to one set of embodiments. FIG. 24A. Table of sofosbuvir-PCL formulations with excipients. FIG. 24B. In vitro release profiles of sofosbuvir from drug-PCL pills over 7 days in water. Addition of Poloxamer 407 or poly(ethylene glycol) (PEG) molecular weight 3,500 increases the release rate of sofosbuvir from the drug-PCL pill. Error bars represent SD for n=3 samples in each group.

FIG. 29A. Sensitivity analysis for cost of the LA-DAAS. The LA-DAAS remains cost-effective compared to DAA up to $3,700. FIG. 29B. Sensitivity analysis for HCV treatment time course. The LA-DAAS is cost-effective for treatment courses of at least 5 weeks' duration.

FIG. 31A stand by; FIG. 31B alcohol ingestion detected; FIG. 31C wait; FIG. 31D steady state detected.

FIG. 32A the maximum noise induced by non-alcohol solution; FIG. 32B the minimum signal induced by alcohol solution.

FIG. 33 shows signal processing with varying the regression buffer length, according to one set of embodiments.

DETAILED DESCRIPTION

Figure 1:
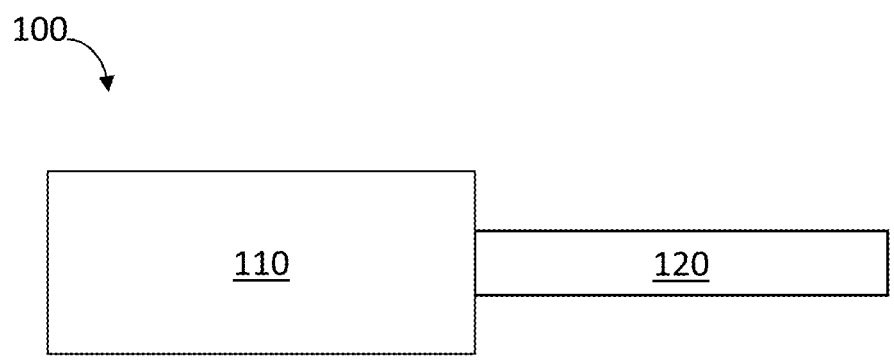
FIG. 1 is a schematic illustration of an exemplary gastric resident structure, also referred to herein as a gastric residence article, according to one set of embodiments.

Gastroretentive articles for alcohol sensing are generally provided. Some embodiments comprising administering (e.g., orally) a residence article to a subject (e.g., a patient) comprising an alcohol sensor, such that the residence article is retained at a location internal to the subject for a particular amount of time (e.g., at least about 24 hours) before exiting said location internal to the subject. In some embodiments, the resident structure, also referred to herein as a residence article, is configured for relatively long gastric residence and comprises an alcohol sensor. In some embodiments, the article comprises wireless communication capabilities. Advantageously, the articles described here may provide long-term alcohol intake monitoring at a location internal to a subject. In some embodiments, the residence device, also referred to herein as a residence article, comprises one or more additional components associated with the residence device such that the residence device is configured to be retained at a location internal to a subject for greater than or equal to 24 hours.

Advantageously, the structures and components described herein are configured for gastric residence of an alcohol sensor at a location internal to a subject without the need for a surgical procedure (e.g., an incision, implantation within layers of tissue). In some cases, the residence article may be administered to a subject. In some embodiments, the residence article is administered orally, rectally, vaginally, nasally, or urethrally. In some embodiments, the residence article is contained within a containing structure (e.g., during administration), as described in more detail below. In certain embodiments, upon reaching the location internal to the subject (e.g., in the gastrointestinal tract), at least a portion of the containing structure degrades such that the residence article obtains a configuration configured for gastric residence.

The term "subject," as used herein, refers to an individual organism such as a human or an animal. In some embodiments, the subject is a mammal (e.g., a human, a non-human primate, or a non-human mammal), a vertebrate, a laboratory animal, a domesticated animal, an agricultural animal, or a companion animal. Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the residence article. In some embodiments, the residence article is administered orally, to a subject.

The phrase "location internal to a subject" as used herein generally refers to an internal cavity (e.g., the mouth, the esophagus, the small intestine, the colon, the duodenum, the ileum, the jejunum, the stomach, or the rectum) of the subject. In some embodiments, the location internal to the subject is proximate (e.g., adjacent, directly adjacent) a gastric orifice such as the pylorus. In some embodiments, the residence article is configured to reside adjacent the gastric orifice such as the pylorus (e.g., the residence article has a largest cross-sectional area which does not permit passage through the pylorus). Those of ordinary skill in the art would understand, based upon the teachings of this specification, that a residence article is retained at a location internal to a subject when it does not substantially transit from said location absent a physical, chemical, or mechanical change to the residence article. By way of example and without wishing to be bound by a literal interpretation of such, a residence article is retained a location internal to a subject when it remains substantially proximate (e.g., adjacent, in contact with) that location over the duration of a residence time period (e.g., greater than or equal to 24 hours). By contrast, by way of a comparative example and without wishing to be bound by a literal interpretation of such, a residence article is not considered retained at a location internal to a subject as it transits the gastrointestinal tract (e.g., driven by gastrointestinal forces and/or motion such that it moves through the gastrointestinal tract). For example, a device that remains internal to a subject but transits the gastrointestinal tract over e.g., greater than or equal to 24 hours is not intended to be a device that is retained at a location internal to a subject for said greater than or equal to 24 hours, despite being internal to the subject. By way of example, a residence article that remains proximate the pylorus of the subject e.g., greater than or equal to 24 hours is intended to be considered a residence article that is retained at the location internal to the subject for said greater than or equal to 24 hours. Other residence time periods are also possible and are described in more detail below.

Those of ordinary skill in the art would understand, based upon the teachings of this specification, that residence does not require a strict adherence to a geometrically defined relative to location internal to a subject such that the residence article may move (e.g., as a result of gastrointestinal forces/motion) while being retained at the location internal to the subject. By way of example, and without wishing to be bound by a literal interpretation of such, a residence article is said to be retained e.g., in the stomach of the subject as long as the structure remains in the stomach and does not exit the stomach (e.g., via the pylorus) during the desired residence time period. In some embodiments, the structures described herein comprise a component that undergoes a change (e.g., a mechanical change) such that the residence article exits the location internal to the subject (e.g., passes through the pylorus).

The residence articles described herein comprise, in some embodiments, an alcohol sensor (e.g., that can directly access consumed alcohol inside the GI tract to perform an in-situ measurement). For example, a semiconductor gas sensor that is designed to detect volatile organic compounds may be used as an alcohol sensor to measure actual amounts of ethanol intake. A semiconductor gas sensor has the advantage, in some embodiments, of a small package form factor (e.g., smaller than 5 mm$^2$), high sensitivity, and/or fast response times. In some embodiments, the alcohol sensor can detect any organic compound, oxygen, hydrogen, and carbon dioxide. Non-limiting examples of suitable gas sensors include, commercial sensors such as MQ3B from WINSEN, BME680 from Bosch SENSORTEC, CCS811 from ams, MiCS5524 from SGX SENSORTECH, and SGP30 from SENSIRION.

According to some embodiments, at least a portion of the residence article is configured to degrade, dissolve, and/or disassociate into one or more forms capable of passing through a gastrointestinal tract (e.g., after a desired period of time). In some embodiments, the arms and/or core of the residence article may be selected such that each arm and/or the core dissolves, degrades, mechanically weakens, and/or mechanically separates from the residence article after a particular residence time period (and/or upon triggering from the residence article). The term residence time period generally refers to the length of time during which the residence article described herein is resided at a location internally of a subject, also referred to herein as a location internal to a subject, as measured from the time initially present in the location internally of the subject to the time at which the residence article no longer resides at the location internally of the subject due to, for example, degradation, dissolution, and/or exit of at least a portion of the residence article from the location internally of the subject. In an illustrative embodiment, the residence article may be orally administered such that the residence article resides at a location internally of the subject such as the small intestine and exits the small intestine (e.g., after degradation of at least a portion of the residence article such as the arms and/or the core), where the residence time period is measured as the length of time between when the residence article initially resides in the small intestine and when the residence article exits the small intestine.

In some embodiments, the arms of the residence article may comprise a degradable material. In some cases, the arms, the core, and/or a linker(s) may be configured to mediate disassembly of the residence article after, for example, delivery of a pharmaceutical agent for the residence time period (e.g., after greater than or equal to 24 hours), and safe passage through the lower intestinal tract of the subject. Exit from a location such as the small intestine may be achieved through changes in the mechanical properties of each arm (e.g., via biodegradation) such that the ability to resist passage through the small intestine is compromised. In some embodiments, the arms and/or the core may comprise a printed circuit board (PCB). In some embodiments, the core comprises a PCB, and further comprises a polymer molding (e.g., an Elastollan® molding) on the core PCB, which polymer molding imparts a resilient folding capability. In some embodiments, the arms comprise a PCB, and further comprise a polymer molding (e.g., a PCL molding) on the arm PCBs, which polymer molding imparts rigidity and biodegradability. In some embodiments, the core PCB and arm PCBs are connected via a flexible printed circuit (FPC) connector.

In some embodiments, the residence article comprises an alcohol sensor. For example, as illustrated in FIG. 1, residence article 100 comprises alcohol sensor 110 and additional component 120. Additional component 120 may be configured such that the residence device is retained at a location internal to a subject for greater than or equal to 24 hours. Such additional components (e.g., linkers, polymeric arms, polymer matrix, retrieval systems) are described in more detail, below. In some embodiments, the additional component comprises or is a gastric residence article configured to be administered to a subject such that it is retained at a location internal to the subject for at least 24 hours. In an exemplary set of embodiments, the residence article comprising a gastric residence article is administered such that the residence article enters the stomach of the subject and is retained in the stomach for a residence period (e.g., of greater than or equal to 24 hours). The residence article may be configured to transmit a signal from the residence article to a device external (e.g., extracorporeal) of the stomach and/or configured to receive a signal from a device external (e.g., extracorporeal) of the stomach. For example, in some embodiments, the residence article may be configured to transmit and/or receive physiological conditions about the subject such as e.g., temperature (e.g., gastric internal temperature), pH, pressure, or other biophysical characteristics. For example, the residence article may comprise (and/or be in electronic communication with) one or more sensors configured to determine one or more physiological conditions about the subject. In some embodiments, the residence article comprises one or more sensors (e.g., a biomolecular sensor, a gas sensor, a temperature sensor, a pressure sensor, a motion sensor, an accelerometer, a pH sensor, a biochemical sensor), a wireless identification microchip, and/or an imaging system (e.g., a camera). In some embodiments, the residence article is configured to generate and/or receive a signal (e.g., a wireless signal). In some embodiments, the signal triggers the residence article to release a pharmaceutical agent from the residence article. In some embodiments, the signal provides a physiological condition of the subject to the device external of the stomach. In some embodiments, the signal mediates the exit of the residence article from the stomach through the pylorus, as described herein.

In some embodiments, the residence article comprises an alcohol sensor associated with a gastric residence article, wherein the gastric residence article is configured to be administered to a subject such that it is retained at a location internal to the subject for at least 24 hours, and the residence article further comprises an electronic component comprising a wireless transmitter, wherein the wireless transmitter is configured to transmit a signal from the location internal to the subject to a receiver positioned extracorporeal of the subject. In certain embodiments, the alcohol sensor is integrated into the electric component. In certain embodiments, the residence article further comprises a gas permeable membrane, and the alcohol sensor is protected from gastrointestinal fluid by the gas permeable membrane. In some of any of the preceding embodiments, the residence article comprises an alcohol sensor associated with a gastric residence article, wherein the gastric residence article is configured to be administered to a subject such that it is retained at a location internal to the subject for at least 24 hours, and the residence article further comprises an electronic component comprising a wireless transmitter, wherein the wireless transmitter is configured to transmit a signal from the location internal to the subject to a receiver positioned extracorporeal of the subject, the alcohol sensor is integrated into the electric component, the residence article further comprises a gas permeable membrane, and the alcohol sensor is protected from gastrointestinal fluid by the gas permeable membrane. In some of any of the previous embodiments, gastric retention is achieved by device expansion, unfolding, folding, swelling or combinations thereof. In some of any of the preceding embodiments, the sensor is an electrochemical or semiconductor sensor. In some of any of the preceding embodiments, the gas permeable membrane comprises Polytetrafluoroethylene or silicone or combinations thereof.

In some embodiments, the residence article comprises one or more drug delivery modules. For example, in some embodiments, the residence article may be configured to, upon residence at a location internal to the subject, detect one or more biophysical conditions and/or deliver one or more pharmaceutical agents at the location internal to the subject. In some embodiments, the residence article is configured to deliver (e.g., release) one or more pharmaceutical agents in response to a physiological condition of the subject, a signal from a sensor on the residence article, and/or a signal received from a device external the subject. In some embodiments, the residence article comprises an alcohol sensor associated with a gastric residence article, wherein the gastric residence article is configured to be administered to a subject such that it is retained at a location internal to the subject for at least 24 hours, and further comprising a therapeutic agent associated with the residence article.

In some embodiments, a residence article comprises an alcohol sensor associated with a gastric residence article, the gastric residence article is configured to be administered to a subject such that it is retained at a location internal to the subject for at least 24 hours. In some of any of the preceding embodiments, the location internal to the subject is the stomach. In some of any of the preceding embodiments, the residence article is configured to dissociate such that the alcohol sensor may exit the subject. In some of any of the preceding embodiments, the residence article is configured to be retrieved. In some of any of the preceding embodiments, the residence article further comprises a gas permeable membrane. In certain embodiments, the alcohol sensor is protected from gastrointestinal fluid by the gas permeable membrane. In certain embodiments, the gas permeable membrane comprises polytetrafluoroethylene, silicone, or combinations thereof. In some of any of the preceding embodiments, the residence article comprises a degradable linker. In some of any of the preceding embodiments, the residence article comprises a linker that degrades, dissolves, disassociates, or mechanically weakens in a gastric environment which results in loss of retention shape integrity and passage out of a gastric cavity. In some of any of the preceding embodiments, the residence article comprises polymeric arms configured to maintain structural integrity during a residence period of the residence article. In some of any of the preceding embodiments, the residence article is configured for transesophageal administration. In some of any of the preceding embodiments, the residence article comprises a polymeric material having a reconfigurable shape and a hollow core. In some of any of the preceding embodiments, the residence article has a maximum dimension of greater than or equal to 28 cm. In some of any of the preceding embodiments, the therapeutic agent is present in the residence article in an amount greater than or equal to 1 gram. In some of any of the preceding embodiments, the residence article further comprises an elastic wire disposed within the hollow core. In certain embodiments, the elastic wire comprises a superelastic alloy and/or shape memory material. In some of any of the preceding embodiments, the residence article further comprises a magnetic component.

In some embodiments, methods comprising administering, to the subject, a residence article as in any embodiments herein, are provided.

Figure 2A:
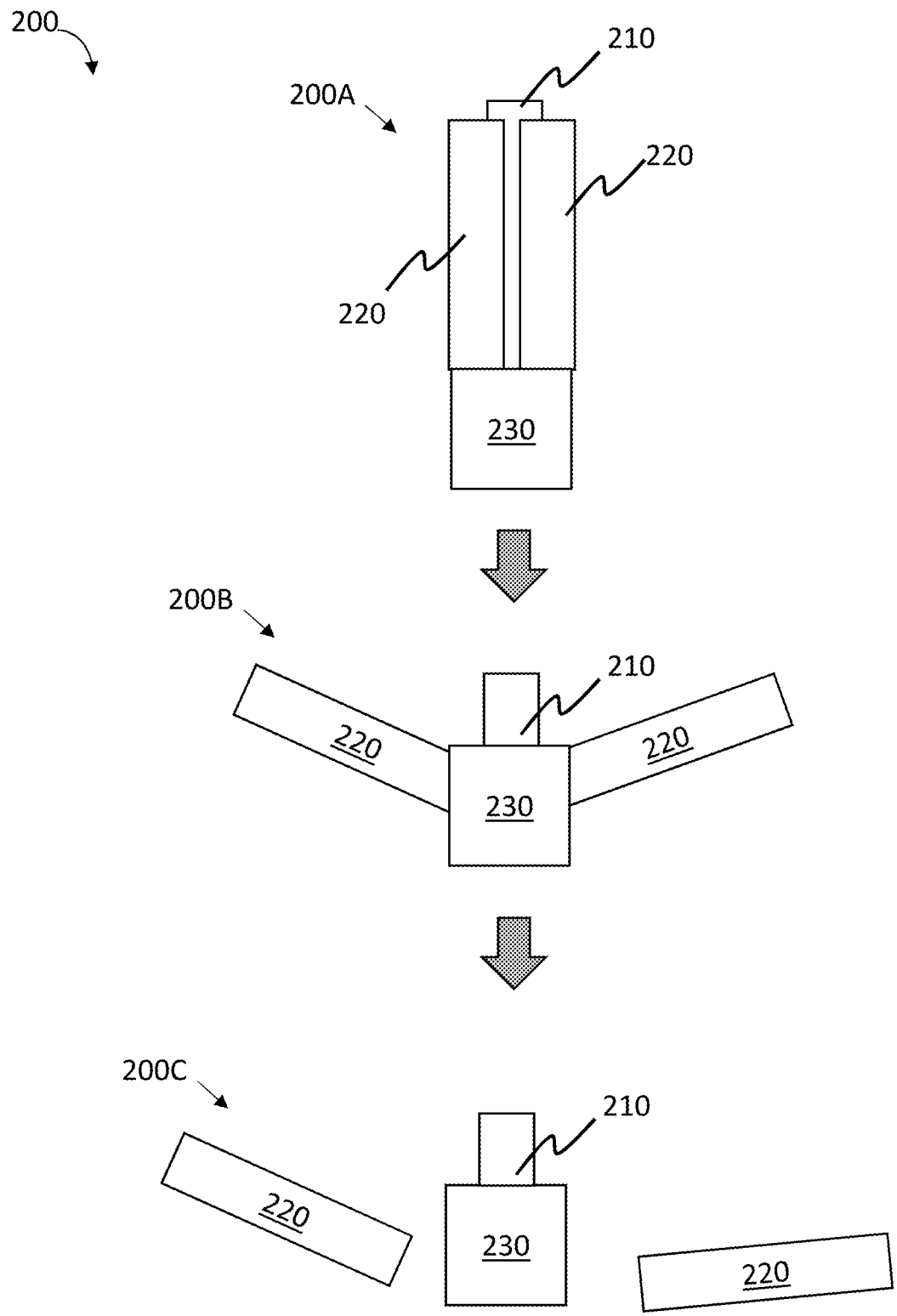
FIG. 2A is a schematic illustration of a gastric resident structure, according to one set of embodiments.

In some embodiments, at the end of the residence period, the residence article and/or the alcohol sensor is configured to pass from the location internal to the subject (e.g., exits the stomach through the pylorus). For example, as illustrated in FIG. 2A, residence article 200 comprises an alcohol sensor 210 linked to an additional component 230 and two or more arms 220. In some embodiments, residence article 200 has a first configuration 200A (e.g., a compressed configuration). In some embodiments, the first configuration is such that the residence article may be administered to a subject (e.g., introduced orally) and will transit through the gastrointestinal tract until reaching a location internal to the subject (e.g., the stomach, proximate the pylorus). In some embodiments, residence article 200 obtains a second configuration 200B (e.g., an expanded configuration) in which the residence article is retained at the location internal to the subject and does not pass through any internal orifices (e.g., is retained in the stomach and does not pass into the pylorus) under normal physiological conditions. In configuration 200B, arms 220 and/or alcohol sensor 210 expand such that residence article 200 is retained. In some embodiments, residence article 200 obtains a third configuration in which a degradable portion (e.g., component 230, arms 220) of the residence article dissolves, degrades, mechanically weakens, and/or mechanically separates from the residence article. In some such embodiments, the residence article and/or the residence article passes from the location internal to the subject (e.g., exits the stomach through the pylorus). As described herein, in some embodiments, residence article 200 obtains configuration 200B for a desired residence time period.

For example, in some embodiments, the residence article has a second configuration including a particular size and/or shape in a relaxed state (e.g., configuration 200B). In certain embodiments, the residence article may be folded from the second configuration into a first, folded configuration (configuration 200A). For example, in some cases, the folded/compressed residence article may be inserted within a capsule or other containment structure in the first configuration such that the residence article can be administered (e.g., orally). The capsule or other containment structure can be, in some cases, configured to dissolve such that the residence article is released at a particular location internal to the subject whereby upon release, it can reversibly revert to the second configuration (e.g., by elastic recoil). In some embodiments, the residence article is configured to adopt a shape and/or size in vivo that slows or prevents further transit in a body (e.g., gastric, small intestine) cavity until a desired time (e.g., upon dissolution of the microneedles and/or the arms of the residence article). In some embodiments, the residence article adopts a shape and/or size configured for prolonged retention (e.g., gastric residence) upon release from a capsule/container and/or retaining structure/element. In some embodiments, the residence article is configured for adopting a shape and/or size configured for gastric deployment (after being stored in its encapsulated/folded shape and/or size) for the residence time period. In some embodiments, the residence time period is greater than or equal to 24 hours, greater than or equal to 48 hours, greater than or equal to 3 days, greater than or equal to 7 days, greater than or equal to 1 month, greater than or equal to 6 months, or greater than or equal to 1 year. In certain embodiments, the residence time period is less than or equal to 2 years, less than or equal to 1 year, less than or equal to 6 months, less than or equal to 1 month, less than or equal to 7 days, less than or equal to 3 days, or less than or equal to 48 hours. Combinations of the above-referenced ranges are also possible (e.g., greater than or equal to 24 hours and less than or equal to 2 years, greater than or equal to 24 hours and less than or equal to 1 year, greater than or equal to 48 hours and less than or equal to 7 days, greater than or equal to 3 days and less than or equal to 1 month, greater than or equal to 7 days and less than or equal to 6 months, greater than or equal to 1 month and less than or equal to 1 year). Other ranges are also possible.

In some embodiments, the residence article is configured and designed such that a pharmaceutical agent is released from the residence article for at least a portion of the residence time period, in one or more of the ranges listed above (e.g., greater than or equal to 24 hours and less than or equal to 2 years).

Figure 2B:
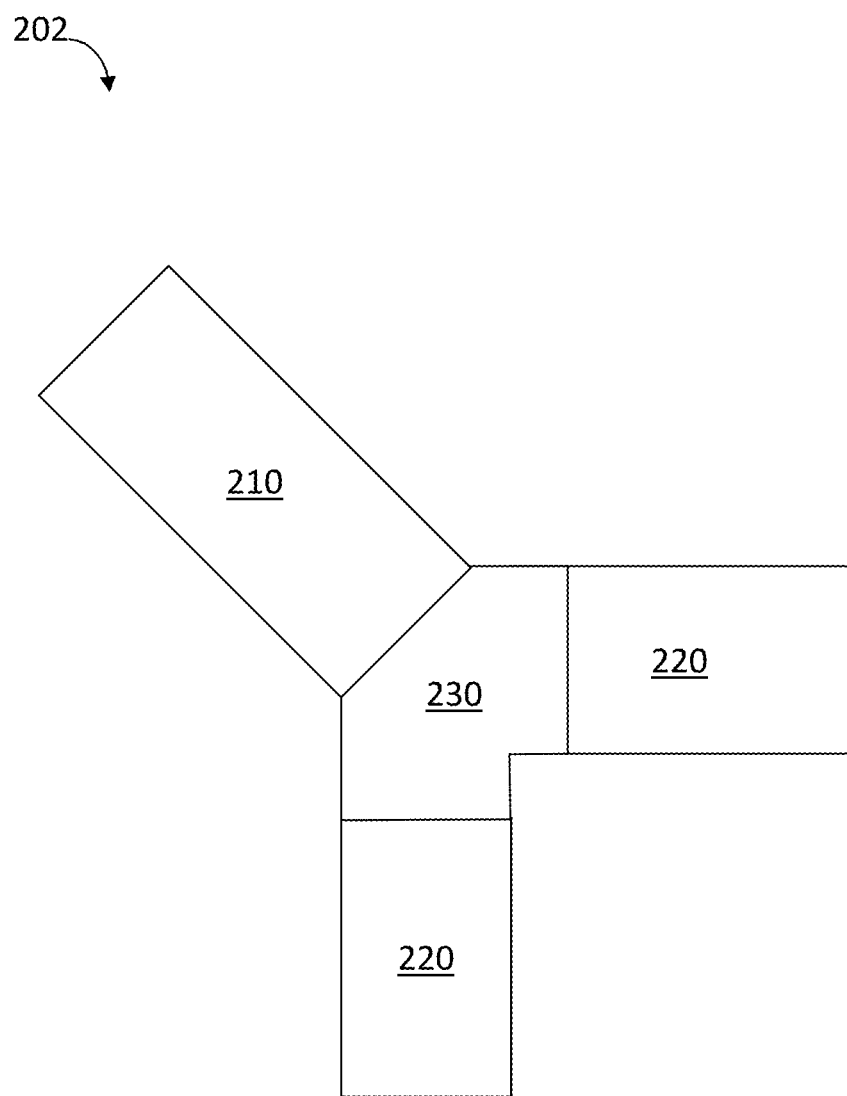
FIG. 2B is a schematic illustration of a gastric resident structure, according to one set of embodiments.

Referring now to FIG. 2B, in some embodiments, a residence article 202 comprises an alcohol sensor 210 associated with (e.g., connected to) an additional component 230 and two or more arms 220. In some embodiments, additional component 230 is an elastic component (e.g., an elastic core). Elastic components are described in more detail, below. In some embodiments, additional component 230 and arms 220 comprise the same material. In certain embodiments, additional component 230 and arms 220 comprise different materials. In an exemplary set of embodiments, additional component 230 comprises a thermoplastic polyurethane and arms 220 comprise polylactic acid. Other materials are also possible and are described in more detail below.

In some embodiments, the residence article comprises a degradable component linked to the residence article such that the degradable component mediates the exit of the residence article from the stomach through the pylorus of the subject. For example, in some embodiments, at least a portion of additional component 230 is configured to dissolve, degrade, mechanically weaken, and/or mechanically separate from the residence article such that the residence article exits the location internal to the subject (e.g., passes from the stomach through the pylorus). In some embodiments, at least a portion of each arm 220 is configured to dissolve, degrade, mechanically weaken, and/or mechanically separate from the second component, also referred to herein as the additional component, such that the residence article exits the location internal to the subject (e.g., passes from the stomach through the pylorus).

Figure 2C:
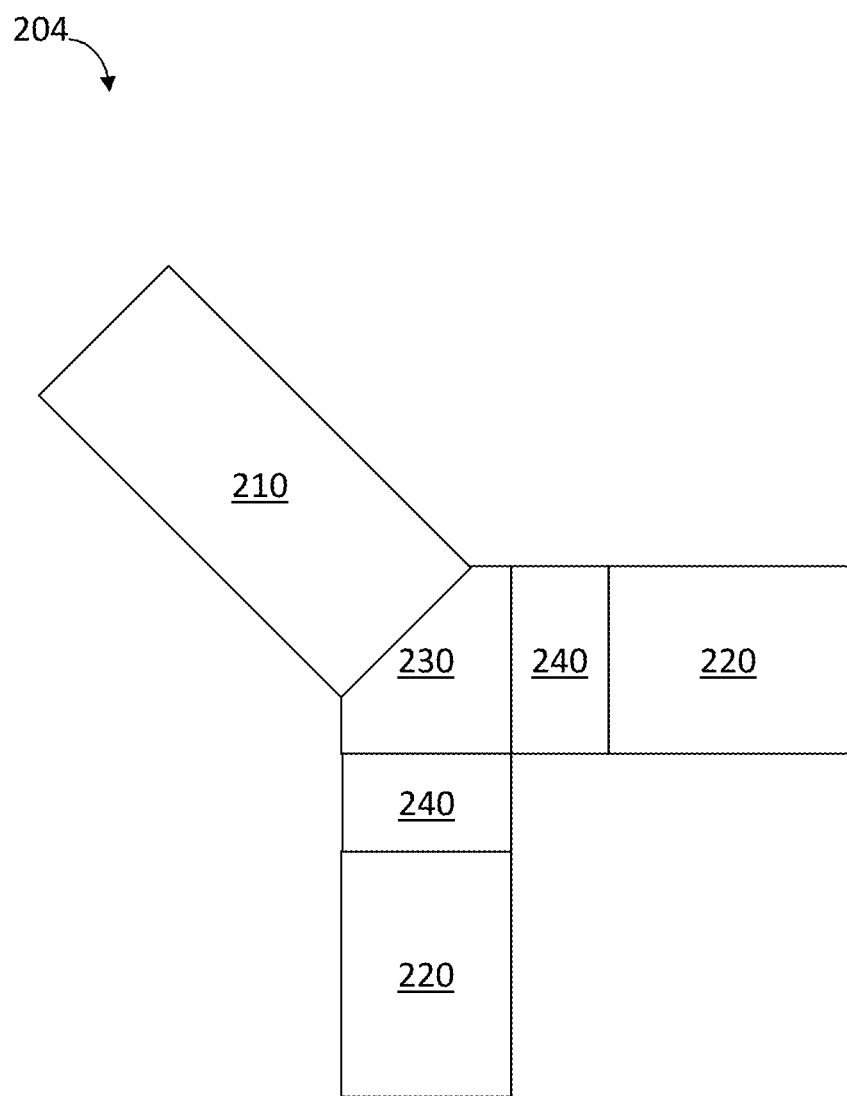
FIG. 2C is a schematic illustration of a gastric resident structure, according to one set of embodiments.

In some embodiments, a signal (e.g., from the residence article, from an external device received by the residence article) triggers the degradable component(s) to dissolve, degrade, mechanically weaken, and/or mechanically separate from the residence article. In some embodiments, as shown illustratively in FIG. 2C, a residence article 204 comprises alcohol sensor 210, two or more arms 220, an additional component 230 (e.g., an elastic component), and linkers 240. In some embodiments, linkers 240 are degradable linkers configured to dissolve, degrade, mechanically weaken, and/or mechanically separate from the residence article such that the residence article exits the location internal to the subject (e.g., passes from the stomach through the pylorus). While two linkers 240 are shown in FIG. 2C, those of ordinary skill in the art would understand that additional (or fewer) linkers are possible and may be positioned at other locations in the residence article (e.g., such that when the linker(s) dissolve, degrade, mechanically weaken, and/or mechanically separate the residence article exits the location internal to the subject).

For example, in some embodiments, the residence article is delivered to a subject by administering orally, to a subject, a residence article comprising an alcohol sensor such that the residence article is retained at a location internal to the subject for at least about 24 hours, wherein the residence article comprises an elastic core (e.g., the second component), two or more polymeric arms associated with the elastic core, and the alcohol sensor associated with the elastic core.

In some embodiments, the residence article is removed from the location internal to the subject by degrading the degradable linker(s) and/or one or more additional degradable components.

In some embodiments, the degradable component(s) (or arms) may be dissolved, degraded, mechanically weakened, and/or mechanically separated from the residence article by applying a voltage to the degradable component. In some embodiments, the residence article is configured to apply the voltage to the degradable component(s), as described in more detail below.

In some embodiments, the degradable component(s) comprise a plurality of carbonaceous particles, carbon nanotubes, and/or conductive particles e.g., such that when the voltage is applied, the degradable component dissolves, degrades, mechanically weakens, and/or mechanically separates. Without wishing to be bound by theory, the plurality of carbonaceous particles, carbon nanotubes, and/or conductive particles may generate heat in the presence of an applied voltage such that the degradable component(s) mechanically weaken (e.g., undergo thermoplastic weakening). In some embodiments, the degradable component comprises an electroactive adhesive (e.g., a mixture of a low melting temperature polymer with electrically conductive nanomaterials). In an exemplary embodiment, the electroactive adhesive comprises poly(caprolactone) and a plurality of carbon nanotubes. In some embodiments, the degradable components comprise a plurality of particles comprising graphene and/or nickel. The carbonaceous/conductive particles may have any suitable average cross-sectional dimension (e.g., diameter). In some embodiments, the degradable component(s) comprise a plurality of particles (e.g., carbonaceous particles, conductive particles) having an average cross-sectional dimension of greater than or equal to 0.1 microns, greater than or equal to 0.2 microns, greater than or equal to 0.5 microns, greater than or equal to 1 micron, greater than or equal to 2 microns, greater than or equal to 5 microns, greater than or equal to 10 microns, greater than or equal to 20 microns, greater than or equal to 50 microns, greater than or equal to 100 microns, greater than or equal to 200 microns, greater than or equal to 500 microns, or greater than or equal to 750 microns. In some embodiments, the average cross-sectional dimension is less than or equal to 1000 microns, less than or equal to 750 microns, less than or equal to 500 microns, less than or equal to 200 microns, less than or equal to 50 microns, less than or equal to 20 microns, less than or equal to 10 microns, less than or equal to 5 microns, less than or equal to 2 microns, less than or equal to 1 microns, less than or equal to 0.5 microns, or less than or equal to 0.2 microns. Combinations of the above-referenced ranges are possible (e.g., greater than or equal to 0.1 microns and less than or equal to 1000 microns, greater than or equal to 0.1 microns and less than or equal to 1 micron, greater than or equal to 0.2 microns and less than or equal to 10 microns). Other ranges are also possible.

As used herein, the term "nanotube" is given its ordinary meaning in the art and refers to a substantially cylindrical molecule or nanostructure comprising a fused network of primarily six-membered aromatic rings. In some cases, nanotubes may resemble a sheet of graphite formed into a seamless cylindrical structure. It should be understood that the nanotube may also comprise rings or lattice structures other than six-membered rings. Nanotubes may have a diameter of the order of nanometers and a length on the order of millimeters, or, on the order of tenths of microns, resulting in an aspect ratio greater than 100, 1000, 10,000, or greater. In some cases, the nanotube is a carbon nanotube (CNT). The term "carbon nanotube" refers to nanotubes comprising primarily carbon atoms and includes single-walled nanotubes (SWNTs), double-walled nanotubes (DWNTs), multi-walled nanotubes (MWNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube). In some cases, the nanotube may have a diameter less than 1 μm, less than 100 nm, 50 nm, less than 25 nm, less than 10 nm, or, in some cases, less than 1 nm (or greater than or equal to 0.5 nm, greater than or equal to 1 nm, greater than or equal to 10 nm, greater than or equal to 25 nm, greater than or equal to 50 nm, or greater than or equal to 100 nm). Combinations of the above-referenced ranges are also possible (e.g., less than 1 micron and greater than or equal to 0.5 nm, less than 100 nm and greater than or equal to 1 nm, less than 50 nm and greater than or equal to 10 nm). Other ranges are also possible.

As described above, in some embodiments, the residence article has a particular configuration including a particular size and/or shape (e.g., a multi-armed star) in a relaxed state. In certain embodiments, the residence article may be folded such that it obtains a second, compressed configuration. For example, in some cases, the residence article may be folded within a capsule in the second configuration such that the residence article may be delivered orally. The capsule may, in some cases, dissolve such that the residence article is released at a particular location internal to the subject (e.g., in the stomach) and reversibly obtain the first configuration (i.e. recoil). In some embodiments, the device is configured to adopt a shape and/or size that slows or prevents further transit in a gastric cavity (e.g., passage from the body of the stomach through the pylorus). In some embodiments, the device adopts a shape and/or size capable of retention (e.g., gastric residence) upon release from the soluble container and/or soluble retaining element. In some embodiments, the device is capable of adopting a shape and/or size capable of gastric residence after being stored in its encapsulated shape and/or size for durations greater than 24 hours, including up to about one year. In some embodiments, the mechanical properties of the device are optimized for safe transient retention in an internal orifice such as the gastric cavity for durations greater than 24 hours, including up to about one year.

Certain of the devices, systems, and methods described herein can be useful, for example, in achieving gastric residence and/or slowed transit via oral administration for extended in vivo residence and administration of therapeutic, diagnostic, and/or enhancement agents. The devices and systems described herein may offer several advantages as compared to traditional residence and/or orally administered devices and systems including, for example, the ability to adopt a shape and/or size small enough to be ingested by a subject; adopt a shape and/or size that slows or prevents further transit in the gastric cavity (e.g., passage from the body of the stomach through the pylorus); load high levels (e.g., high mass) of therapeutic, diagnostic, and/or enhancement agents; control release of therapeutic, diagnostic, and/or enhancement agents with low to no potential for burst release; maintain stability of therapeutic, diagnostic, and/or enhancement agents in a hostile environment such as the gastric environment for an extended duration; maintain safety with low to no potential for gastric or intestinal obstruction and/or perforation; and/or degrade/dissolve/disassociate into one or more forms capable of passing through a gastrointestinal tract. In certain embodiments, the devices and systems described herein can be configured with durable residence times greater than at least twenty-four hours and lasting up to about one year, or more. In some embodiments, the systems, devices, and methods described herein are compatible with subjects, including, but not limited to humans and non-human animals. In further embodiments, the systems and devices can be configured to deliver a wide variety of therapeutic, diagnostic, and/or enhancement agents, thus potentially increasing and even maximizing adherence rates.

Those of ordinary skill in the art would be capable of selecting suitable methods for forming the residence article, arm(s), and/or elastic core, based upon the teachings of this specification. In an exemplary set of embodiments, at least a portion of the residence article (e.g., at least a portion of the residence article, arm(s), and/or elastic core) are formed using 3D printing.

In some embodiments, the residence article comprises wireless capabilities for enabling suitable communication with other devices/systems (e.g., for controlling aspects of the residence article, controlling/monitoring physiological conditions of the subject (e.g., at the location internal to the subject), etc.). Wireless devices are generally known in the art and may include, in some cases, LTE, WiFi and/or Bluetooth systems. In some embodiments, the residence articles described herein comprise such a wireless device.

In some embodiments, the residence article may be configured to adjust various parameters based on physiological and/or external metrics. For example, in some embodiments, the residence article is configured to adjust the rate and/or amount of a pharmaceutical agent released from the residence article (e.g., stored within one or more reservoirs associated with the residence article) e.g., in response to a signal from a sensor in electrical or wireless communication with and/or associated with (e.g., embedded within) the residence article. In some embodiments, the residence article adjusts the rate and/or amount of a pharmaceutical agent released from the residence article in response to an input from the user and/or a signal from the sensor. In some embodiments, the residence article is associated with one or more reservoirs configured for the release of a pharmaceutical agent. In some embodiments, the one or more reservoirs may release a portion of the pharmaceutical agent contained therein in response to a signal received from a sensor in electrical or wireless communication with the residence article.

Non-limiting examples of suitable sensors for use with the structures and methods described herein include temperature sensors (e.g., monitoring internal temperature, ambient temperature, temperature of a component associated with the residence article such as a thermally sensitive polymer), physiological/biometric sensors (e.g., heart rate, electrical activity, neuronal activity), accelerometers (e.g., for measuring breathing rate, activity levels, sleeping behavior/patterns), and environmental sensors (e.g., pH, biologic concentration, chemical concentration).

In some embodiments, the residence article is associated with and/or comprises a power source. The power source may include any appropriate material(s), such as one or more batteries, photovoltaic cells, etc. Non-limiting examples of suitable batteries include Li-polymer (e.g., with between 100 and 1000 mAh of battery life), Li-ion, nickel cadmium, nickel metal hydride, silver oxide, or the like. In some cases, the battery may apply a voltage (e.g., to a degradable material as described herein) in response to a physiological and/or external metric and/or signal (e.g., by a user). For example, the voltage may be used to trigger the exit of the residence article by e.g., applying a voltage to thermally sensitive degradable component as described herein. For example, the average magnitude of the voltage applied to the degradable component(s) may be between 0.001 to 0.01 V, between 0.01 to 0.1 V, between 0.1 V and 10.0 V, between 1.0 V and 8.0 V, between 2.0 V and 5.0 V, between 0.1 V and 5.0 V, between 0.1 V and 1.5 V, between 0.1 V and 1.0 V, between 1.0 V and 3.0 V, between 3.0 V and 8.0 V, or any other appropriate range.

Any residence article circuitry may be implemented by any suitable type of analog and/or digital circuitry. For example, the residence article circuitry may be implemented using hardware or a combination of hardware and software. When implemented using software, suitable software code can be executed on any suitable processor (e.g., a microprocessor) or collection of processors. The one or more residence articles can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein may, in some cases, comprise at least one computer-readable storage medium (e.g., RAM, ROM, EEPROM, flash memory or other memory technology, or other tangible, non-transitory computer-readable storage medium) encoded with a computer program (i.e., a plurality of executable instructions) that, when executed on one or more processors, performs the above-discussed functions of one or more embodiments. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

In some embodiments, the second component (e.g., the elastic core) is an elastic polymeric component. In certain embodiments, the use of an elastic polymeric component and may impart particular mechanical properties to the structure. For example, in some cases, the structure may be capable of undergoing relatively high compressive forces (e.g., compressive forces present within the stomach and/or intestine of a subject) such that the structure does not break and/or is retained at a location internally of the subject (e.g., at or above an orifice such as the pylorus). In certain embodiments, the structure may be capable of being folded (e.g., without breaking). For example, the elastic polymeric component may be capable of undergoing relatively high levels of bending stresses without breaking and/or being permanently significantly deformed. In some embodiments, the elastic polymeric component and/or the structure may be capable of substantial recoil. That is to say, after mechanically deforming the elastic polymeric component and/or the structure comprising the elastic polymeric component, the structure may return substantially to its original configuration prior to the mechanical deformation being applied (e.g., having substantially minimal creep deformation).

Several screening tests may be used to determine suitable materials for use as the elastic polymeric component. For example, the elastic polymeric component may be capable of undergoing at least about 45 degrees, at least about 60 degrees, at least about 90 degrees, at least about 120 degrees, at least about 150 degrees, or about 180 degrees of mechanical bending deformation without breaking. In certain embodiments, the elastic polymeric component may be capable of undergoing less than or equal to about 180 degrees, less than or equal to about 150 degrees, less than or equal to about 120 degrees, less than or equal to about 90 degrees, or less than or equal to about 60 degrees of mechanical bending deformation without breaking. Combinations of the above-referenced ranges are also possible (e.g., between about 45 degrees and about 180 degrees, between about 60 degrees and about 180 degrees, between about 60 degrees and about 120 degrees, between about 90 degrees and about 180 degrees). Other ranges are also possible.

In some cases, the elastic polymeric component may be capable of remaining in a deformed configuration (e.g., at least about 45 degrees of mechanical bending deformation) for a relatively prolonged period of time. For example, in some embodiments, the elastic polymer component has a shelf-life in a deformed configuration (e.g., at least about 45 degrees of mechanical bending deformation) of at least about 24 hours, at least about 1 week, at least about 1 month, at least about 1 year, or at least about 2 years and be capable of returning (i.e. recoiling) substantially to its pre-deformation configuration. In certain embodiments, the elastic polymer component has a shelf life in a deformed configuration of less than or equal to about 3 years, less than or equal to about 2 years, less than or equal to about 1 year, less than or equal to about 1 month, or less than or equal to about 1 week and be capable of returning (i.e. recoiling) substantially to its pre-deformation configuration. Combinations of the above-referenced ranged are also possible (e.g., between about 24 hours and about 3 years, between about 1 week and 1 year, between about 1 year and 3 years). Other ranges are also possible.

In some embodiments, the elastic polymeric component is relatively flexible. In certain embodiments, the elastic polymeric component may be selected such that it is capable of undergoing large angle deformation for relatively long periods of time without undergoing significant non-elastic deformation. In some such embodiments, the elastic polymeric component may have a strength of recoil sufficient to substantially return the elastic polymeric component to its pre-deformed shape within less than about 30 minutes, within less than about 10 minutes, within less than about 5 minutes, or within less than about 1 minute after release of the mechanical deformation. Those skilled in the art would understand that returning to its pre-deformed shape shall be understood to not require absolute conformance to a mathematical definition of shape, but, rather, shall be understood to indicate conformance to the mathematical definition of shape to the extent possible for the subject matter so characterized as would be understood by one skilled in the art most closely related to such subject matter.

In some embodiments, the elastic polymeric component has a particular elastic modulus. In some embodiments, the elastic modulus of the elastic polymeric component ranges between about 0.1 MPa and about 30 MPa. In some embodiments, the elastic modulus of the elastic polymeric component is at least about 0.1 MPa, at least about 0.2 MPa, at least about 0.3 MPa, at least about 0.5 MPa, at least about 1 MPa, at least about 2 MPa, at least about 5 MPa, at least about 10 MPa, at least about 20 MPa, or at least about 25 MPa. In certain embodiments, the elastic modulus of the elastic polymeric component is less than or equal to about 30 MPa, less than or equal to about 25 MPa, less than or equal to about 20 MPa, less than or equal to about 10 MPa, less than or equal to about 5 MPa, less than or equal to about 2 MPa, less than or equal to about 1 MPa, less than or equal to about 0.5 MPa, less than or equal to about 0.3 MPa, or less than or equal to about 0.2 MPa. Combinations of the above referenced ranges are also possible (e.g., between about 0.1 MPa and about 30 MPa, between about 0.3 MPa and about 10 MPa). Other ranges are also possible. Those skilled in the art would be capable of selecting suitable methods for determining the elastic modulus of a polymeric component including, for example, tensile mechanical characterization under ASTM D638 and/or compressive mechanical characterization under ASTM D575.

In some embodiments, the elastic polymeric component undergoes a relatively low amount of creep during mechanical deformation. For example, in certain embodiments, the elastic polymeric component has a minimum creep rate of less than or equal to about 0.3 mm/mm/hr, less than or equal to about 0.2 mm/mm/hr, less than or equal to about 0.1 mm/mm/hr, less than or equal to about 0.08 mm/mm/hr, less than or equal to about 0.05 mm/mm/hr, less than or equal to about 0.03 mm/mm/hr, or less than or equal to about 0.02 mm/mm/hr. In certain embodiments, the elastic polymeric component has a minimum creep rate of at least about 0.01 mm/mm/hr, at least about 0.02 mm/mm/hr, at least about 0.03 mm/mm/hr, at least about 0.05 mm/mm/hr, at least about 0.08 mm/mm/hr, at least about 0.1 mm/mm/hr, or at least about 0.2 mm/mm/hr. Combinations of the above referenced ranges are also possible (e.g., between about 0.01 mm/mm/hr and about 0.3 mm/mm/hr, between about 0.02 mm/mm/hr and about 0.1 mm/mm/hr, between about 0.02 mm/mm/hr and about 0.05 mm/mm/hr, between about 0.05 mm/mm/hr and about 0.3 mm/mm/hr). Other ranges are also possible. Minimum creep rate can be determined, in some embodiments, according to ASTM D-638. Briefly, a sheet of the elastic polymeric material is prepared, as described below, and cut into a standard dumbbell die. The specimens can be loaded into grips of an Instron testing machine and the gauge length measured using a digital micrometer. A constant stress corresponding to 30% of the ultimate tensile strength of each material may be applied to the specimens for 60 min at constant temperature (e.g., room temperature) and the creep (in mm/mm) versus time (in hours) can be plotted. The minimum creep rate is the slope of the creep vs. time curve prior to secondary creep.

Those skilled in the art would be capable of determining suitable methods for tuning the mechanical properties (e.g., elastic modulus, creep behavior) of the elastic polymeric component by, for example, varying the molar ratios of monomeric and/or polymeric units (e.g., increasing the amount of high molecular weight polycaprolactone or other polymers used in the elastic polymeric component), varying polymer cross-linking density, varying the concentration of cross-linking agents used in the formation of the polymer, varying the crystallinity of the polymer (e.g., by varying the ratio of crystalline and amorphous regions in the polymer) and/or the use of additional or alternative materials (e.g., incorporating materials such as bis(isocyanatomethyl)-cyclohexane).

In some embodiments, the elastic polymeric component does not substantially swell in the presence of biological fluids such as blood, water, bile, gastric fluids, and/or the like. In some embodiments, the elastic polymer component swells between about 0.01 vol % and about 10 vol % in a biological fluid as compared to the volume of the elastic polymer component in the dry state (e.g., at atmospheric conditions and room temperature). For example, in certain embodiments, the elastic polymeric component swells by less than about 10 vol %, less than about 5 vol %, less than about 2 vol %, or less than about 1 vol % in a biological fluid as compared to the volume of the elastic polymeric component in the dry state (e.g., at atmospheric conditions and room temperature). Those skilled in the art would be capable of selecting suitable methods for determining the amount of swelling of an elastic polymeric component based upon the teachings of this specification including, for example, measuring the volume of the elastic polymeric component in the dry state at atmospheric conditions and room temperature, submerging the component in a biological fluid (e.g., blood, water, bile, gastric fluids, and/or the like) and measuring the percent change in volume of the component after about 60 minutes.

The elastic polymeric component is generally biocompatible. The term "biocompatible," as used herein, refers to a polymer that does not invoke an adverse reaction (e.g., immune response) from an organism (e.g., a mammal), a tissue culture or a collection of cells, or if the adverse reaction does not exceed an acceptable level. In some embodiments, the elastic polymeric component comprises polymers, their networks, and/or multi-block combinations of, for example, polyesters, including but not limited to, polycaprolactone, poly(propylene fumarate), poly(glycerol sebacate), poly(lactide), poly(glycol acid), poly(lactic-glycolic acid), polybutyrate, and polyhydroxyalkanoate; polyethers, including but not limited to, poly(ethylene oxide) and poly(propylene oxide); polysiloxanes, including but not limited to, poly(dimethylsiloxane); polyamides, including but not limited to, poly(caprolactam); polyolefins, including but not limited to, polyethylene; polycarbonates, including but not limited to poly(propylene oxide); polyketals; polyvinyl alcohols; polyoxetanes; polyacrylates/methacrylates, including but not limited to, poly(methyl methacrylate) and poly(ethyl-vinyl acetate); polyanhydrides; and polyurethanes (e.g., thermoplastic polyurethanes). In some embodiments, the polymer is cross-linked. In some embodiments, the elastic polymeric component comprises a polymer composite comprising two or more chemically similar polymers or two or more chemically distinct polymers. In an exemplary embodiment, the elastic polymeric component comprises an isocyanate cross-linked polyurethane generated from low molecular weight monomers such as polycaprolactone. In some embodiments, the low molecular weight monomers comprise one or more hydroxyl functional groups (e.g., a diol, a triol).

In some embodiments, each arm has particular mechanical properties such that the arm material resists brittle breakage but is sufficiently stiff such that it may withstand internal physiological pressure and/or maintain residence of the structure. In some embodiments, the arm(s) comprises polymers, their networks, and/or multi-block combinations of, for example, polyesters, including but not limited to, polycaprolactone, poly(propylene fumarate), poly(glycerol sebacate), poly(lactide), poly(glycol acid), poly(lactic-glycolic acid), polybutyrate, and polyhydroxyalkanoate; polyethers, including but not limited to, poly(ethylene oxide) and poly(propylene oxide); polysiloxanes, including but not limited to, poly(dimethylsiloxane); polyamides, including but not limited to, poly(caprolactam); polyolefins, including but not limited to, polyethylene; polycarbonates, including but not limited to poly(propylene oxide); polyketals; polyvinyl alcohols; polyoxetanes; polyacrylates/methacrylates, including but not limited to, poly(methyl methacrylate) and poly(ethyl-vinyl acetate); polyanhydrides; and polyurethanes (e.g., thermoplastic polyurethanes). In some embodiments, the polymer is cross-linked. In some embodiments, the arm(s) comprises a polymer composite comprising two or more chemically similar polymers or two or more chemically distinct polymers. In an exemplary embodiment, the arm(s) comprises an isocyanate cross-linked polyurethane generated from low molecular weight monomers such as polycaprolactone. In some embodiments, the low molecular weight monomers comprise one or more hydroxyl functional groups (e.g., a diol, a triol).

Several screening tests may be used to select suitable materials for use as the arm(s). For example, the arm(s) may be selected such that the arm(s) has a flexural moduli greater than about 100 MPa, greater than about 120 MPa, greater than about 150 MPa, or greater than about 200 MPa. In some embodiments, the arm(s) has a flexural modulus less than or equal to about 250 MPa, less than or equal to about 200 MPa, less than or equal to about 150 MPa, or less than or equal to about 120 MPa. Combinations of the above referenced ranges are also possible (e.g., between about 100 MPa and about 250 MPa). Other ranges are also possible. Those skilled in the art would be capable of selecting suitable methods for determining the flexural moduli of a polymeric component including, for example, plotting the flexural stress versus strain and taking the slope of the linear portion of the curve.

In certain embodiments, the arm(s) may be selected to have a flexural strength of at least about 10 MPa. For example, in some embodiments, the arm(s) has a flexural strength of at least about 10 MPa, at least about 15 MPa, at least about 20 MPa, at least about 30 MPa, or at least about 40 MPa. In certain embodiments, the arm(s) has a flexural strength of less than or equal to about 50 MPa, less than or equal to about 40 MPa, less than or equal to about 30 MPa, less than or equal to about 20 MPa, or less than or equal to about 15 MPa. Combinations of the above referenced ranges are also possible (e.g., between about 10 MPa and about 50 MPa). Other ranges are also possible. Those skilled in the art would be capable of selecting suitable methods for determining the flexural strength of the arm(s) including, for example, determining the flexural stress at failure of the polymeric material.

The arm(s) materials may be selected such that they maintain their mechanical properties over a residence time period (e.g., during the release of the active substance and/or during residence in an orifice). Residence time periods are described in more detail, below. In some embodiments, the arm(s) materials are selected such that the device may be retained within an orifice located internally of the subject (e.g., a gastric orifice) for at least 24 hours, at least 48 hours, at least one week, at least one month, or at least one year. In certain embodiments, the arm(s) materials are selected such that the device may be retained within an orifice location internally of the subject for less than or equal to about 2 years, less than or equal to about 1 year, less than or equal to about 1 month, less than or equal to about 1 week, or less than or equal to about 48 hours. Combinations of the above-referenced ranges are also possible (e.g., between about 24 hours and about 2 years, between about 48 hours and about 2 years, between about 1 week and about 1 year). Other ranges are also possible.

As described above, in some embodiments, at least one of the two or more arms may be configured to dissolve, degrade, mechanically weaken, and/or mechanically separate from the residence article such that the residence article passes from the stomach through the pylorus after a desired residence time (and/or upon triggering from the residence article).

In some embodiments, the residence article, the second component, one or more arm(s), and/or the linker comprises an enteric polymer. In some embodiments, the enteric polymer includes, but is not limited to, cellulose acetate phthalate (CAP), hypromellose (INN) or hydroxypropyl methylcellulose (HPMC), and EUDRAGIT® (available from Evonik Industries AG (Essen, Germany)).

In some embodiments, the dissolution of an enteric polymer can be triggered by, for example, ingestion of an alkali solution. In some embodiments, the enteric polymer has the capacity for dissolution between pH 4-8. According to some embodiments, the enteric polymer is selected such that the enteric polymer is stable in an acidic gastric environment (i.e., having a pH1 to pH4) but dissolves in a more alkali region of the gastrointestinal tract distal to the pylorus (i.e., having a pH greater than 5.5) and can serve as a linker.

For example, in certain embodiments, the enteric polymer does not substantially degrade at a pH ranging between about 1 and about 5. In some embodiments, the enteric polymer does not substantially degrade at a pH of at least about 1, at least about 2, at least about 3, at least about 4, or at least about 4.5. In certain embodiments, the enteric polymer does not substantially degrade at a pH of less than or equal to about 5, less than or equal to about 4.5, less than or equal to about 4, less than or equal to about 3, or less than or equal to about 2. Combinations of the above reference ranges are also possible (e.g., between about 1 and about 4.5, between about 1 and about 5, between about 1 and 4). Other ranges are also possible.

In certain embodiments, the enteric polymer degrades substantially at a pH ranging between about 4 and about 8. In some embodiments, the enteric polymer degrades substantially at a pH of at least about 4, at least about 5, at least about 6, at least about 6.5, at least about 7, or at least about 7.5. In certain embodiments, the enteric polymer degrades substantially at a pH of less than or equal to about 8, less than or equal to about 7.5, less than or equal to about 7, less than or equal to about 6.5, less than or equal to about 6, or less than or equal to about 5. Accommodations of the above reference ranges are also possible (e.g., between about 4 and about 8, between about 5 and about 8, between about 6.5 and about 7.5). Other ranges are also possible.

Those skilled in the art would be capable of selecting suitable methods for determining degradation of the enteric polymers based upon the teachings of the specification including, determining the solubility of the enteric polymer in an aqueous solution having a pH of less than about 3 and/or dissolving the enteric polymer in aqueous solution having a pH of greater than or equal to about 6, measured at body temperature (e.g., between about 35° C. and about 38° C.) over time period of between about 4 and about 40 days.

In some embodiments, the enteric polymer is an enteric elastomer. In certain embodiments, the enteric elastomer exhibits reversible elongation when stretched from 50% to 1500% of its initial length. For example, in some embodiments, the enteric elastomer exhibits reversible elongation when stretched from at least about 50%, at least about 100%, at least about 200%, at least about 400%, at least about 500%, at least about 1000%, at least about 1200%, or at least about 1400% of its initial length. That is to say, in some embodiments, the enteric elastomer has difference in average length after deformation versus before deformation (e.g., stretching) of less than about 10%, less than about 5%, less than about 2%, or less than about 1%. In certain embodiment, the enteric elastomer exhibits reversible elongation when stretched from less than or equal to about 1500%, less than or equal to about 1400%, less than or equal to about 1200%, less than or equal to about 1000%, less than or equal to about 500%, less than or equal to about 400%, less than or equal to about 200%, or less than or equal to about 100% of its initial length. Combinations of the above referenced ranges are also possible (e.g., between about 50% and about 1500%, between about hundred percent and about 1500%, between about 200% and about 1000%, between about 500% and about 1400%). Other ranges are also possible.

In certain embodiments, the enteric elastomer has an elastic modulus ranging between about 0.1 MPa and about 100 MPa. In some embodiments, the elastic modulus of the enteric elastomer is at least about 0.1 MPa, at least about 0.2 MPa, at least about 0.3 MPa, at least about 0.5 MPa, at least about 1 MPa, at least about 2 MPa, at least about 5 MPa, at least about 10 MPa, at least about 25 MPa, or at least about 50 MPa. In certain embodiments, the elastic modulus of the enteric elastomer is less than or equal to about 100 MPa, less than or equal to about 50 MPa, less than or equal to about 25 MPa, less than or equal to about 10 MPa, less than or equal to about 5 MPa, less than or equal to about 2 MPa, less than or equal to about 1 MPa, less than or equal to about 0.5 MPa, less than or equal to about 0.3 MPa, or less than or equal to about 0.2 MPa. Combinations of the above referenced ranges are also possible (e.g., between about 0.1 MPa and about 100 MPa, between about 0.3 MPa and about 10 MPa). Other ranges are also possible. Those skilled in the art would be capable of selecting suitable methods for determining the elastic modulus of an enteric elastomer including, for example, tensile mechanical characterization under ASTM D638 and/or compressive mechanical characterization under ASTM D575.

In certain embodiments, the enteric elastomer comprises varying ratios of poly(acryloyl-6-aminocaproic acid) and poly(methacrylic acid-co-ethyl acrylate). In some embodiments, the enteric elastomer is a polymer gel with water content no greater than 40%.

In some embodiments, the enteric elastomer comprises a polymer of a (meth)acryloylaminoalkylene acid monomer, or salts thereof. In certain embodiments, the (meth)acryloylaminoalkylene acid monomer is selected from the group consisting of acryloyl-5-aminopentanoic acid, acryloyl-6-aminocaproic acid, acryloyl-7-aminoheptanoic acid, acryloyl-8-aminooctanoic acid, acryloyl-9-aminononanoic acid, acryloyl-10-aminodecanoic acid, acryloyl-11-aminoundecanoic acid, acryloyl-12-aminododecanoic acid, methacryloyl-5-aminopentanoic acid, methacryloyl-6-aminocaproic acid, methacryloyl-7-aminoheptanoic acid, methacryloyl-8-aminooctanoic acid, methacryloyl-9-aminononanoic acid, methacryloyl-10-aminodecanoic acid, methacryloyl-11-aminoundecanoic acid, methacryloyl-12-aminododecanoic acid, salts thereof, and combinations thereof.

In certain embodiments, the enteric elastomer comprises a homopolymer of acryloyl-6-aminocaproic acid or salts thereof. In some embodiments, the enteric elastomer comprises a copolymer of acryloyl-6-aminocaproic acid or salts thereof. In certain embodiments, enteric elastomer comprises poly(methacrylic acid-co-ethyl acrylate) or salts thereof. In some cases, the poly(methacrylic acid-co-ethyl acrylate) has a molar ratio of methacrylic acid monomer units to ethylacrylate monomer units of about 1:1.

In some embodiments, the enteric elastomer is a blend. For example, in certain embodiments, the enteric elastomer comprises a first enteric polymer (e.g., poly(acryloyl-6-aminocaproic acid)) and a second enteric polymer (e.g., poly(methacrylic acid-co-ethyl acrylate)). In some such embodiments, the weight ratio of the first enteric polymer to the second enteric polymer ranges from about 1:0 to about 1:3 (e.g., between about 1:0 to about 1:3).

As described above, in some embodiments, the residence article, arm(s), and/or second component (e.g., elastic core) are coupled. Those skilled in the art would understand that the term coupled generally refers to a physical linkage connecting two or more components. In some embodiments, the residence article and second component may be coupled via an adhesive, by chemical interactions, and/or by interpenetrating (e.g., entangled) polymer chains. For example, in some embodiments, at least a portion of the residence article and at least a portion of the second polymeric component are coupled via a bond such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups.

In certain embodiments, the residence article and the second component are coupled via an adhesive (e.g., a biocompatible adhesive). Non-limiting examples of suitable adhesives include biocompatible polyurethanes and electroactive adhesives.

According to some embodiments, the residence article is configured to degrade, dissolve, and/or disassociate into one or more forms capable of passing through a gastrointestinal tract. In some embodiments, the residence article comprises one or more linkers designed for controlled and/or tunable degradation. According to some embodiments, one or more linkers are attached to and/or incorporated into the residence article to separate out in a modular fashion the function of delivering therapeutic, diagnostic, and/or enhancement agents from controlling (e.g., triggering) and/or tuning degradation.

In certain embodiments, the second component (e.g., elastic core) and one or more arms are coupled together via a linker.

The residence article may comprise one or more, two or more, or three or more types of linkers. For example, in an illustrative embodiment, the residence article comprises a first linker capable of degradation at a first average degradation rate and a second linker capable of degradation at a second average degradation rate. In certain embodiments, the linker degradation is pH dependent. In another illustrative embodiment, the residence article comprises a first linker capable of degradation under a first set of physiological conditions (e.g., in acidic pH such as in the stomach) and a second linker capable of degradation under a second set of physiological conditions different than the first set of physiological conditions (e.g., in relatively neutral pH such as in the intestines). In some embodiments, the second linker is not capable of substantial degradation under the first set of conditions. For example, in some cases, the second linker is not substantially degradable at a first physiological condition (e.g., in acidic pH such as in the stomach) and is capable of degradation at a second physiological condition different than the first set of physiological conditions.

The term physiological condition generally refers to a set of conditions of the external or internal milleu that may occur in an organism or cellular system (e.g., in contrast to laboratory conditions). For example, in some cases, a physiological condition ranges in temperature between about 20° C. and about 40° C. (e.g., between about 35° C. and about 38° C.) and/or atmospheric pressure of about 1 atm. In certain embodiments, the physiological conditions are that of an internal organ such as the stomach, intestines, bladder, lungs, and/or heart.

The linker may be selected such that the linker dissolves, degrades, mechanically weakens, and/or mechanically separates from at least one of the components (e.g., the residence article, the second component, an arm(s)) after a particular residence time period.

In an exemplary embodiment, the one or more linkers are selected to mediate disassembly of the residence article after, for example, delivery of an active substance for the residence time period (e.g., after about 24 hours, after about 48 hours, after about one week, after about one month), and safe passage through the lower intestinal tract of the subject. Exit from an orifice such as the gastric cavity may be achieved through changes in the mechanical properties of the linker (e.g., via biodegradation) such that the ability to resist passage through the orifice (or through the pylorus) is compromised, through breakage in the device through designed linker failure.

Several screening tests may be used to determine suitable materials for use as linkers, including but not limited to the ability to interface (e.g., couple) with at least a surface of the one or more components, mechanical strength sufficient to survive encapsulation, and mechanical strength sufficient to undergo the compressive forces present in physiological environments such as the gastric environment. In some embodiments, the linker is stable within a physiological environment such as the gastric environment for a period of time (e.g., a residence time period) of at least about 24 hours, at least about 48 hours, at least about one week, at least about one month, or least about one year.

In certain embodiments, the linker comprises a material such that, under relatively neutral pH physiological conditions (e.g., such as those in the duodenum), the linker can be mechanically broken (i.e. mechanical failure) by a tensile force less than or equal to about 2 N after about less than or equal to about 96 hours, less than or equal to about 48 hours, or less than or equal to about 24 hours under said neutral pH physiological conditions. In some embodiments, the mechanical failure occurs within the linker material itself, and not at the interface between the linker and the one or more polymeric components.

In some embodiments, the residence article comprises one or more configurations. For example, in certain embodiments, the residence article has a particular configuration such as a defined shape, size, orientation, and/or volume. The residence article may comprise any suitable configuration. In some embodiments, the residence article has a particular shape as defined by a cross-sectional area of the residence article. Non-limiting examples of suitable cross-sectional shapes include square, circles, ovals, polygons (e.g., pentagons, hexagons, heptagons, octagons, nonagons, dodecagons, or the like), tubes, rings, star or star-like (e.g., 3-armed stars, 4-armed stars, 5-armed stars, 6-armed stars, 7-armed stars, 8-armed stars), or the like. Those skilled in the art would be capable of selecting suitable shapes depending on the application (e.g., a star-like shape for gastric retention residence articles) and based upon the teachings of this specification.

The residence article may, in some cases, have an original configuration which may be modified (e.g., deformed) such that the residence article obtains a new configuration, different than the original configuration. For example, in some embodiments, the residence article has a first configuration and a second configuration, different than the first configuration.

In certain embodiments, the configuration of the residence article may be characterized by a largest cross-sectional dimension. In some embodiments, the largest cross-sectional dimension of the first configuration may be at least about 10% less, at least about 20% less, at least about 40% less, at least about 60% less, or at least about 80% less than the largest cross-sectional dimension of the second configuration. In certain embodiments, the largest cross-sectional dimension of the second configuration may be at least about 10% less, at least about 20% less, at least about 40% less, at least about 60% less, or at least about 80% less than the largest cross-sectional dimension of the first configuration. Combinations of the above referenced ranges are also possible (e.g., between about 10% and about 80%, between about 10% and about 40%, between about 20% and about 60%, between about 40% and about 80%). Other ranges are also possible.

In some embodiments, the configuration of the residence article may be characterized by a convex hull volume of the residence article. The term convex hull volume is known in the art and generally refers to a set of surfaces defined by the periphery of a 3-D object such that the surfaces define a particular volume. In some embodiments, the convex hull volume of the first configuration may be at least about 10% less, at least about 20% less, at least about 40% less, at least about 60% less, or at least about 80% less than the convex hull volume of the second configuration. In certain embodiments, the convex hull volume of the second configuration may be at least about 10% less, at least about 20% less, at least about 40% less, at least about 60% less, or at least about 80% less than the convex hull volume of the first configuration. Combinations of the above referenced ranges are also possible (e.g., between about 10% and about 80%, between about 10% and about 40%, between about 20% and about 60%, between about 40% and about 80%). Other ranges are also possible.

Those skilled in the art would understand that the differences between the first configuration and the second configuration do not refer to a swelling or a shrinking of the residence article (e.g., in the presence of a solvent), but instead refers to a change in shape and/or orientation of at least a portion of the residence article (e.g., in the presence of a stimulus such as heat), although some degree of swelling or shrinking may occur between the two configurations.

In some embodiments, the first configuration is constructed and arranged such that a residence article is retained at a location internal of a subject, and the second configuration is constructed and arranged such that the residence article may be encapsulated (e.g., for oral delivery of the residence article within a capsule). In some cases, the first configuration is sufficiently large such that the residence article is retained at a location internal of the subject and the second configuration is sufficiently small such that the residence article may fit within a particular size capsule suitable for oral delivery to a subject.

In certain embodiments, the residence article may be polymerized, printed (e.g., 3D printed) and/or cast in a first configuration, mechanically deformed such that the residence article obtains a second configuration, and placed in a capsule. The residence article may be mechanically deformed using any suitable method including, for example, bending, twisting, folding, molding (e.g., pressing the material into a mold having a new shape), expanding (e.g., applying a tensile force to the material), compressing, and/or wrinkling the residence article. The residence article may maintain the second configuration for any suitable duration. Advantageously, the residence articles described herein may be relatively stable in the first and/or second configurations such that the residence article may be stored for long periods of time without significant degradation of mechanical properties of the one or more components and/or one or more linkers. In some embodiments, the residence article may be stable under ambient conditions (e.g., room temperature, atmospheric pressure and relative humidity) and/or physiological conditions (e.g., at or about 37° C., in physiologic fluids) for at least about 1 day, at least about 3 days, at least about 7 days, at least about 2 weeks, at least about 1 month, at least about 2 months, at least about 6 months, at least about 1 year, or at least about 2 years. In certain embodiments, the residence article has a shelf life of less than or equal to about 3 years, less than or equal to about 2 years, less than or equal to about 1 year, less than or equal to about 1 month, less than or equal to about 1 week, or less than or equal to about 3 days. Combinations of the above-referenced ranged are also possible (e.g., between about 24 hours and about 3 years, between about 1 week and 1 year, between about 1 year and 3 years). Other ranges are also possible.

In some embodiments, the residence article in the second configuration may recoil such that the residence article reverts to the first configuration. For example, in some embodiments, the residence article in the second configuration is contained within a capsule and delivered orally to a subject. In some such embodiments, the residence article may travel to the stomach and the capsule may release the residence article, upon which the residence article obtains the first configuration.

As described herein, in some embodiments, the residence article may comprise one or more components with particular mechanical properties such that the residence article will substantially recoil after being mechanically deformed (e.g., an elastic core). The residence article may be characterized, in some cases, by a folding force. The term folding force generally refers to the force required to compress the residence article into a cavity having a cross-sectional area of less than about 2 cm (e.g., such as the pylorus). In some embodiments, the folding force of the residence article is at least about 0.2 N, at least about 0.5 N, at least about 0.7 N, at least about 1 N, at least about 1.5 N, at least about 2 N, at least about 2.5 N, or at least about 3 N. In certain embodiments, the folding force of the residence article is less than or equal to about 5 N, less than or equal to about 3 N, less than or equal to about 2.5 N, less than or equal to about 2 N, less than or equal to about 1.5 N, less than or equal to about 1 N, less than or equal to about 0.7 N, or less than or equal to about 0.5 N. Combinations of the above-referenced ranges are also possible (e.g., between about 0.2 N and about 3 N, between about 0.2 N and about 2.5 N, between about 0.5 N and about 1.5N, between about 1 N and about 3 N). Other ranges are also possible. The folding force may be determined by, for example, by placing the residence article in a funnel having a 20 cm upper diameter and a 2 cm lower diameter (e.g., simulating the pyloric sphincter) and measuring the forces required to move the residence article through the 2 cm lower diameter. A plunger may be attached to the tension cross-head of an tensile loading machine and the funnel to a clamp, and the residence article pushed through the funnel at a rate of, for example, 10 mm/min, which measuring the force and displacement. The folding force is generally determined by measuring the force at which the residence article folds and enters the 2 cm lower diameter tube.

In certain embodiments, the residence article in the first configuration has a minimum uncompressed cross-sectional dimension. The minimum uncompressed cross-sectional dimension is generally selected such that the residence article is retained at a location internally to a subject for a relatively long period of time (e.g., at least about 24 hours) even under physiological compressive forces (e.g., such as those in the digestive tract).

In some embodiments, the minimum uncompressed cross-sectional dimension of the first configuration is at least about 2 cm, at least about 4 cm, at least about 5 cm, or at least about 10 cm. In certain embodiments, the minimum uncompressed cross-sectional dimension of the first configuration is less than or equal to about 15 cm, less than or equal to about 10 cm, less than or equal to about 5 cm, or less than or equal to about 4 cm. Combinations of the above-referenced ranges are also possible (e.g., between about 2 cm and about 15 cm). Those skilled in the art would be capable of selecting suitable minimum uncompressed cross-sectional dimensions for residence articles based upon the teachings of this specification for specific orifices of a subject such that the residence article is retained.

As described herein, in some embodiments, the one or more components of the residence article may be cast, molded, 3D printed, and/or cut to have a particular shape, size, and/or volume.

In an exemplary embodiment, a shape capable of residence (e.g., being retained in an orifice at a particular location internal to a subject) such as gastric residence comprises a three-dimensional structure having a plurality of projections (i.e. arms). In some embodiments, the structure with projections comprises a flexible material capable of elastic (non-plastic) deformation. The projections themselves may be flexible or rigid with flexible connections to a core. In some embodiments, one or more controlled degradation linkers (e.g., enteric elastomers) are attached to and/or incorporated into the structure, for example, along one or more projections, preferably near or at the connection to a core. In some embodiments, each projection has a length equal to just less than the length of a soluble container such that the unencapsulated final form has a diameter equal to nearly twice the soluble container length. In some embodiments, the projections each have a length of about 0.5 cm to about 2.5 cm (e.g., such that the residence article has a minimum uncompressed cross-sectional dimension of at least about 2 cm).

In certain embodiments, the projections are arranged based on bio-inspired flower bud designs in which a number (N) of radial spokes or petals project from a central linking core. In some embodiments, these radial projections each have an internal sector angle of approximately 360°/N, where N is the total number of radial projections. In some cases, this maximizes the packing volume of the encapsulated structure, thus maximizing drug carrying capacity. In some embodiments, the projections are formed of a material with a relatively high elastic modulus to increase the resistance to compression and duration of gastric residence, as described herein.

According to some embodiments, a shape capable of residence (e.g., being retained in an orifice at a particular location internal to a subject) such as a gastric residence comprises a three-dimensional structure forming a polygon outline with, for example, 3, 4, 6, 8, 10, 12, 14, 16, 18, or 20 sides, when projected onto a flat surface. In some embodiments, each side has a length equal to just less than the length of a soluble container. In some embodiments, the structure comprises a flexible material capable of elastic (non-plastic) deformation such that the structure is capable of bending at its vertices and packing into a soluble container. Materials with low elastic moduli, with low creep deformation and/or good recoil, and capable of large elastic deformation may be used at the vertices to facilitate stable packing. In some embodiments, individual sides each have an internal sector angle of approximately 360°/N, where N is the total number of sides, to obtain maximal packing.

As described herein, in some embodiments, the residence article is configured to adopt a shape and/or size compatible with oral administration to and/or ingestion by a subject. In some embodiments, the residence article has a shape with a capacity for folding and/or packing into stable encapsulated forms. For example, in some embodiments the residence article is designed to maximally pack and fill a capsule or other soluble container (e.g., a containing structure). In some embodiments, the residence article has a shape that maximally fills and/or packs into a capsule or other soluble container.

In some embodiments, the system comprises the residence article and a containing structure. Based on the application, a capsule may be manufactured to particular specifications or a standard size, including, but not limited to, a 000, 00, 0, 1, 2, 3, 4, and 5, as well as larger veterinary capsules Su07, 7, 10, 12e1, 11, 12, 13, 110 ml, 90 ml, and 36 ml. In some embodiments, the residence article may be provided in capsules, coated or not. The capsule material may be either hard or soft, and as will be appreciated by those skilled in the art, typically comprises a tasteless, easily administered and water soluble compound such as gelatin, starch or a cellulosic material.

In other embodiments, the residence article is retained in a packed shape by a soluble retaining element, such as a band or surgical thread. In some embodiments, the residence article comprises optimal combinations of materials with high and low elastic moduli, giving the residence article the capacity to alter its shape and/or size once the soluble container and/or soluble retaining element is removed.

In some embodiments, the residence articles are configured for transesophageal administration, transesophageal retrieval, and/or gastric retention to/in a subject. In some embodiments, the residence articles described herein may comprise relatively high levels of drug loading and stability (e.g., greater than or equal to 1 gram), obtain gastric retention for relatively long periods of time, provide long term alcohol sensing, and/or may be compatible with a broad range of drug classes. In certain embodiments, the residence article includes dimensions configured for transesophageal administration with a gastric resident system. In some cases, the residence article may be configured to control drug release e.g., with zero-order drug kinetics with no potential for burst release for weeks to months. In some embodiments, the residence articles described herein comprise biocompatible materials and/or are safe for gastric retention. In certain embodiments, the residence article includes dimensions configured for transesophageal retrieval. In some cases, the residence articles described herein may comprise relatively large doses of drug (e.g., greater than or equal to 1 gram).

In some embodiments, the residence article comprises a polymer matrix (e.g., comprising a polymeric material) and a therapeutic agent associated with the polymer matrix. For example, as illustrated in FIG. 1, exemplary article 100 comprises additional component 120 comprising a polymer matrix. In certain embodiments, a hollow core may be disposed within the polymer matrix. In some embodiments, the hollow core disposed within the polymeric matrix is configured to receive an elastic wire.

In certain embodiments, a therapeutic agent is disposed within the polymer matrix. In some embodiments, the therapeutic agent is adjacent the polymer matrix. As used herein, when a component is referred to as being "adjacent" another component, it can be directly adjacent to (e.g., in contact with) the component, or one or more intervening components also may be present. A component that is "directly adjacent" another component means that no intervening component(s) is present. In some cases, the therapeutic agent may be directly adjacent the polymer matrix (e.g., as a layer deposited on the polymer matrix).

In some embodiments, the polymer matrix comprises a plurality of holes (e.g., microdrilled holes in the polymer matrix). In some embodiments, the plurality of holes have an average diameter of greater than or equal to 0.1 mm, greater than or equal to 0.2 mm, greater than or equal to 0.5 mm, greater than or equal to 0.7 mm, greater than or equal to 0.8 mm, or greater than or equal to 0.9 mm. In certain embodiments, the plurality of holes have an average diameter of less than or equal to 1 mm, less than or equal to 0.9 mm, less than or equal to 0.7 mm, less than or equal to 0.5 mm, or less than or equal to 0.2 mm. Combinations of the above-referenced ranges are also possible (e.g., greater than or equal to 0.1 mm and less than or equal to 1 mm). Other ranges are also possible.

In certain embodiments, the polymeric matrix comprises a polymeric material. In some embodiments, the polymeric material is selected from the group consisting of vinylpolysiloxane, polydimethylsiloxane, polycaprolactone, polyethylene, polyethylene-vinyl acetate, methylcellulose, hydroxypropylmethylcellulose, hydroxypropylcellulose, hydroxyethylcellulose, ethylhydroxyethylcellulose, sodium-carboxymethylcellulose, ethylcellulose, hypromellose acetate succinate, cellulose acetate, cellulose acetate propionate, and combinations thereof.

The polymeric material may have any suitable Young's elastic modulus. In some embodiments, the Young's elastic modulus of the polymeric material is less than or equal to 10 MPa, less than or equal to 8 MPa, less than or equal to 6 MPa, less than or equal to 4 MPa, less than or equal to 2 MPa, less than or equal to 1 MPa, or less than or equal to 0.8 MPa. In certain embodiments, the Young's elastic modulus of the polymeric material is greater than or equal to 0.5 MPa, greater than or equal to 0.8 MPa, greater than or equal to 1 MPa, greater than or equal to 2 MPa, greater than or equal to 4 MPa, greater than or equal to 6 MPa, or greater than or equal to 8 MPa. Combinations of the above-referenced ranges are also possible (e.g., greater than or equal to 0.1 MPa and less than or equal to 10 MPa). Other ranges are also possible.

In some embodiments, the residence article is selected to have a particular diameter e.g., suitable for transesophageal administration and/or transesophageal retrieval. In some embodiments, the residence article has a diameter of less than or equal to 20 mm, less than or equal to 15 mm, less than or equal to 10 mm, less than or equal to 8 mm, less than or equal to 6 mm, less than or equal to 4 mm, or less than or equal to 2 mm. In certain embodiments, the residence article has a diameter of greater than or equal to 1 mm, greater than or equal to 2 mm, greater than or equal to 4 mm, greater than or equal to 6 mm, greater than or equal to 8 mm, greater than or equal to 10 mm, or greater than or equal to 15 mm. Combinations of the above-referenced ranges are also possible (e.g., greater than or equal to 1 mm and less than or equal to 10 mm, greater than or equal to 1 mm and less than or equal to 20 mm). Other ranges are also possible.

In some embodiments, the residence article may have a particular maximum dimension (e.g., length) e.g., suitable for transesophageal administration and/or transesophageal retrieval. In some embodiments, the maximum dimension of the residence article is greater than or equal to 5 mm, greater than or equal to 8 mm, greater than or equal to 10 mm, greater than or equal to 15 mm, greater than or equal to 20 mm, greater than or equal to 25 mm, greater than or equal to 50 mm, greater than or equal to 100 mm, greater than or equal to 250 mm, greater than or equal to 500 mm, or greater than or equal to 750 mm. In certain embodiments, the maximum dimension of the residence article is less than or equal to 1000 mm, less than or equal to 750 mm, less than or equal to 500 mm, less than or equal to 250 mm, less than or equal to 100 mm, less than or equal to 50 mm, less than or equal to 25 mm, less than or equal to 20 mm, less than or equal to 15 mm, less than or equal to 10 mm, or less than or equal to 8 mm. Combinations of the above-referenced ranges are also possible (e.g., greater than or equal to 5 mm and less than or equal to 1000 mm). Other ranges are also possible.

In some embodiments, the residence article may comprise a coating (e.g., to reduce or eliminate the burst release of a drug from the surface of the residence article). In some cases, the coating is adjacent (e.g., directly adjacent) the polymer matrix. In certain embodiments, the coating is selected from the group consisting of Eudragit RS PO, Eudragit NM 30D, polycaprolactone, ethylcellulose, cellulose acetate, cellulose acetate butyrate, polydimethysiloxane, polivinylacetate, and vinylpolysiloxane. Other coatings are also possible.

In certain embodiments, the residence article may comprise an excipient. In some cases, the excipient may be used to tune (e.g., change) the release rate of the drug (e.g., as compared to an article without such excipient). In some embodiments, the excipient comprises polyethylene glycol and/or silicone oil. In some cases, the polyethylene glycol has a number average molecular weight of greater than or equal to 300 g/mol and less than or equal to 500,000 g/mol (e.g., greater than or equal to 400 g/mol and less than or equal to 3,350 g/mol, greater than or equal to 400 g/mol and less than or equal to 200,000 g/mol, greater than or equal to 3,350 g/mol and less than or equal to 200,000 g/mol). Other ranges are also possible.

In some embodiments, a magnetic component (e.g., a magnet) may be associated with an end (e.g., an end surface) of the residence article. Suitable magnetic materials include, for example, aluminum nickel cobalt alloys, ferrites, and neodymium-based materials. Such magnetic components may be useful for, for example, retrieval of the residence article (e.g., from a location internal to the subject). In certain embodiments, the residence article comprises a hollow core. In certain embodiments, the hollow core is configured to receive an elastic wire (e.g., comprising nitinol). In some embodiments, the elastic wire comprises a superelastic alloy and/or shape memory material.

According to some embodiments, the residence articles described herein are compatible with one or more therapeutic, diagnostic, and/or enhancement agents, such as drugs, nutrients, microorganisms, in vivo sensors, and tracers. In some embodiments, the active substance, is a therapeutic, nutraceutical, prophylactic or diagnostic agent. While much of the specification describes the use of therapeutic agents, other agents listed herein are also possible.

In a particular set of embodiments, the therapeutic agent is selected from the group consisting of doxycycline hyclate, moxifloxacin, pyrazinamide, ethambutol, isoniazid, rifampicin, Streptomycin, moxifloxacin, interferon, peginterferon, ribavirin, paritaprevir, simepravir, grazoprevir, ladispavir, ombitasvir, elbasavir, daclatasvir, and sofosbuvir. Other therapeutic agents are also possible. For example, agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals.

Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, nonsteroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, anti (retro)viral agents like entecavir, dolutegravir, rilpivirine, and cabotegravir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In certain embodiments, the active substance is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents, antihistamines, antimigraine drugs, hormones, prostaglandins, antimicrobials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery article. These may be vitamins, supplements such as calcium or biotin, or natural ingredients such as plant extracts or phytohormones.

In another embodiment, the therapeutic agent is an immunosuppressive agent. Exemplary immunosuppressive agents include glucocorticoids, cytostatics (such as alkylating agents, antimetabolites, and cytotoxic antibodies), antibodies (such as those directed against T-cell receptors or 11-2 receptors), drugs acting on immunophilins (such as cyclosporine, tacrolimus, and sirolimus) and other drugs (such as interferons, opioids, TNF binding proteins, mycophenolate, and other small molecules such as fingolimod).

In some embodiments, the therapeutic agent is a small molecule drug having molecular weight less than about 2500 Daltons, less than about 2000 Daltons, less than about 1500 Daltons, less than about 1000 Daltons, less than about 750 Daltons, less than about 500 Daltons, less or than about 400 Daltons. In some cases, the therapeutic agent is a small molecule drug having molecular weight between 200 Daltons and 400 Daltons, between 400 Daltons and 1000 Daltons, or between 500 Daltons and 2500 Daltons.

In certain embodiments, the therapeutic agent is present in the residence article in an amount greater than or equal to 1 gram, greater than or equal to 2 grams, greater than or equal to 3 grams, greater than or equal to 5 grams, greater than or equal to 10 grams, greater than or equal to 20 grams, greater than or equal to 30 grams, greater than or equal to 40 grams, greater than or equal to 50 grams, greater than or equal to 60 grams, greater than or equal to 70 grams, or greater than or equal to 80 grams, greater than or equal to 90 grams. In some embodiments, the therapeutic agent is present in the residence article in an amount of less than or equal to 100 grams, less than or equal to 90 grams, less than or equal to 80 grams, less than or equal to 70 grams, less than or equal to 60 grams, less than or equal to 50 grams, less than or equal to 40 grams, less than or equal to 30 grams, less than or equal to 20 grams, less than or equal to 10 grams, less than or equal to 5 grams, less than or equal to 3 grams, or less than or equal to 2 grams. Combinations of the above-referenced ranges are also possible (e.g., greater than or equal to 1 gram and less than or equal to 100 grams, greater than or equal to 2 grams and less than or equal to 100 grams, greater than or equal to 3 grams and less than or equal to 100 grams). Other ranges are also possible.

In some embodiments, the residence articles described herein comprises two or more types of therapeutic agents. For example, in some embodiments, a first therapeutic agent and a second therapeutic agent are present in the residence article such that the total amount of the first and second therapeutic agent is in one or more ranges described above (e.g., the total amount of therapeutic agent is greater than or equal to 1 gram and less than or equal to 100 grams). In some embodiments, each therapeutic agent is present in an amount such that the total amount of therapeutic agents is greater than or equal to 1 gram. In some embodiments, each therapeutic agent is present in an amount as described above (e.g., each therapeutic agent is present in an amount of greater than or equal to 1 gram and less than or equal to 100 grams).

In certain embodiments, the therapeutic agent is present in the residence article at a concentration such that, upon release from the residence article, the therapeutic agent elicits a therapeutic response.

In some embodiments, a subject may demonstrate health benefits, e.g., upon administration of the residence article.

In some embodiments, the residence article comprises a polymer matrix (e.g., polymeric material) having a reconfigurable shape. For example, in some embodiments, the residence article has a first shape/configuration (e.g., an elongated (e.g., straight) shape) and, upon removal of an elastic wire, obtains a second shape/configuration (e.g., a coil), different than the first shape.

The polymer matrix may be reconfigured, in some cases, into a shape such as a straight shape, a J-hook shape, a spherical shape, a cylindrical shape, a coil shape, or a toroidal shape. Other shapes are also possible. In some embodiments, the polymeric material is reconfigured upon insertion or removal of an elastic wire (e.g., from a hollow core of the polymer matrix). In some embodiments, the reconfigured shape is such that the residence article may be retained (e.g., at a location internal to a subject) as described in more detail herein. In some embodiments, the reconfigured shape has dimension incompatible with passage through proximal and/or distal orifices of a containing viscus of a subject (e.g., such that the residence article is retained).

In some embodiments, the residence article has a maximum dimension (e.g., length when elongated) of greater than or equal to 20 cm, greater than or equal to 28 cm, greater than or equal to 30 cm, greater than or equal to 50 cm, greater than or equal to 100 cm, greater than or equal to 200 cm, or greater than or equal to 500 cm. In certain embodiments, the residence article has a maximum dimension of less than or equal to 1000 cm, less than or equal to 500 cm, less than or equal to 200 cm, less than or equal to 100 cm, less than or equal to 50 cm, less than or equal to 30 cm, or less than or equal to 28 cm. Combinations of the above-referenced ranges are also possible (e.g., greater than or equal to 20 cm and less than or equal to 1000 cm, greater than or equal to 20 cm and less than or equal to 200 cm). Other ranges are also possible.

In some embodiments, the residence article has a size and/or configuration such that the residence article does not fit inside a standard capsule (e.g., a capsule having a shape or size as described in the USP including, but not limited to, 000 capsule, 00 capsule, 0 capsule, 1 capsule, 2 capsule, 3 capsule, 4 capsule, or 5 capsule). That is to say, in some embodiments, the residence article is not configured to be delivered in a capsule. As described herein, in some embodiments, the residence article is configured to be administered transesophageally.

In some embodiments, the shape of the polymeric material is configured to be reconfigured such that the residence article has a maximum overall diameter (e.g., in the second configuration) of greater than or equal to 2 cm, greater than or equal to 5 cm, greater than or equal to 10 cm, or greater than or equal to 25 cm. In certain embodiments, the shape of the polymeric material is configured to be reconfigured such that the residence article has a maximum overall diameter of less than or equal to 50 cm, less than or equal to 25 cm, less than or equal to 10 cm, or less than or equal to 5 cm. Combinations of the above-referenced ranges are also possible (e.g., greater than or equal to 2 cm and less than or equal to 50 cm, greater than or equal to 10 cm and less than or equal to 25 cm). Other ranges are also possible.

In certain embodiments, the residence article is configured to be retained at a location internal to a subject for a relatively long period of time. For example, in some embodiments, the residence article is retained at the location internal to the subject for at least about 1 day, at least about 3 days, at least about 7 days, at least about 2 weeks, at least about 1 month, at least about 2 months, at least about 6 months, at least about 1 year, or at least about 2 years. In certain embodiments, the residence article is retained at the location internal to the subject for less than or equal to about 3 years, less than or equal to about 2 years, less than or equal to about 1 year, less than or equal to about 1 month, less than or equal to about 1 week, or less than or equal to about 3 days. Combinations of the above-referenced ranged are also possible (e.g., between about 24 hours and about 3 years, between about 1 week and 1 year, between about 1 year and 3 years). Other ranges are also possible.

In some embodiments, the residence article may be designed and configured to have a relatively low force of administration (e.g., the force required to administer the device through a nasogastric or endoscopic tube). In certain embodiments, the residence article has an administration force of less than or equal to 20 N, less than or equal to 10 N, less than or equal to 5 N, or less than or equal to 1 N. In some embodiments, the residence article has an administration force of greater than or equal to 0.1 N, greater than or equal to 1 N, greater than or equal to 5 N, or greater than or equal to 10 N. Combinations of the above-referenced ranges are also possible (e.g., greater than or equal to 0.1 N and less than or equal to 20 N). Other ranges are also possible.

In some embodiments, the polymeric material may be encapsulated (e.g., by an elastomeric hollow tube).

In some embodiments, the location internally of the subject is the colon, the duodenum, the ileum, the jejunum, the stomach, or the esophagus.

Retrieval systems and related methods (e.g., for gastric resident articles) are also provided. In some embodiments, the retrieval system is configured to be administered transesophageally to a location internal to a subject such that a gastric residence system (e.g., one or more articles and/or components described herein), located at the location internal to the subject, may be retrieved (e.g., removed from the subject). Advantageously, the systems described herein may be small enough to be fit through the esophagus of a subject to non-invasively access the stomach and/or may be operated without the use of endoscopy and/or imaging (e.g., x-ray imaging). In some cases, the systems described herein may be configured to sense (e.g., via a sensor associated with the system) one or more gastric resident devices present in the subject. In some embodiments, upon detection of the gastric resident system, the retrieval system outputs a contact signal (e.g., via the sensor) such that a user may retrieve the device. In certain embodiments, the system may be configured to contact and bind with the gastric resident system (e.g., while able to hold the weight of the gastric resident system and retrieve it through the esophagus of the subject).

In some embodiments, the system comprises a polymeric component having a flexible member and a binding component associated with an end portion of the polymeric component. In some embodiment, the polymeric component comprises a flexible tube.

In some embodiments, the system may be administered transesophageally to a subject. In certain embodiments, the system comprises a sensor associated with an end portion of the polymeric component. In some cases, the sensor may be used to determine a distance between the binding component and the gastric residence system present at the location internal to the subject. The sensor may be, in some cases, adjacent (e.g., directly adjacent) an end portion of the polymeric component.

In some embodiments, upon administration of the retrieval system to the location internal to the subject, the retrieval system may interface, via a locking mechanism associated with an end portion of the polymeric component, with the gastric residence system. The locking mechanism may be, in some cases, adjacent (e.g., directly adjacent) an end portion of the polymeric component. In certain embodiments, after interfacing with the gastric residence system, the gastric residence system may be removed (e.g., via the retrieval system) from the location internal to the subject. In some embodiments, the system is configured to maintain contact (e.g., via the binding mechanism, via the locking mechanism) with the gastric residence system during extraction of said gastric residence system from a location internal to a subject.

In certain embodiments, the binding component comprises a magnet. In some such embodiments, the system is configured to magnetically associate (e.g., bind) with a gastric residence system.

In some embodiments, the binding component comprises a first species configured to interact with a second species via a binding event.

In some embodiments, the first species of the binding component interacts with a second species via formation of a bond, such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups. For example, the species may include a functional group, such as a thiol, aldehyde, ester, carboxylic acid, hydroxyl, and the like, wherein the functional group forms a bond with the nanodiamond particle. In some cases, the species may be an electron-rich or electron-poor moiety wherein interaction between the first species and the second species comprises an electrostatic interaction.

In some cases, the first species of the binding component may comprise a biological or a chemical group capable of binding another biological or chemical molecule. For example, the first species may include a functional group, such as a thiol, aldehyde, ester, carboxylic acid, hydroxyl, and the like, wherein the functional group forms a bond with the second species.

In some embodiments, the first species and the second species interact via a binding event between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of species include peptides, proteins, DNA, RNA, PNA. Other species and binding pairs are also possible.

In some embodiments, the sensor is configured to determine a distance between the binding component and the gastric residence system. For example, the sensor may be configured to determine, in some cases, the distance between a magnetic component associated with the retrieval system and a magnet associated with the gastric residence system. In a particular set of embodiments, the sensor is a Hall effect sensor. Other sensors are also possible.

As described above and herein, in some embodiments, the system comprises a locking mechanism (e.g., for anchoring the gastric residence system to the retrieval system). In certain embodiments, the locking mechanism comprises a snare. In some embodiments, the locking mechanism comprises a plurality of barbed features (e.g., barbs).

In some embodiments, the system is configured to pass through a nasogastric and/or endoscopic tube. For example, in certain embodiments, the system has a maximum diameter less than or equal to 7 mm, less than or equal to 6.5 mm, less than or equal to 6 mm, less than or equal to 5 mm, less than or equal to 4 mm, less than or equal to 3 mm, or less than or equal to 2.5 mm. In some embodiments, the system has a maximum diameter of greater than or equal to 2 mm, greater than or equal to 2.5 mm, greater than or equal to 3 mm, greater than or equal to 4 mm, greater than or equal to 5 mm, greater than or equal to 6 mm, or greater than or equal to 6.5 mm. Combinations of the above-referenced ranges are also possible (e.g., less than or equal to 7 mm and greater than or equal to 2 mm). Other ranges are also possible.

In some embodiments, the location internally of the subject is the colon, the duodenum, the ileum, the jejunum, the stomach, or the esophagus.

EXAMPLES

The following examples are intended to illustrate certain embodiments described herein, including certain aspects of the present invention, but do not exemplify the full scope of the invention.

Example 1

This example demonstrates a novel approach to monitor alcohol intake by placing a sensor directly in the gastrointestinal (GI) tract, which enables the access to ingested alcohol before it is metabolized by the body. Combining alcohol-sensing electronics with gastroretentive structures enables long-term, continuous, and real-time monitoring of daily alcohol use.

Substances use disorder (SUD) is a medical illness associated with compulsive and repeated use of addictive substances. SUDs lead to millions of premature deaths and is among the leading causes of disability world-wide in both developing and developed countries. Alcohol is one of the most widely misused substances and dominates major causes of public accidents and overuse-induced death 1. Based on the 2018 study by the Substance Abuse and Mental Health Services Administration, in the United States alone, there are more than 16 million heavy alcohol drinkers. However, only about 10% of those who needed treatment for SUDs received treatments in 2018. It is estimated that each year, over 88,000 people die from alcohol related causes[2,3].

As with management of all chronic diseases, treatment of alcohol use disorder generally relies on long-term quantitative and qualitative monitoring of alcohol intake. Given lack of accurate and readily available technology, the current standard is for patients to record and report long-term, continuous monitoring of their alcohol use. Biochemical measures of breath or blood alcohol concentrations have been the most common approach for healthcare practitioners to qualitatively and quantitively acquire the alcohol consumption. However, these can only provide indices of very recent consumption due to the rapid alcohol metabolism by the body. Biological assays of alcohol metabolites may provide valid indicators of recent heavy consumption, but cannot provide information about the quantity or frequency of drinking episodes. Furthermore, such testing needs to be ordered by a healthcare provider through a laboratory, rather than as point-of-care testing, introducing several barriers to quick identification of relapse or high-risk behavior, especially in patients who are unable or unwilling to seek medical care. Recent advancements in transdermal alcohol sensing technology are an exciting development in the field of alcohol use disorder. It can provide real-time feedback on alcohol consumption levels to individuals who are attempting to moderate and/or reduce their alcohol use over the course of hours to weeks. By providing objective information about alcohol consumption, transdermal alcohol sensors can improve accurate measurements of alcohol intake and enable patients and healthcare providers to more effectively treat alcohol use disorder. Although transdermal alcohol readings have been proven to be correlated with breath alcohol measurements, both technologies employ the body-metabolized alcohol signal to estimate the overall alcohol consumption. Such secondary information often leads to skewed results of the actual amount of consumed alcohol.

Ethanol Vapor Monitoring

Figure 3:
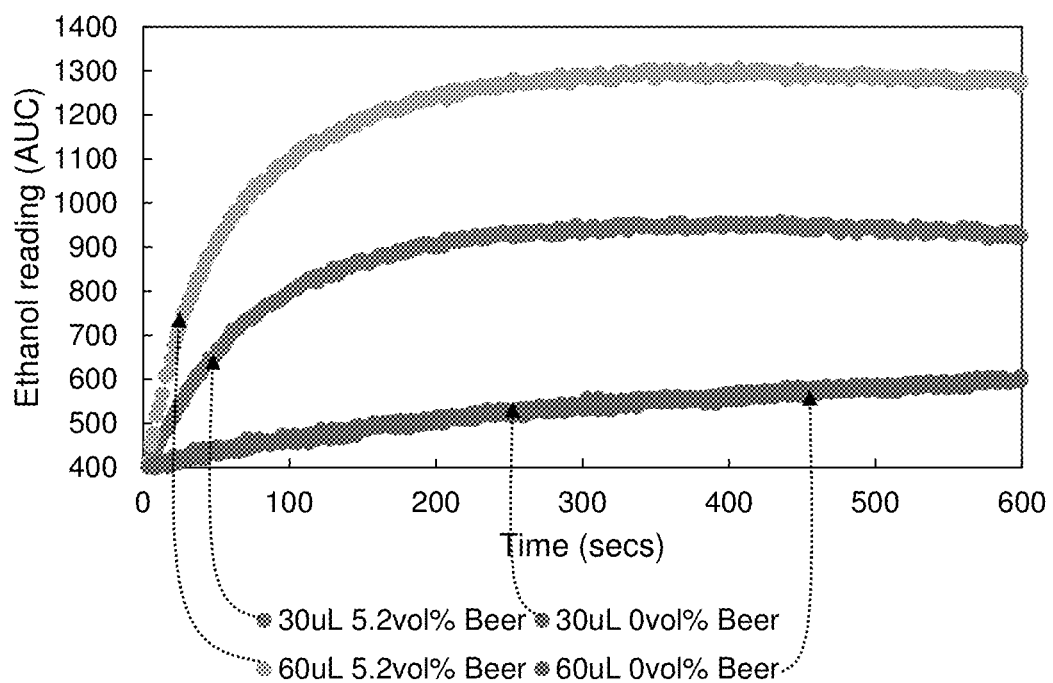
FIG. 3 shows ethanol vapor readings of alcoholic and non-alcoholic beverages with two different volume from a commercially available semiconductor volatile organic compound sensor, according to one set of embodiments.

To test whether the sensor can detect ethanol in alcoholic beverages, the sensor was placed in a vacuum chamber and controlled the inlet of ethanol vapor from a beer with a controlled volume. FIG. 3 shows that the sensor can differentiate the ethanol vapor from differing amounts of beer (30 µL vs. 60 µL). Additionally, the ethanol readings of non-alcoholic beverages are relatively weak compared to their alcoholic counterparts. Increasing the volume of non-alcoholic beverages from 30 µL to 60 µL does not change the ethanol reading, which further supports that there is no presence of ethanol vapor coming from the non-alcoholic beverage.

Figure 4:
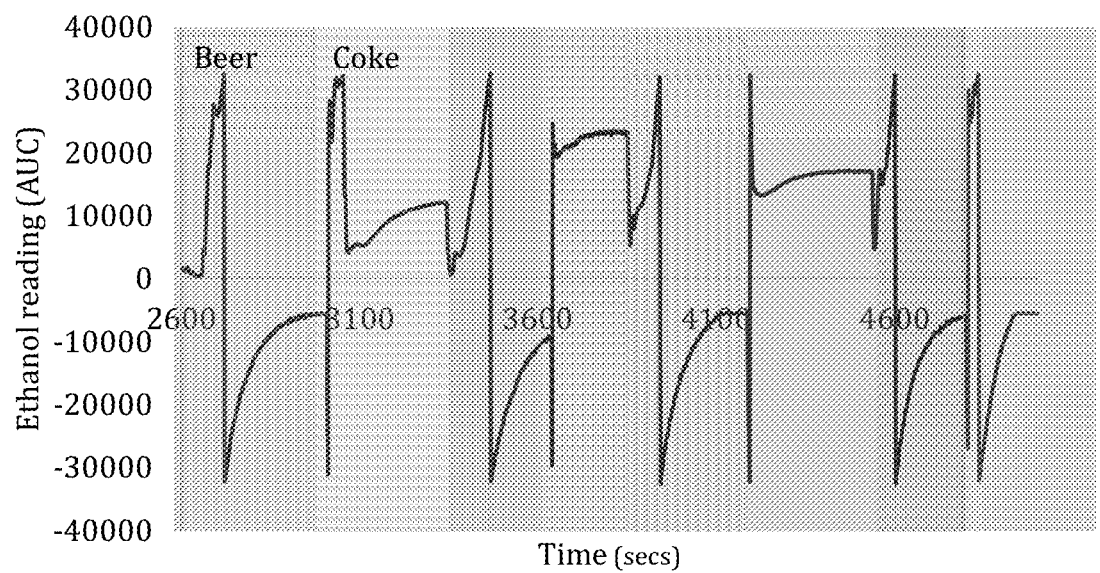
FIG. 4 shows ethanol vapor readings of beer and diet coke with higher volume input (800 µL), according to one set of embodiments.

FIG. 3 shows the sensor is able to detect the small amount of ethanol in 30 µL of 5.2 vol % beer. The ethanol reading is mostly proportional to the increase of ethanol vapor concentration. However, we observe a highly non-linear dynamic response of ethanol vapor readings at high concentrations that was not seen at low concentrations (FIG. 4). At a higher concentration of ethanol vapor, the ethanol reading first increases, then dramatically drops down to negative values, and then increases again with a negative steady state value. We repeatedly observe this pattern by adding the same amount of beer.

The SGP30 sensor is also designed to detect carbon dioxide. Beer contains a non-negligible amount of carbon dioxide; therefore, we wanted to test whether the ethanol sensor was actually detecting carbon dioxide rather than ethanol. In order to see how carbon dioxide affects the ethanol reading of beer, we used Diet Coke to generate carbon dioxide as a control model. We then alternately added beer and Diet Coke into the vacuum chamber (FIG. 4). The response patterns between ethanol and carbon dioxide are sufficiently different that we could develop an algorithm to differentiate them from each other.

Figure 5:
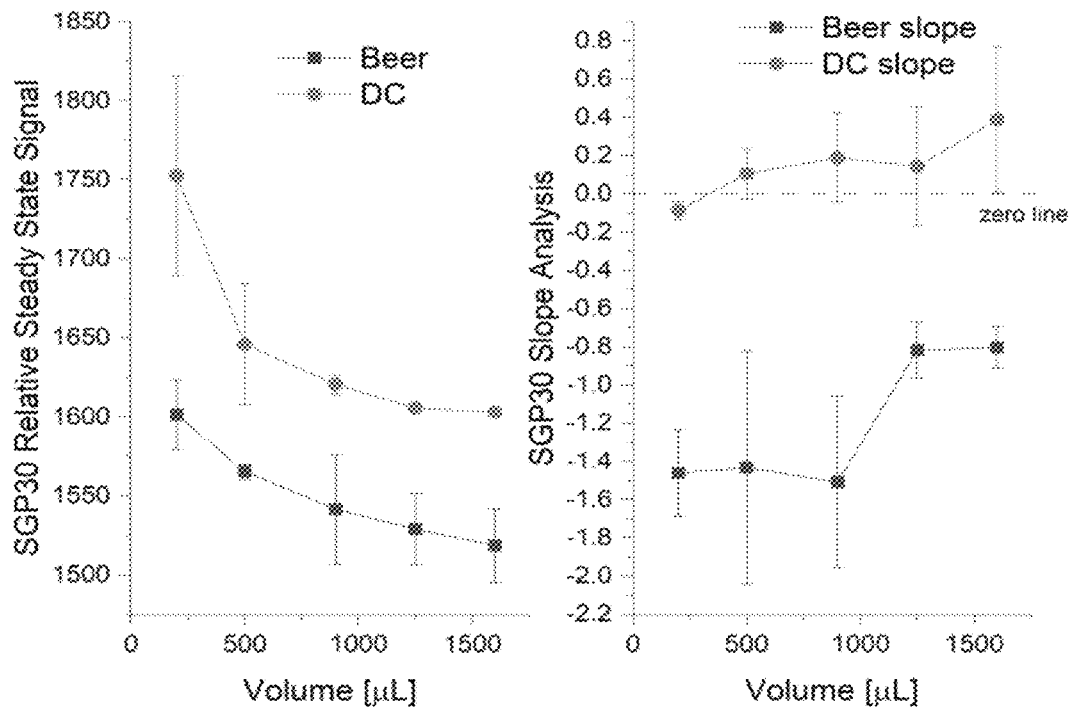
FIG. 5 shows a comparison of the slope and steady state signal with the standard error mean for SGP30 sensor for five distinct volumes (200 µL, 500 µL, 900 µL, 1250 µL, 1600 µL) of Diet Coke and beer, with three repetitions for each volume, according to one set of embodiments.

FIG. 5 shows the alcohol sensor is able to quantitatively detect various amounts of beer and differentiate from carbon dioxide-heavy drinks such as Diet Coke. The steady state signal of beer is significantly higher than that of Diet Coke. We also analyzed the linear fitting slope of the signals and found the slope of beer is usually about zero or greater than zero, while the slope of Diet Coke is always much lower than zero.

Sensor Immersing in Alcohol Beverages

Figure 6:
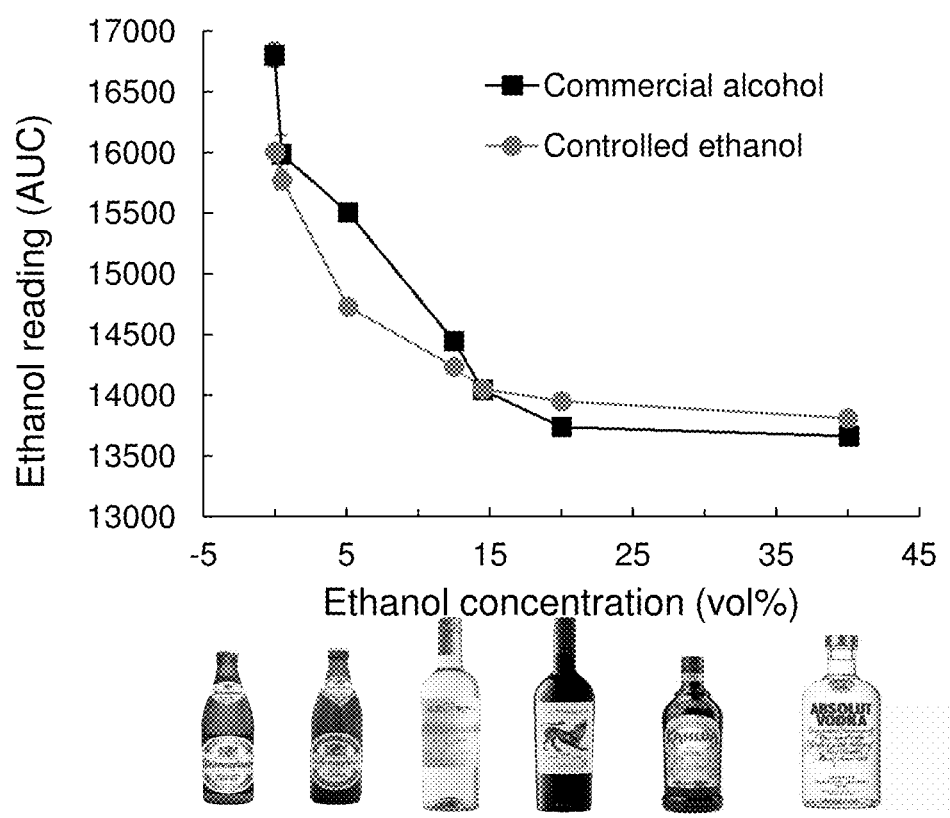
FIG. 6 shows ethanol readings of commercially available alcoholic beverages and their controlled counterparts with varying ethanol concentration. The sensor is fully immersed in the liquids.

The above-mentioned results demonstrate that the selected sensor, SGP30, is able to detect ethanol vapor. The motivation for developing an ingestible alcohol sensor is to take the advantage of the direct access of consumed alcohol in the GI tract. To do so, a filter membrane that allows only alcohol vapor to perfuse and isolates the electronics from the surrounding gastric fluids is mandatory. Silicone, PVDF, and PTFE based membranes have been shown to be ideal air permeable materials. We have tested the alcohol sensing performance of these three materials. They all show stable and robust results in detecting the existence of ethanol in in vitro experiments for a 1-week period without causing any fluidic leakage. To minimize the complexity of fabrication, we used silicone as the insulation and gas permeable material as it can easily achieve a conformal coating through a standard casting procedure. FIG. 6 shows the ethanol readings from the silicone sealed alcohol sensor with varying ethanol concentrations. The collected alcohol signal is wirelessly transmitted through radio frequency from the alcoholic liquid to an external receiver. A variety of ethanol concentrations are found in commercially available alcoholic beverages, such as beer (5.5%), red wine (12%), white wine (13%), Kahlua (20%), and Vodka (40%). The controlled alcohol concentrations were obtained by adding 99% ethanol into distilled (DI) water. The ethanol reading of the commercially available beverages and controlled alcoholic solutions with varying ethanol concentration showed similar trends.

Figure 7:
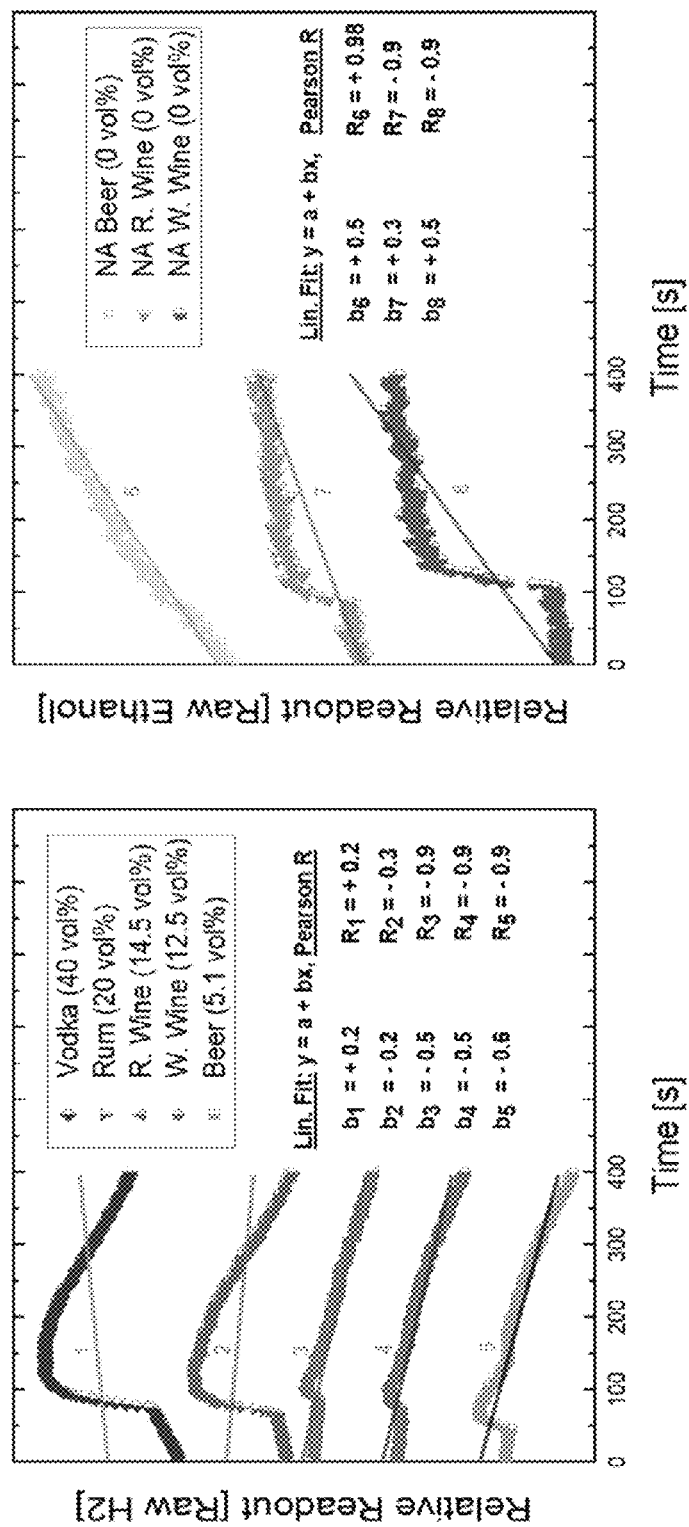
FIG. 7 shows a linear fit analysis of the ethanol reading in alcoholic (left) and non-alcoholic (right) beverages with various ethanol concentration, according to one set of embodiments.
Figure 8:
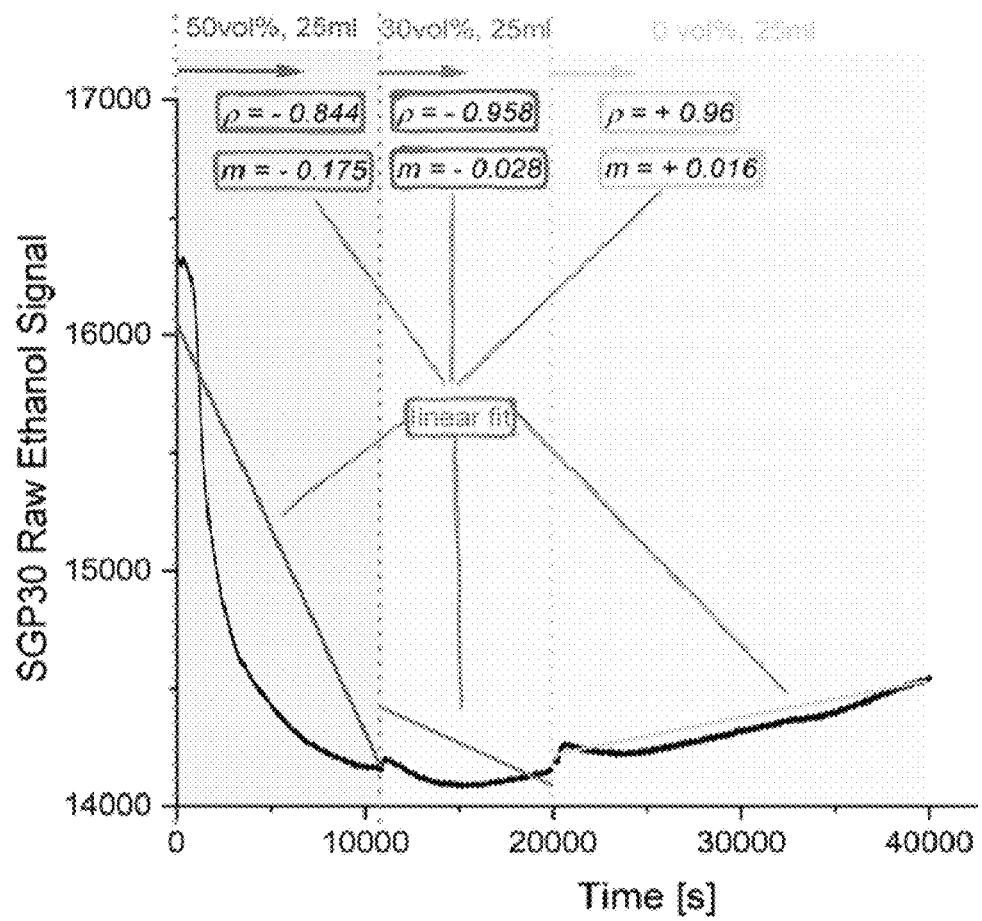
FIG. 8 shows long-term and dynamic response of the alcohol sensor in a complex environment simulated by alternately adding alcoholic and non-alcoholic liquid. Vol % represents the ethanol content of the added liquid; ml represents the total volume of added liquid, according to one set of embodiments.

FIG. 7 shows the dynamic response of ethanol signals from a variety of commercially available alcoholic drinks and non-alcoholic drinks. The dynamic patterns of alcoholic drinks are very different to those of non-alcoholic drinks. The signal pattern of alcoholic drinks consistently shows an initial step up response, and then gradually decreases toward or below the baseline value. In contrast, the non-alcoholic beer, red wine, and white wine showed an initial step up response, followed by a gradual increase rather than a decrease as in the alcoholic beverages. Additionally, the results of linear fitting show that alcoholic beverages usually produce a negative slope value, while their non-alcoholic counterparts produce a positive slope value. Thus, we can use this difference in dynamic response to identify the presence of ethanol in the GI tract. FIG. 8 shows the long-term ethanol reading of the sealed sensor immersed in DI water with different types of alcoholic and non-alcoholic beverages added in alternately. We apply the linear fitting algorithm in FIG. 8 and find that it can easily differentiate between alcoholic and non-alcoholic liquid.

Gastroretentive System with Alcohol Sensor

Figure 9:
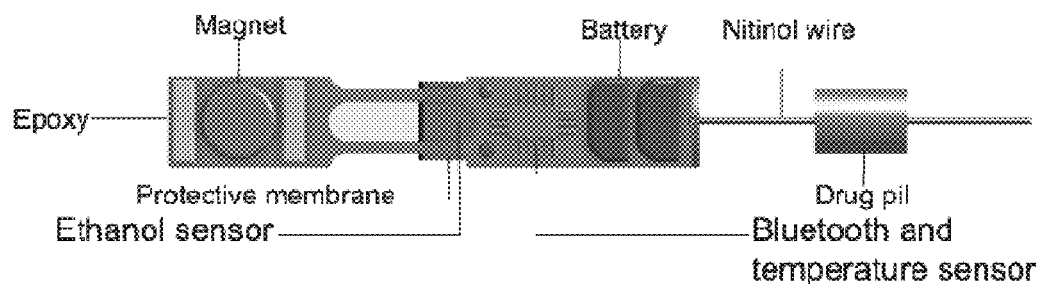
FIG. 9 shows in vivo preliminary result of ethanol detection in a large animal GI tract, according to one set of embodiments.
Figure 9:
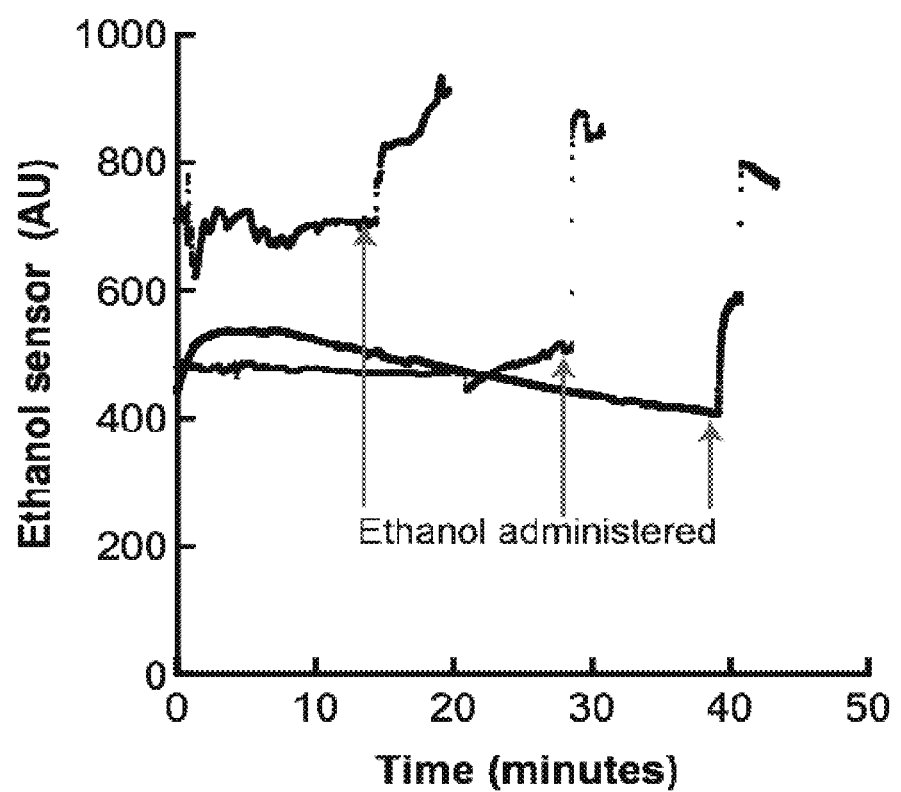

In this example two different types of gastroretentive systems were proposed, one administrated through a nasogastric tube and the other by ingestion. We integrate the silicone sealed alcohol sensor onto both gastroretentive systems to perform long-term, continuous, and real-time monitoring of alcohol intake. As a proof of concept, FIG. 9 shows a preliminary in vivo result of ethanol detection in the swine GI tract over a short period.

Example 2

The following example relates to the use of a long-acting direct-acting antiviral (LA-DAAS) which incorporates an alcohol sensor.

Hepatitis C virus infection (HCV) is one of the main causes of chronic liver disease worldwide. One forecast predicted that mortality from chronic hepatitis would exceed the mortality caused by HIV, TB, and malaria combined by 2040. Accordingly, the WHO has called for elimination of HCV infection by 2030.

Encouragingly, the development of direct-acting antiviral (DAA) therapy for HCV has revolutionized the field. The high cure rate of DAA therapies, with rates of sustained virologic response (SVR) of greater than 95%, short duration of treatment, and tolerability has greatly expanded the number of patients being cured of chronic HCV. However, due to factors such as cost, limited access to medical care, and inconsistent follow-up, less than half of those infected are actually treated. People who inject drugs (PWID) have especially low HCV treatment uptake, despite being a large reservoir for chronic HCV infection (50% of all PWID globally) and the leading population infected with acute HCV.

Particular challenges facing the PWID population include homelessness, which can make storage of oral medications difficult; comorbid psychiatric conditions; limited access to healthcare, and distrust of the medical system. Modeling studies have suggested that expanding treatment to PWID can reduce transmission of HCV, even with poor rates of adherence and SVR. Studies utilizing methadone programs to deliver HCV treatment show promise, with high rates of treatment completion and SVR.(3) However, such programs require significant infrastructure and cost, and do not capture PWID who do not engage in other opioid agonist therapies such as buprenorphine or may engage only intermittently. Challenges that all populations face with regards to oral therapies include forgetfulness, low priority, pill phobia, dysphagia, and pill burden; rates of adherence to chronic medications in general are at most 50%, though higher for short courses of therapy such as DAAs. Thus, there is a clear need for alternative strategies to deliver HCV treatment, and long-acting treatment delivery systems are one of the innovative strategies that have been endorsed, including recently by Unitaid.

A long-acting direct-acting antiviral system (LA-DAAS) has the potential to safely and consistently deliver DAA therapy to patients with good adherence and quality of life by decreasing the frequency of dosing, with the goal of ultimately providing single dosing. We have previously described a coil-shaped gastric resident system (GRS) which due to its dimensions and mechanical properties can remain resident in the gastric cavity and deliver multigram levels of drugs for tuberculosis, which has similar treatment challenges as HCV with frequent and daily dosing. Here, we describe the development of a LA-DAAS inspired by the multigram GRS with evaluation in a swine model for treatment of HCV. We developed additional features including integration of ethanol, temperature, and Bluetooth sensors to enable patient engagement via wireless communication with the LA-DAAS, as such tools have improved patient adherence to HCV therapy in other preliminary devices. We then evaluate the cost-effectiveness of the LA-DAAS in typical and PWID populations.

Results

Figures 10A, 10B, 10C, 10D:
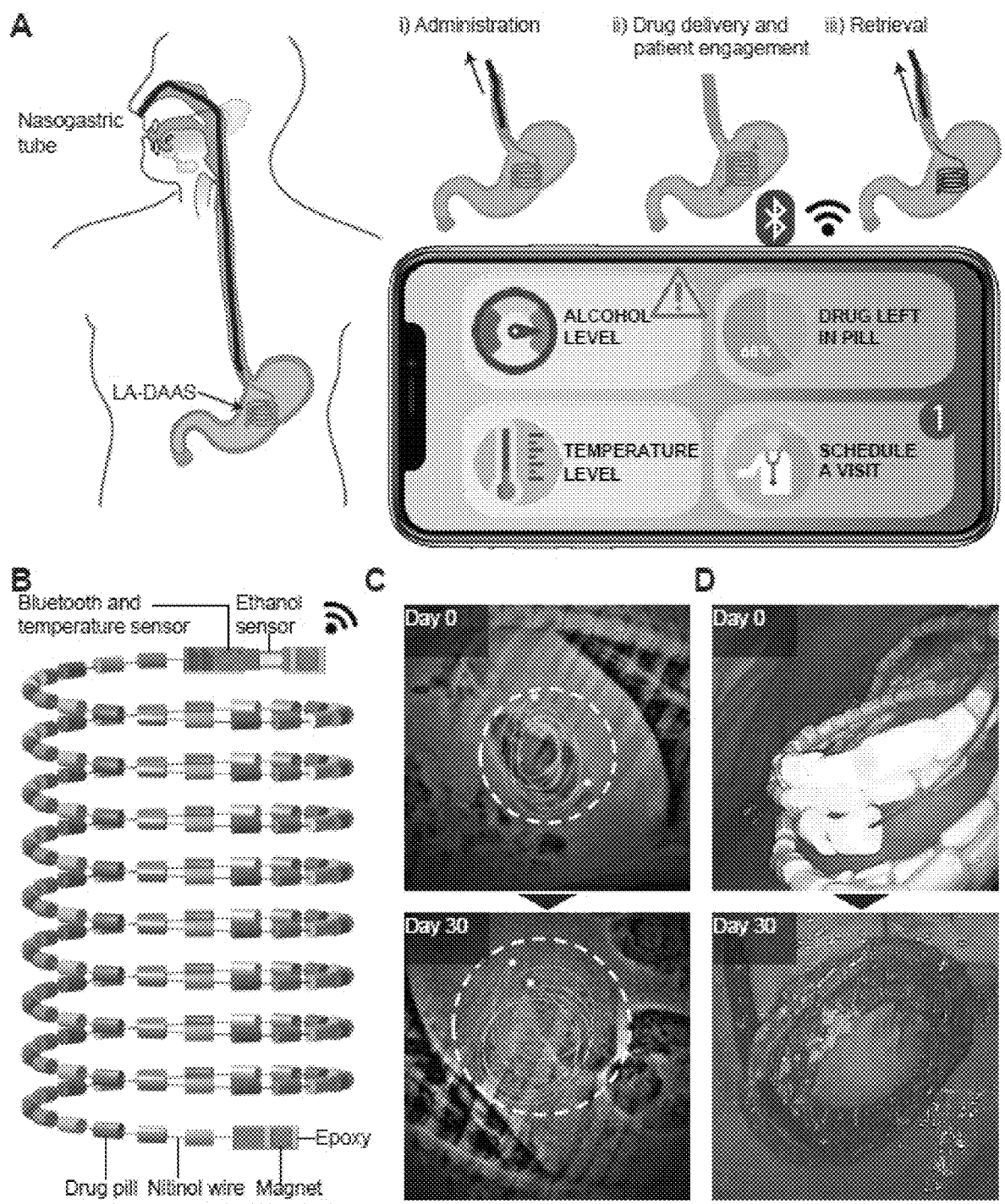
FIGS. 10A-10D show design and in vivo retention of the long-acting direct-acting antiviral system (LA-DAAS), according to one set of embodiments.

Design of the LA-DAAS. The LA-DAAS consists of drug-polymer pills strung along a superelastic nitinol wire.(22) It can be administered via a nasogastric tube and form a cylindrical coil upon reaching the stomach. During its residence in the gastric cavity, the LA-DAAS continually releases grams of drugs and is retrieved back through a nasogastric tube (FIGS. 10A-10B). Electronic sensors were added to each end of the LA-DAAS to provide information on alcohol intake, patient temperature, and to engage patients during their treatment. As alcohol use can cause further liver injury and accelerate disease progression, it is important for patients and clinicians to be aware of alcohol intake. However, patients may underestimate or underreport alcohol use due to stigma, and physicians frequently fail to screen adequately for excessive alcohol intake.(23, 24) An intragastric sensor can provide an objective measure of alcohol consumption and identify patients in need of therapy directed toward alcohol cessation.(23) Additionally, patients with chronic liver disease—particularly PWID with chronic liver disease—are at higher risk of infection. To this end, a temperature sensor was also incorporated into the LA-DAAS in order to alert patients and physicians of fever or hypothermia that may signal a serious infection. Finally, patient engagement with treatment has been shown to improve adherence.(20, 21, 25, 26) To this end, a Bluetooth and temperature sensor to confirm continual functional device status combined with a mobile software application was incorporated into the LA-DAAS. Messages could be sent to a patient's mobile device to remind them of clinic appointments or to return for repeat LA-DAAS administration and/or removal. In PWID or other high-risk populations where communication can be a challenge, such a built-in device could improve outreach to patients. The physical dimensions of the LA-DAAS can be personalized to each patient depending on the target drug load and duration of therapy (FIGS. 15A-15D).

Figures 16A, 16B, 16C:
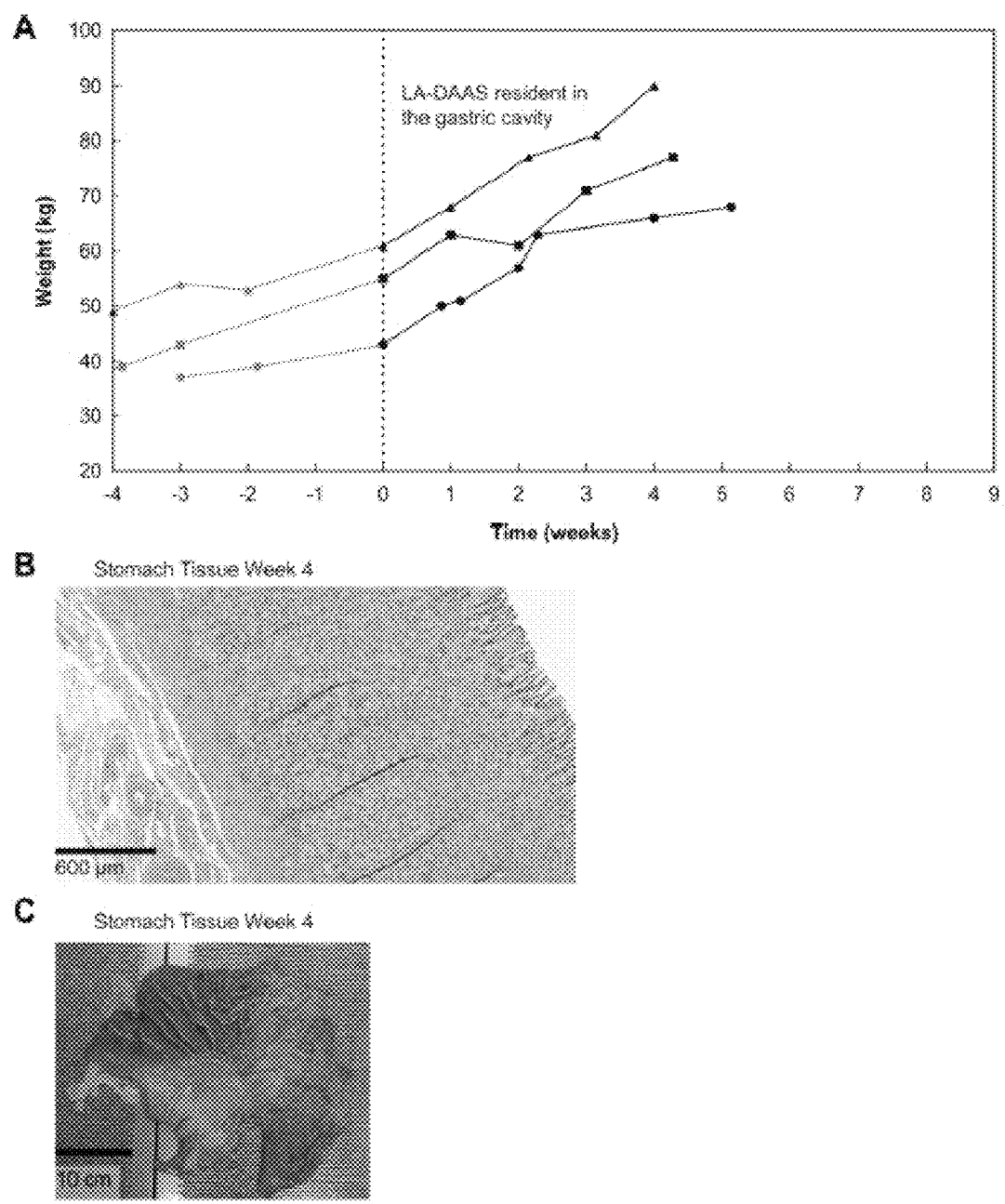
FIGS. 16A-16C show effect of the long-acting direct-acting antiviral system (LA-DAAS) on the weight and stomach tissue of swine, according to one set of embodiments.

We evaluated month-long gastric retention of the LA-DAAS with Yorkshire swine, which have similar gastric anatomy to humans and have been used for evaluating previous long-acting drug delivery platforms.(17, 27) Gastric residence was confirmed for 28 days using radiographs (FIG. 10C) and endoscopy upon deployment and removal (FIG. 10D), which showed the LA-DAAS remaining in a coil shape. During the gastric residence period, the animals did not show any weight loss, evidence of obstruction or limitation in passage of food or liquids; additionally, mucosal surfaces did not show injury, erosions, or ulcerations (FIGS. 16A-16C). Thus, we demonstrated the safe residence of the LA-DAAS in the gastric cavity for one month.

Figures 11A, 11B, 11C, 11D, 11E:
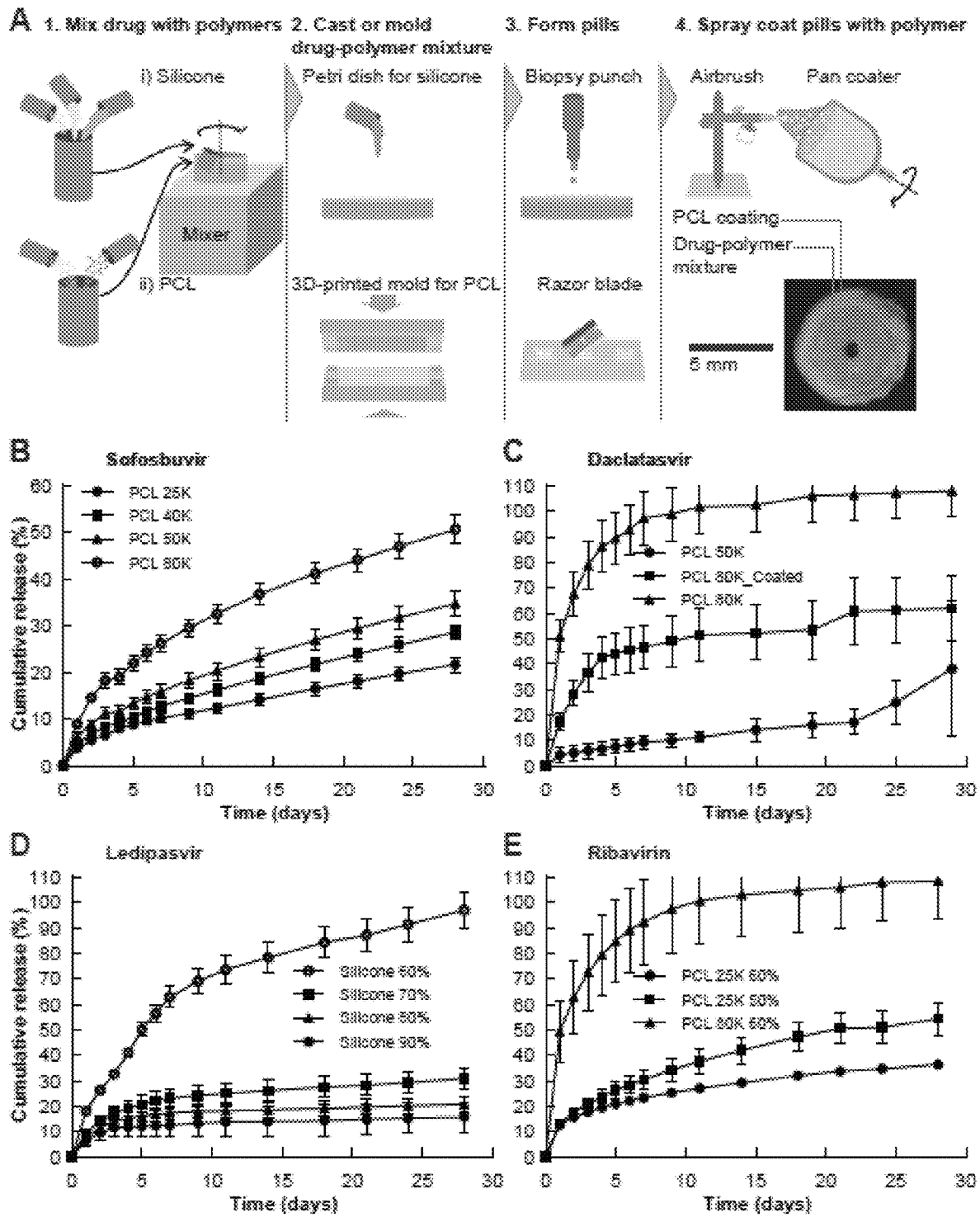
FIGS. 11A-11E show fabrication and in vitro release of direct-acting antivirals (DAAs) from individual drug-polymer pills, according to one set of embodiments.
Figures 17A, 17B, 17C:
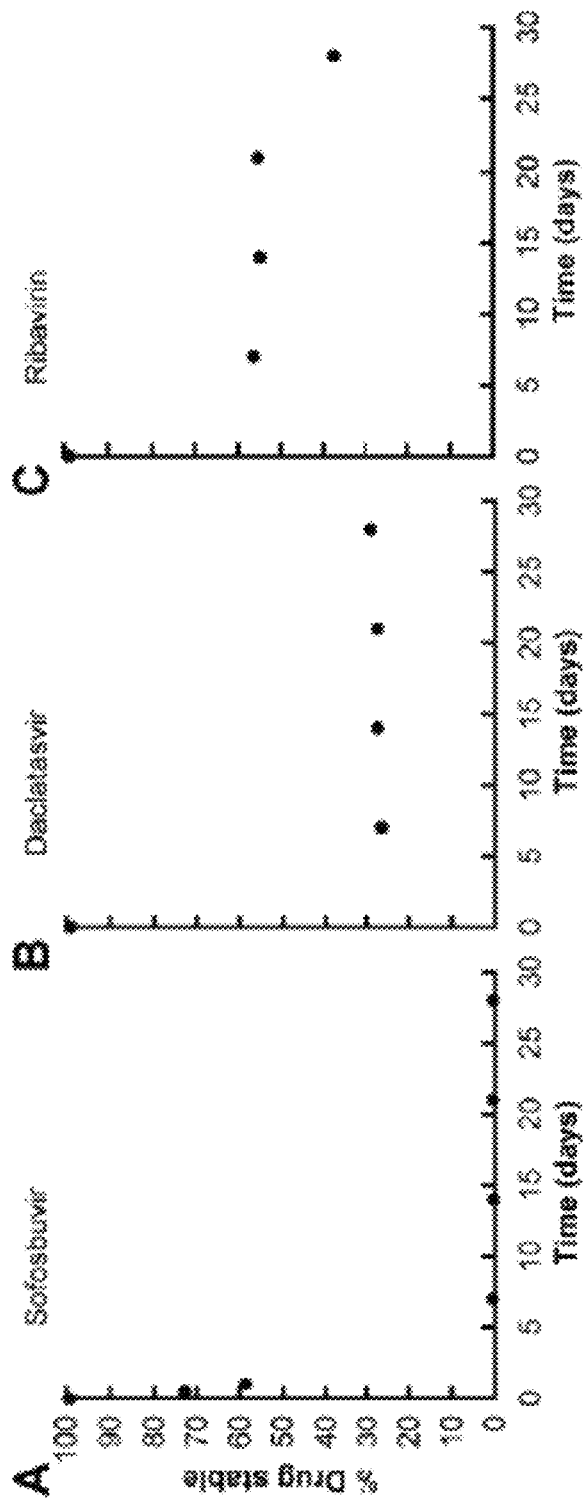
FIGS. 17A-17C show stability of DAAs in simulated gastric fluid (SGF, pH=2), according to one set of embodiments. All DAAs were dissolved in SGF and placed in a shaking incubator (200 rpm, 37° C.). Samples were collected at defined time points for up to 4 weeks and analyzed by HPLC to quantify stability. Ledipasvir degraded immediately in acid, as no signal was detected at t=0 from the HPLC.
Figure 18:
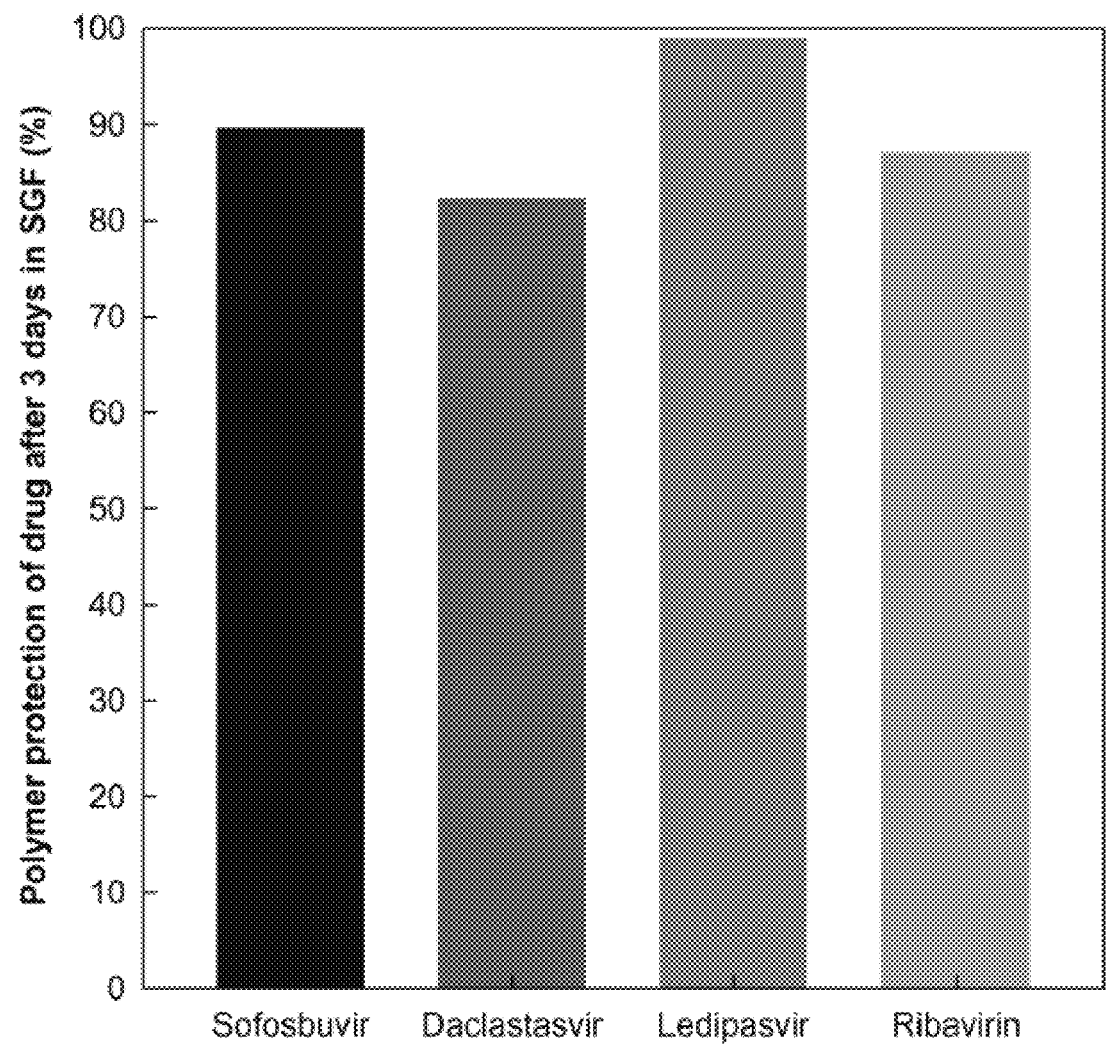
FIG. 18 shows stability of drug-polymer pills in simulated gastric fluid (SGF, pH=2), according to one set of embodiments. Drug-polymer pills were incubated in a shaking incubator at 37° C. and 200 rpm in 50 mL of SGF for 3 days with fluid replaced every day. Then, drug-polymer pills were transferred to acetonitrile for extraction of drug from the polymer pill. The average of extracted amount (n=3) was normalized to the average of extracted drug from drug-polymer pills placed directly in acetonitrile (n=3) to yield the polymer protection metric plotted. PCL protects 89.75% of sofosbuvir, 82.39% of daclatasvir, and 87.11% of ribavirin. Silicone protected 98.96% of ledipasvir.
Figures 19A, 19B, 19C, 19D:
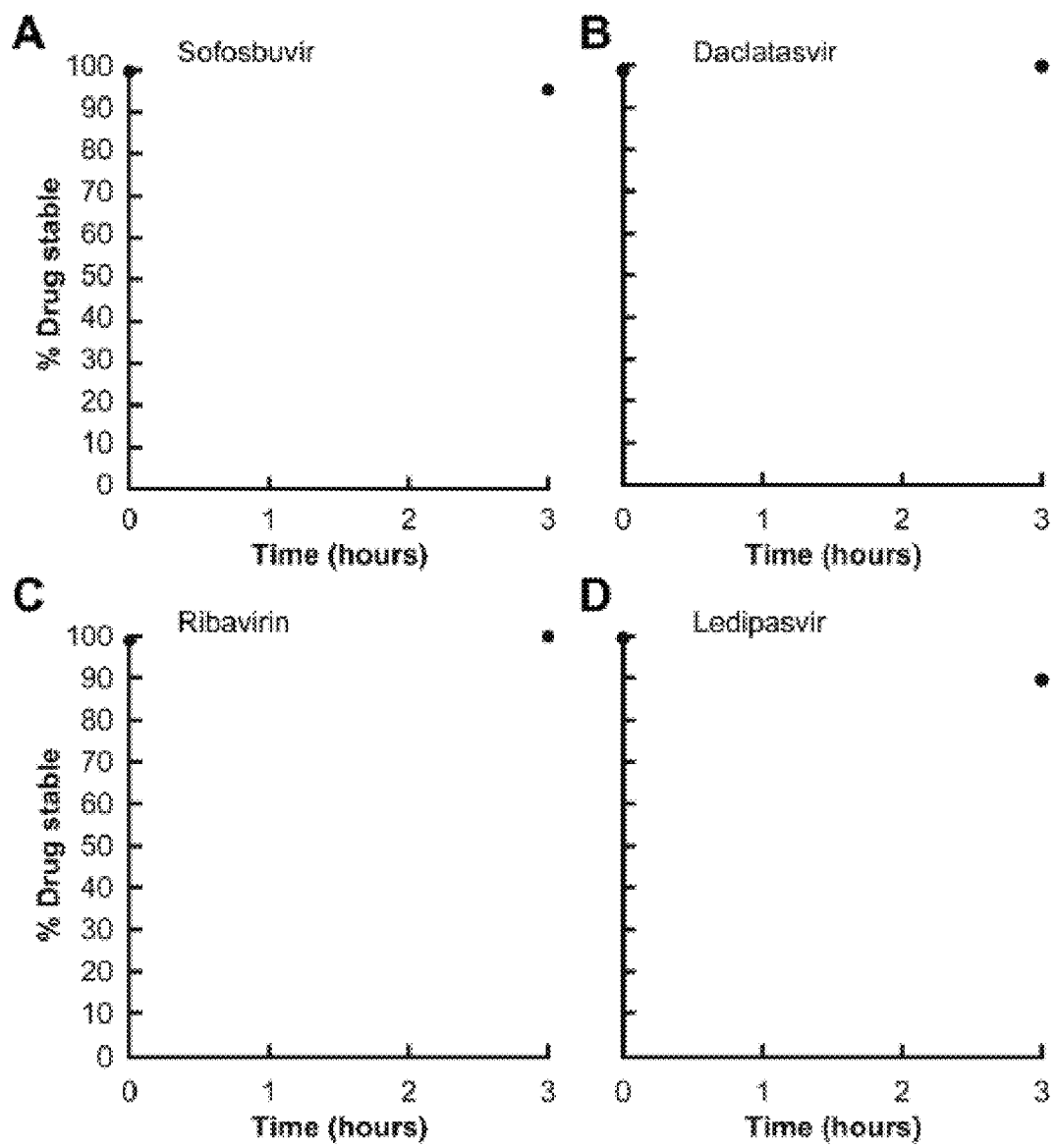
FIGS. 19A-19D show stability of DAAs at 100° C. for 3 hours with analysis by HPLC, according to one set of embodiments.

In Vitro Release Kinetics of the LA-DAAS. We fabricated pills of model DAAs we could procure mixed inside of a silicone or poly(ε-caprolactone) (PCL) matrix and spray-coated PCL coating around each pill to enable controlled release of the DAA (FIG. 11A; n=3 per formulation). Silicone and PCL have both been used as drug release matrices for gastric resident systems and have desirable mechanical properties for use in long-term drug delivery. (17, 27, 28) Additionally, these polymers protect the DAA from degradation in acid. Within 7 days, sofosbuvir degrades by 95% in SGF (FIGS. 17A-17C). However, when mixed with PCL, the drug-PCL pill shields the drug particles from degradation in acid (FIG. 18). PCL protects 89.75% of sofosbuvir, 82.39% of daclatasvir, and 87.11% of ribavirin. Silicone protected 98.96% of ledipasvir.

The DAA in powdered form was mixed homogeneously with either PCL or silicone to form a DAA-polymer blend, which is then casted or molded followed by extraction of individual pills. During the mixing process of drug with PCL or silicone, the drug-polymer mixture was subjected to elevated temperatures. All four DAAs were stable after being subjected to 100° C. for 3 hours, so the manufacturing process did not affect drug stability (FIGS. 19A-19D). To prevent a burst release of drug, a layer of PCL was spray-coated on the surface of the pills.(17, 28, 29) Each pill had a height and diameter of 5 mm with a hole in the center through which to pass the nitinol wire and contribute to the assembled LA-DAAS.

Figures 20A, 20B:
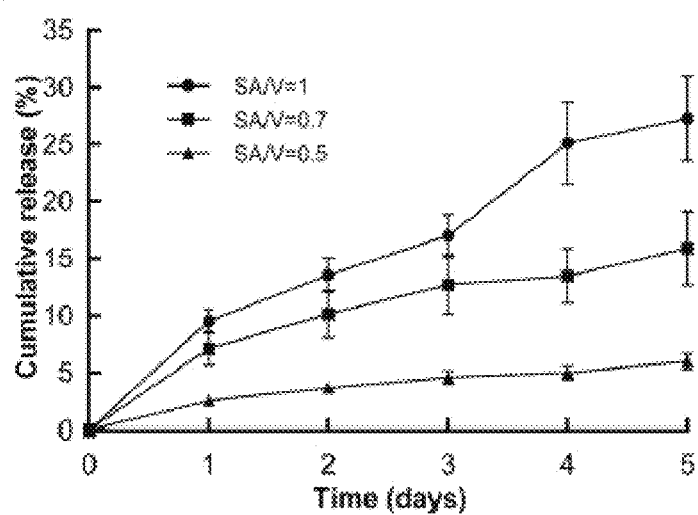
FIGS. 20A-20B show in vitro sofosbuvir release from individual pills with varying surface area to volume (SA/V) ratios, according to one set of embodiments.

We assembled drug-polymer pills for multiple DAAs including sofosbuvir, daclatasvir, ledipasvir, and ribavirin. (30-34) Drug release occurred via diffusion through channels in the polymer matrix.(17, 27, 35) Several factors contributed to tuning the drug release rate from the polymer matrix including the molecular weight of PCL, coating of the pill, the drug loading percentage in the polymer matrix, and the surface area to volume ratio of the pill (FIGS. 11B-11E; FIGS. 20A-20B).(17, 28, 36-38) The rate of sofosbuvir release increased as the molecular weight of PCL increased from 25,000 to 80,000. More crystallinity (low amorphous regions) is associated with lower PCL molecular weight.(38, 39) Therefore, the higher molecular weight has a faster degradation rate due to the presence of more amorphous regions. Increasing the surface area to volume ratio of the pill also increased the sofosbuvir release rate. Daclatasvir release was modulated by varying the molecular weight of PCL and coating the pill to reduce the burst release of drug, resulting in a linear cumulative release versus time profile. Ribavirin release increased at higher PCL molecular weight and with a higher drug loading percentage. Increasing the drug loading percentage of ledipasvir resulted in a faster release rate. Overall, the drug-polymer pills provided a method to tune the release rate of four DAAs for one month.

Figures 21A, 21B:
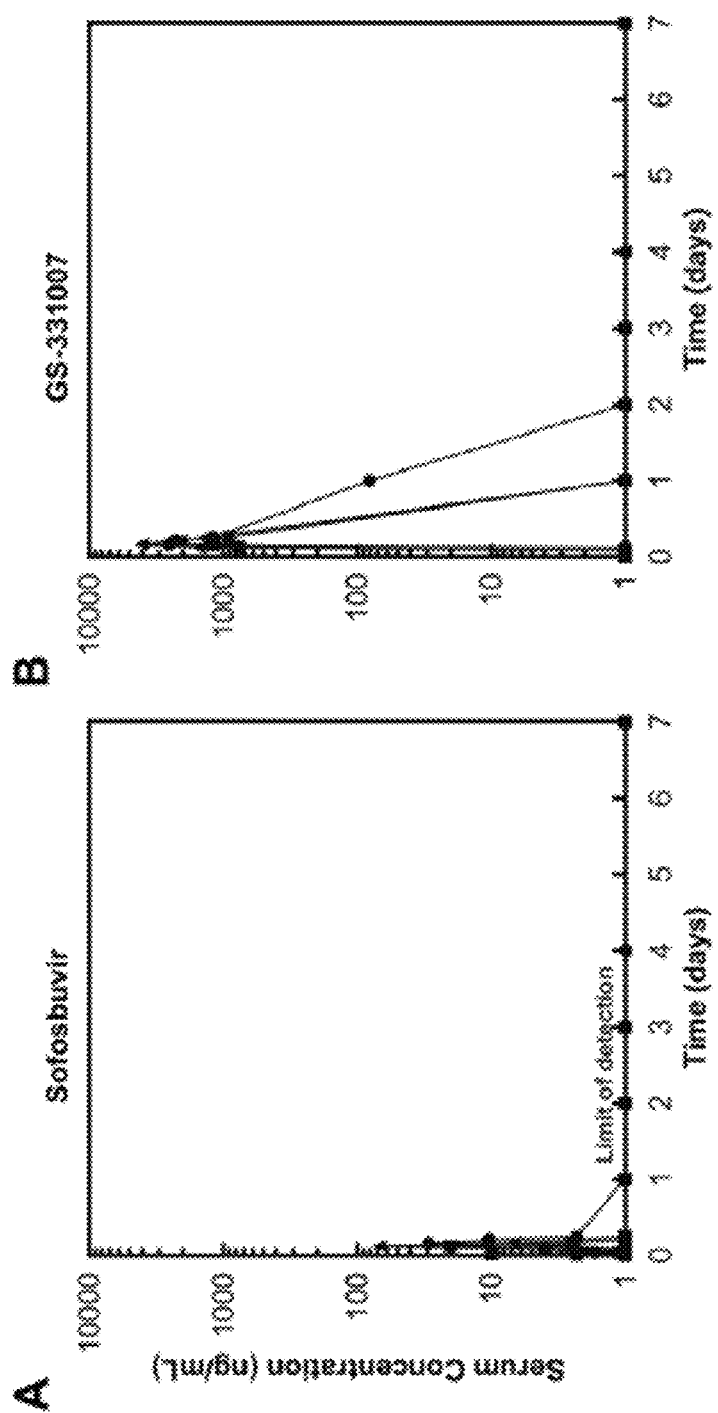
FIGS. 21A-21B show in vivo serum concentrations following a 400 mg dosage of sofosbuvir to a swine model, according to one set of embodiments.
Figure 22:
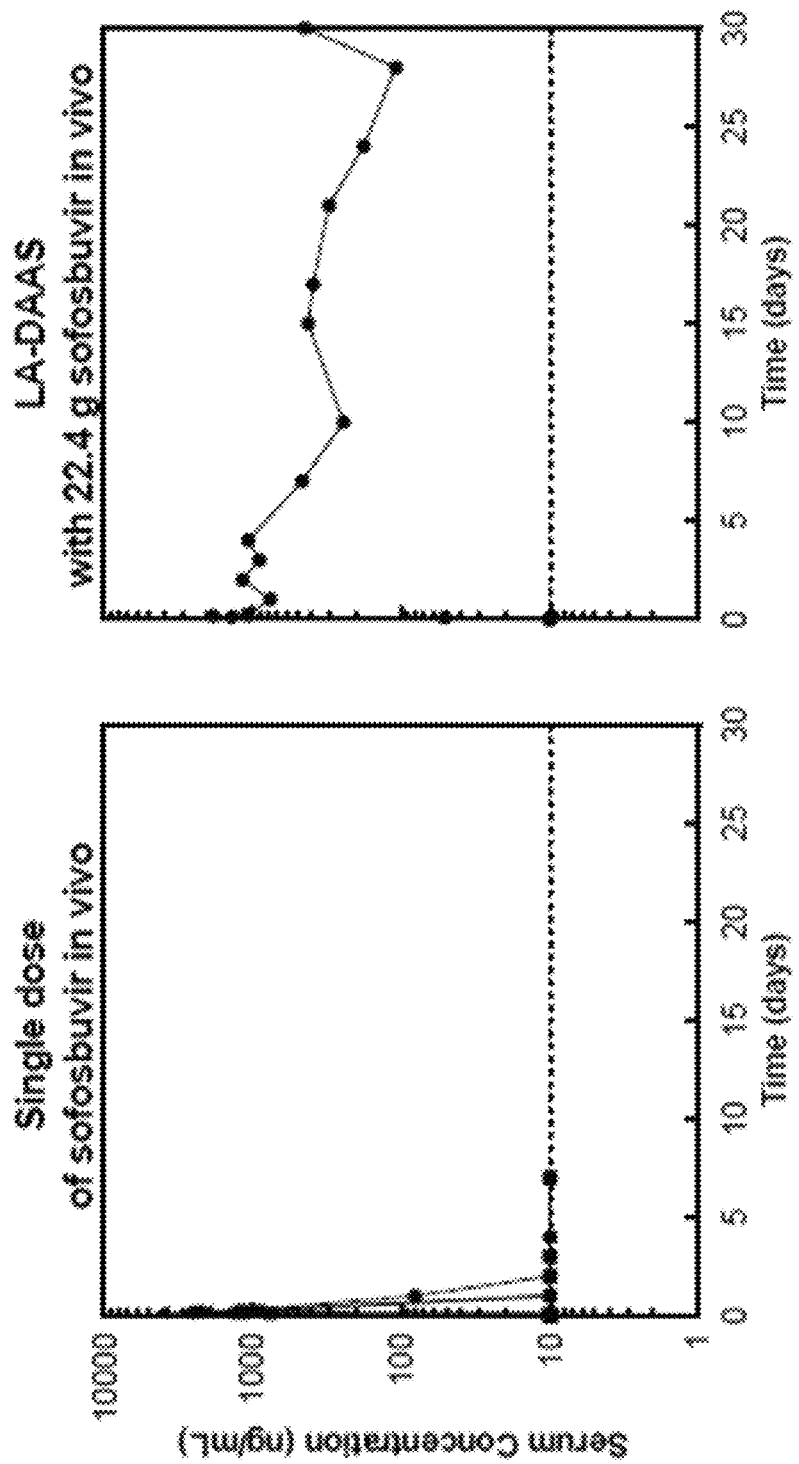
FIG. 22. Left: Concentration-time profiles of the sofosbuvir metabolite GS-331007 in serum after administering a single dose of 400 mg (n=3), according to one set of embodiments. Right: Concentration-time profiles of the sofosbuvir metabolite GS-331007 in serum after administering the LA-DAAS, which had 22.4 g of sofosbuvir across four formulations (n=1), according to one set of embodiments.

In Vivo Applications from the LA-DAAS. We next studied the LA-DAAS' long-term drug delivery in swine and evaluated its electronic sensing capabilities. According to prior work we conducted in a swine model, the renally eliminated metabolite GS-331007 is the primary analyte of interest for clinical pharmacology studies with sofosbuvir (FIG. 21A-21B).(40, 41) Therefore, we prepared three LA-DAAS loaded with 11.2 g of sofosbuvir and administered them in swine. The LA-DAAS was assembled to contain 300 pills using two different formulations, which released drug simultaneously. The serum concentration profile of a 400-mg single dose is shown in FIG. 12A. The drug was absorbed rapidly, and detectable concentrations were observed within 3 hours. No drug was detectable after 1 day with the single-dose formulation. In contrast, drug was detectable for at least 28 days when sofosbuvir was dosed in the LA-DAAS (FIG. 12B). A 22.4 g LA-DAAS showed ongoing high levels of sofosbuvir release on day 30 suggestive of greater than 1 month drug delivery capability (FIG. 22).

Figure 23:
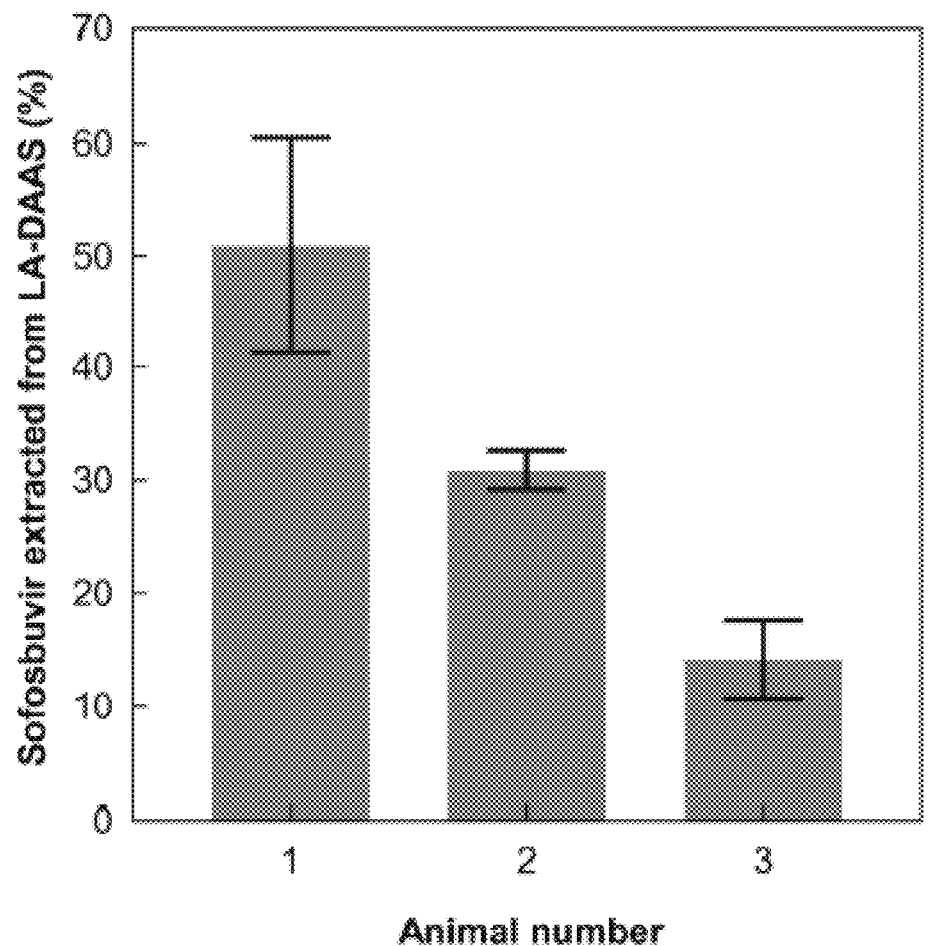
FIG. 23 shows sofosbuvir extraction from the LA-DAAS after residence for at least 28 days in vivo (n=3), according to one set of embodiments. Five drug pills were randomly chosen from the LA-DAAS after it was retrieved from the gastric cavity of swine. The pills were placed in 50 mL of acetonitrile for 14 days and placed in an incubator shaker. The sofosbuvir-PCL pills were completely dissolved, and the amount of sofosbuvir was quantified using the HPLC. The percentage of sofosbuvir remaining in the pill is plotted for all three swine experiments. Error bars represent SD for n=5 samples in each group.
Figures 24A, 24B:
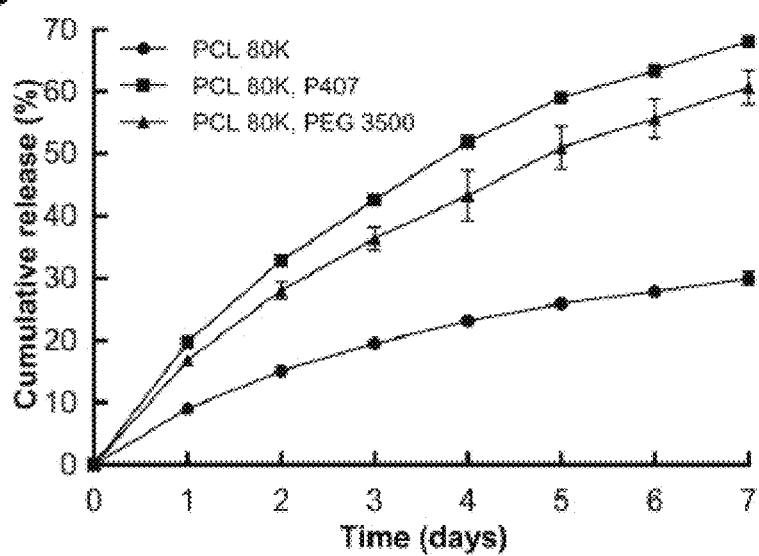
FIGS. 24A-24B).

After one month of gastric residence in vivo, the LA-DAAS was retrieved for extraction of sofosbuvir from the pills (FIG. 23). The sofosbuvir-PCL pills were completely dissolved, and the amount of sofosbuvir was quantified using the HPLC. Following 28 days, gastric release individual tablets were recovered from each device from 3 swine. These contained 15-50% of drug. The addition of excipients, such as Pluronic P407 or poly(ethylene glycol) (PEG), to the drug-PCL matrix increased the release rate of sofosbuvir (FIGS. 24A-24B).(28)

Figure 25:
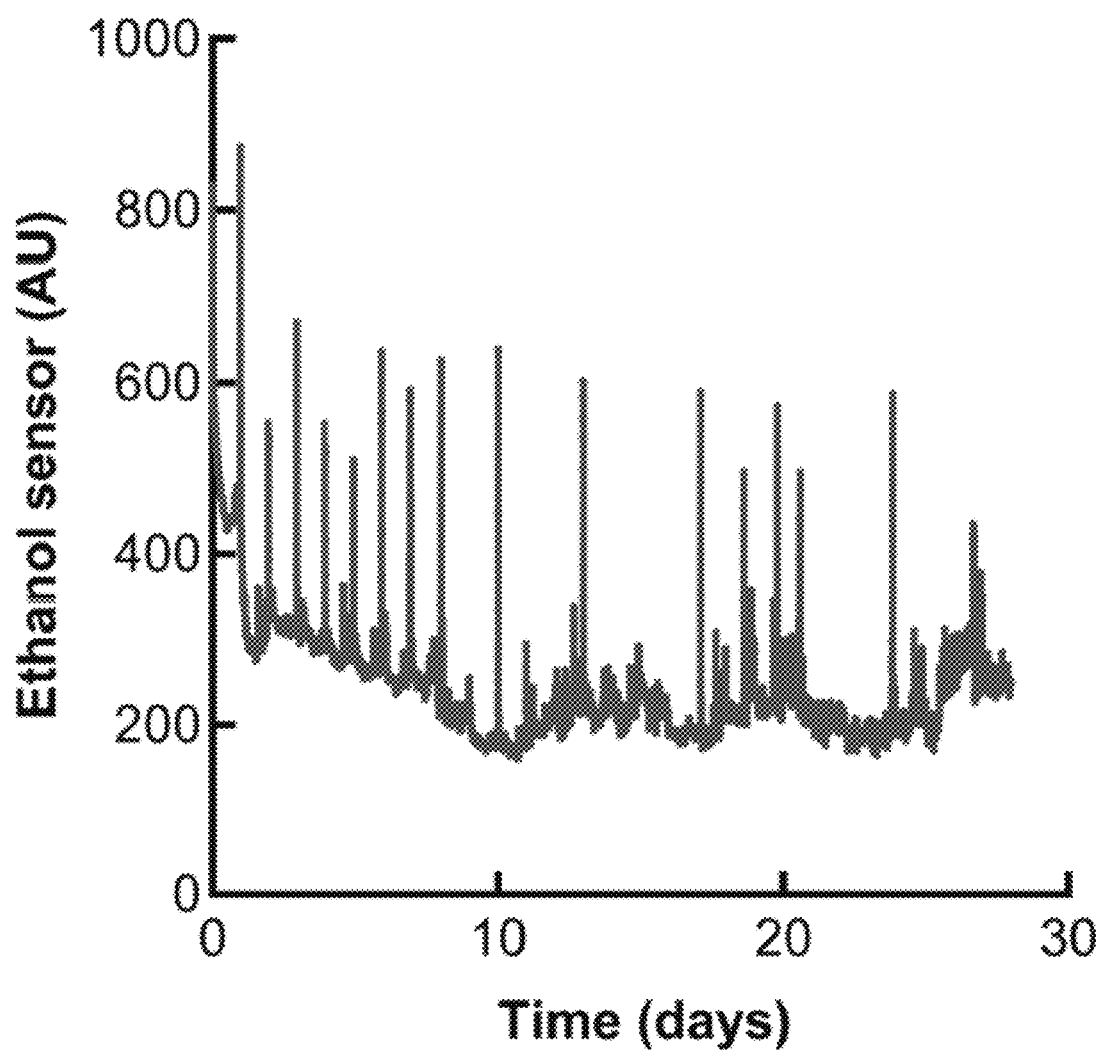
FIG. 25 shows representative analog signal of ethanol sensor during in vitro evaluation for 28 days n=3), according to one set of embodiments. The LA-DAAS was placed in a beaker containing 300 mL of simulated gastric fluid (SGF) and was connected to an Arduino Uno microcontroller. An LCD screen was used to display the readings, and the data was saved via a text file on a 4 GB Memory Card MicroSD, then imported to an Excel file upon the completion of the experiment. On days 0, 1, 2, 3, 4, 5, 6, 7, 9, 11, 14, 18, 21, 24, and 27, 5 mL of ethanol was pipetted into the beaker. The analog reading was recorded followed by replacing the beaker with fresh SGF. The analog signal was recorded every 3 seconds.
Figure 26:
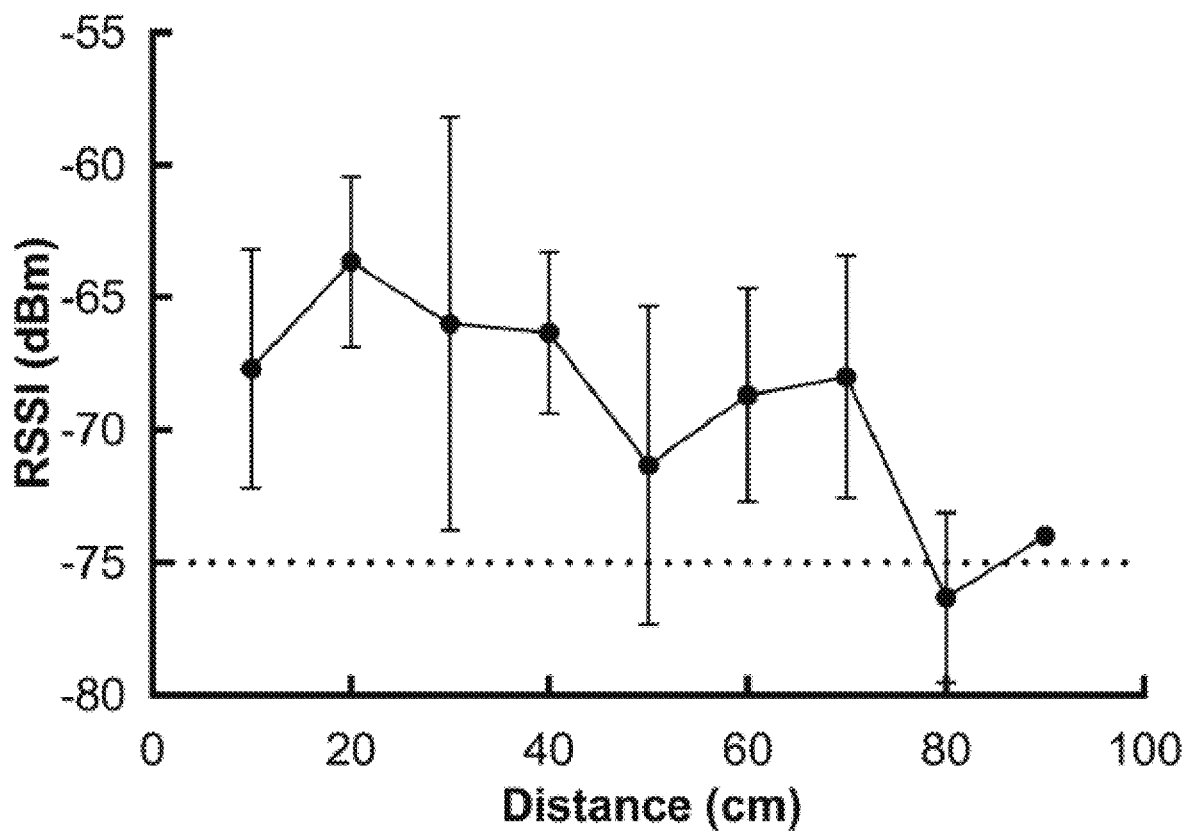
FIG. 26 shows average received signal strength indicator (RSSI) of the Bluetooth sensor in a porcine stomach measured with a smart phone, according to one set of embodiments. Error bars represent SD for n=3 samples. RSSI has an approximately linear relationship with distance between the Bluetooth transmitter and receiver, within 1 meter of separation. Above −75 dBm, the sensor is working accurately.
Figure 27:
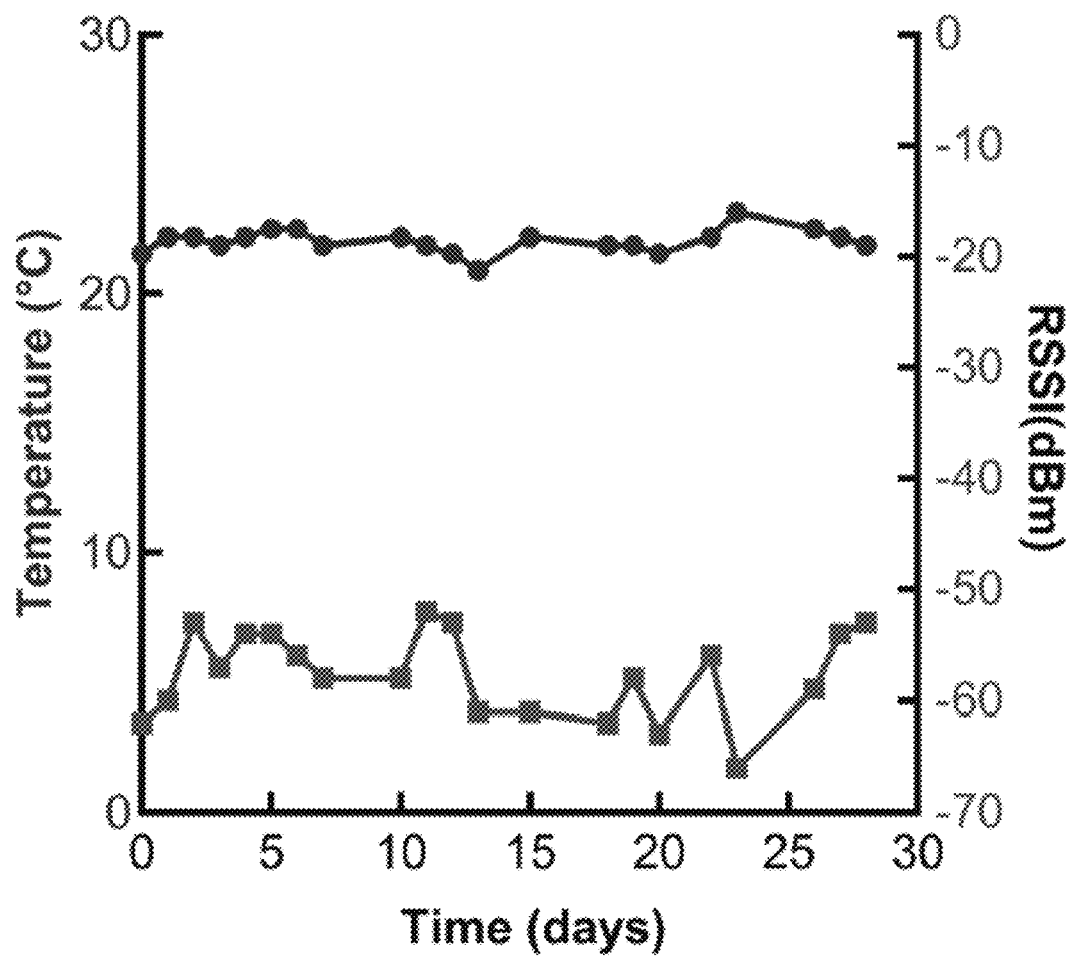
FIG. 27 shows representative temperature and received signal strength indicator (RSSI) during in vitro evaluation for 28 days (n=3), according to one set of embodiments. The LA-DAAS was placed in a beaker containing 300 mL of simulated gastric fluid (SGF) at room temperature, and a smart phone application was used to measure the RSSI (square data points) and request the temperature (circular data points) approximately every 24 hours. Results indicate the stability of the Bluetooth module and temperature sensor attachment during prolonged exposure to gastric conditions.

The LA-DAAS was also equipped with an ethanol, Bluetooth, and temperature sensor that communicated with a patient-friendly user interface on a phone application via a Bluetooth module. Batteries were included at the end of the LA-DAAS to provide power to the sensors (FIG. 12C). Prior to evaluation in a swine model, the sensors were studied for one month in vitro immersed in SGF. The ethanol, temperature, and Bluetooth modules were insulated within a piece of tubing to shield them from the gastric conditions. The head of the ethanol sensor was wrapped in a membrane for additional protection, and we successfully demonstrated the sensor's ability to respond to addition of ethanol at designated timepoints (FIG. 25). The RSSI has an approximately linear relationship with distance between the Bluetooth transmitter and receiver, within 1 meter of separation (FIG. 26). Results indicate the stability of the Bluetooth module and temperature sensor attachment during month-long exposure to acidic conditions (FIG. 27). When evaluated in a euthanized swine's stomach, all sensors functioned as predicted—the ethanol sensor detected addition of ethanol to gastric fluid, and the temperature sensor recorded body temperature of the swine. A cell phone was able to receive Bluetooth signal within 1 meter.

Cost-Effectiveness of the LA-DAAS for HCV Treatment. We simulated two treatment strategies for patients: 1) standard DAA therapy or 2) the LA-DAAS (FIGS. 13A-13B). In the base case analysis of the LA-DAAS delivered nasogastrically once a month in patients with average adherence and likelihood of returning for repeat treatment, the LA-DAAS was cost-effective with an ICER of $39,800 per QALY compared to conventional DAA therapy (FIG. 13C). 96.7% of patients achieved SVR with the LA-DAAS compared to 93.9% with DAA therapy. The LA-DAAS was similarly cost-effective in PWID, with an ICER of $36,700 per QALY. With the LA-DAAS, 96.3% of patients achieved SVR compared to 90.5% with DAA therapy. Interestingly, the LA-DAAS was even more cost-effective when compared to a DOT system, with an ICER of $26,300 per QALY. 96.3% of patients with the LA-DAAS achieved SVR compared to 92.6% with DOT.

Figure 28:
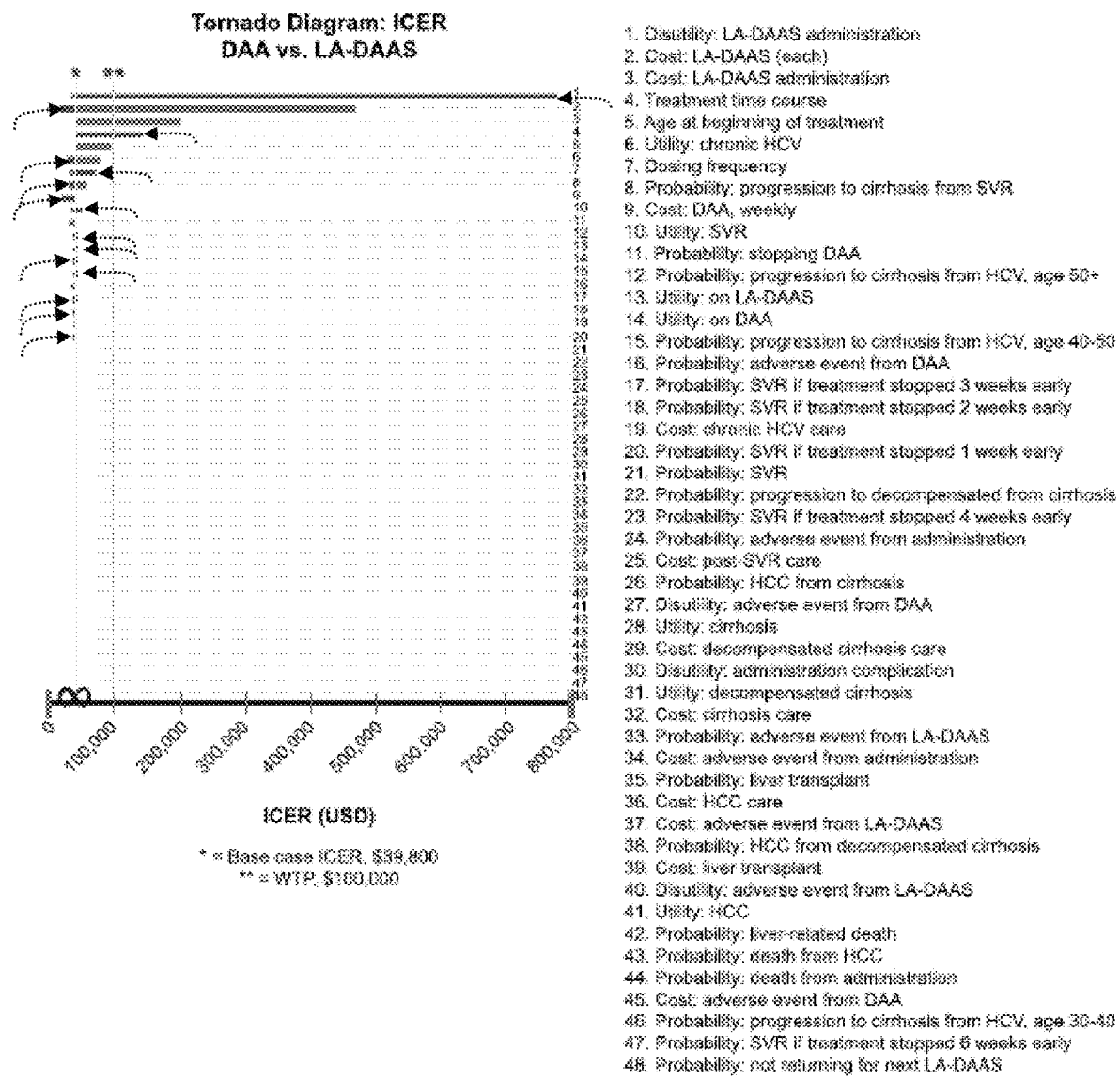
FIG. 28 shows a tornado diagram for the cost-effectiveness analysis (base case model), according to one set of embodiments. The tornado diagram shows one-way sensitivity analyses of the ICER for each parameter in the model. Parameters are listed 1-48 in descending order of effect on the ICER. The base case ICER is denoted by the single asterisk ($39,800). Changes in parameters that moved the ICER to the left of this value made the LA-DAAS more cost-effective. Changes in parameters that moved the ICER to the right of this value made the LA-DAAS less cost-effective. Changes in parameters that moved the ICER past the double asterisk, which denotes the WTP threshold ($100,000), made the LA-DAAS no longer cost-effective compared to DAA. Values with an arrow pointing to them are low values of the parameter tested on the side of the base case ICER corresponding to the arrow; values without an arrow pointing to them are high values of the parameter tested on the side of the base case ICER corresponding to the arrow.
Figure 29A:
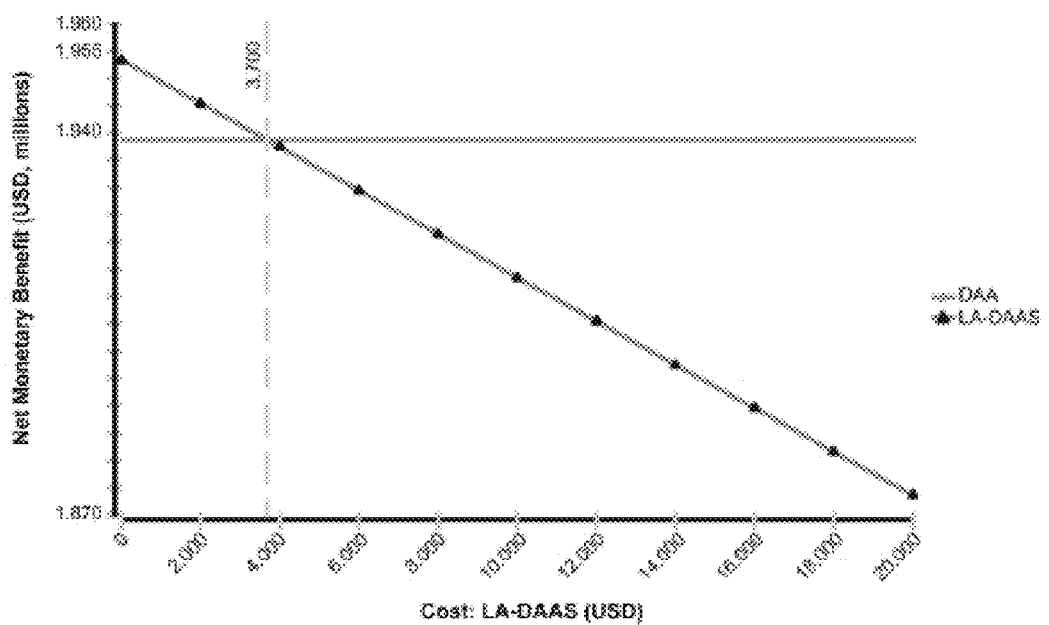
FIGS. 29A-29B shows one-way sensitivity analyses for two key variables in the cost-effectiveness analysis (base case model), according to one set of embodiments.
Figure 29B:
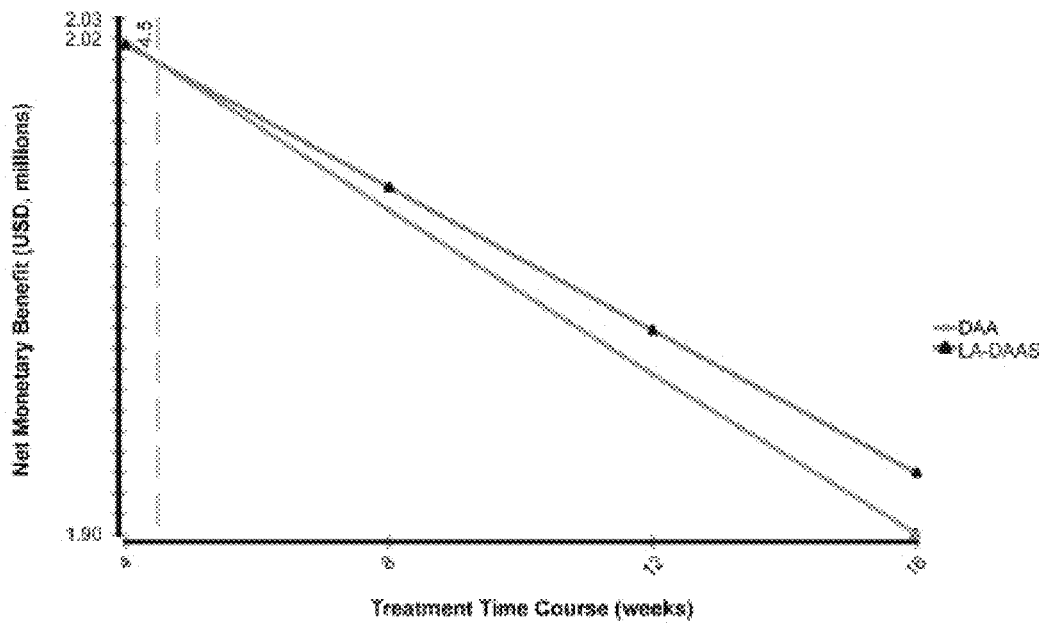

One-way deterministic sensitivity analyses were performed to investigate the effects of changes in model parameters on estimated outcomes (FIG. 28). Variables that changed the optimal strategy in the base case were disutility of LA-DAAS administration, cost of the LA-DAAS device, cost of LA-DAAS administration, treatment time course, and likelihood of not returning for repeat LA-DAAS administration. DAA became the preferred strategy if the LA-DAAS administration was particularly uncomfortable (disutility greater than −0.03 per administration, with 0 being no effect and −1 the equivalent of death), or if the cost of each administration were greater than $2,700. The LA-DAAS remained cost-effective up to a device cost of $3,700, which is comparable to the cost of intragastric balloons and other similar devices (FIG. 29A).(42) The LA-DAAS remained cost-effective for HCV treatment courses of at least 5 weeks, which represents all current HCV regimens (FIG. 29B).(43) Finally, DAA became the preferred strategy if patients were unlikely to return for repeat LA-DAAS administration (probability of returning for repeat treatment only 30% over 1 year). Notable variables that did not change the preferred treatment strategy included administration frequency of the LA-DAAS (dosing every 2, 4, 6, or 8 weeks were all cost-effective) and age at beginning of treatment. We also performed a secondary analysis for single administration of the LA-DAAS, anticipating a future design capable of delivering a full treatment course, which found similar results. Overall, these results suggest that the LA-DAAS is cost-effective across many treatment and patient variables.

DISCUSSION

With the development of effective and well tolerated DAA therapy, it is now possible to cure hepatitis C in all patients. In this study, we describe a novel drug delivery system that can safely and effectively provide at least month-long doses of DAA therapy for HCV. Although long-acting approaches to the treatment of HIV and tuberculosis have been described, this is the first description of a long-acting, enteral solution to the challenge of expanding HCV treatment.(17, 44, 45) These data provide a basis for expanded research to adapt the technology to treatment of HCV-infected humans, including improving the system to ultimately achieve single-dose administration of HCV treatment.

Treatment of HCV infection historically involved the use of a pegylated form of interferon alfa that prolonged half-life and allowed weekly dosing. An albumin-conjugated form of interferon with even a longer half-life was also considered. (46) However, since the advent of DAA formulations, all treatment requires daily oral administration. We now adapt an enteral approach we have used for treatment of tuberculosis to HCV.

We anticipate that further development of the LA-DAAS will include further preclinical evaluation in additional animal models. Optimizing drug release kinetics from the drug-polymer pills is a critical next step, such that serum concentrations of the drug remain within the therapeutic window for efficacious treatment with maximal release from the tablets. We will also want to more closely mimic the typical regimens used in humans including expansion to pangenotypic DAA formulations such as glecaprevir/pibrentasvir and study of daclatasvir or velpatasvir with sofosbuvir. Furthermore, based on our current data, future evaluation of prolonged device gastric residency (>one month) with associated drug delivery towards single administration for complete treatment with pangenotypic drug combinations is warranted. Additionally, long-term safety and stability of the electronic sensors must be assessed in the gastric environment, as well as long-term presence of the LA-DAA device, for anticipated retrieval failure. Other considerations include whether nasogastric delivery of the LA-DAAS may be a challenge; though inexpensive, patients may find this delivery system uncomfortable. In such cases, endoscopic delivery may be preferable, and would also allow for greater volume of drug delivery and reduced dosing frequency.

Our economic analysis found that the LA-DAAS can be cost-effective across various patient populations, including both the general population and PWID. Though the LA-DAAS was generally preferred over DAA therapy in most scenarios tested, we identified several factors that could make conventional DAA therapy preferable to LA-DAAS: Patients who find nasogastric delivery very unpleasant, high cost of the LA-DAAS or of its administration, short DAA treatment courses, and patients unlikely to return monthly for repeat LA-DAAS administration. This later limitation could be particularly challenging in some settings. In others, such as in corrections, this system might be preferred over DAA therapy. For patients for whom nasogastric delivery is markedly unpleasant, one could consider administration under sedation or endoscopically, though these costs were not analyzed in this model. Other populations that could benefit from this system include intubated and ventilated patients, such as post-transplant patients in the advent of HCV+ organ transplantation, particularly those requiring DAAs such as glecaprevir/pibrentasvir that cannot be crushed and administered through typical enteral access.

There are a number of limitations to our cost-effectiveness study. As with any modeling analysis, the accuracy of our model was restricted by available data. In particular, adherence rates, the impact of adherence on SVR, and the likelihood of returning for a repeated LA-DAAS administration were challenging to estimate, and thus we performed wide sensitivity analyses for these parameters. Our model did not capture the utility of reduced HCV transmission among PWID, which likely underestimates the overall benefit and cost-effectiveness of the LA-DAAS.(11) Additionally, we did not include probability of reinfection in our model. If patients in one of the treatment strategies were reinfected more often than those in the other strategy, that would likely increase overall treatment costs in that arm and affect our calculated ICER. However, we do not expect that this would differ significantly between patients treated with DAA therapy vs. the LA-DAAS. Finally, our model used the same drug cost for conventional DAA therapy and the cost of DAA included within the LA-DAAS (separate from device and administration costs). This assumes that further lowering of drug cost for DAAs will be applicable to the LA-DAAS as well. If there are heavy discounts applied to oral DAA therapy that are not included in pricing of the LA-DAAS, then the LA-DAAS could become cost-ineffective.

Ultimately, whether any given patient is more likely to adhere to or prefer daily pills versus monthly repeated nasogastric treatment will vary depending on the patient, and patient preference regarding modality of HCV treatment should guide choice of therapy. Further steps in development of the LA-DAAS should include engaging patients and health care providers in the hepatitis C community to evaluate the acceptability and feasibility of such an approach, as well as ongoing work to move toward single-dose administration for full HCV treatment. We believe that providing a range of delivery options to patients and healthcare providers will aid in maximizing deployment of recognized effective DAAs.

Materials and Methods

Figure 14A:
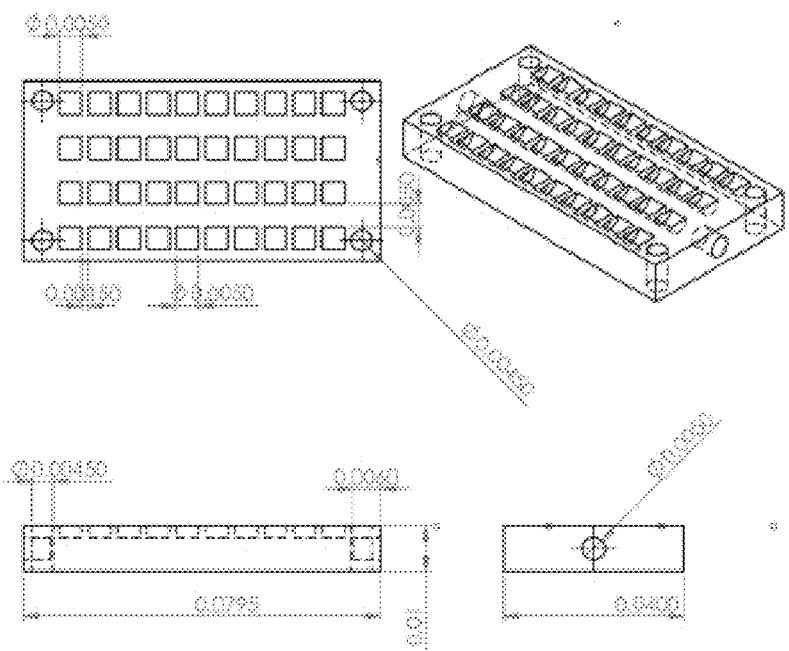
FIGS. 14A-14B show computer-aided design sketches of mold for making drug-PCL pills, according to one set of embodiments.
Figure 14B:
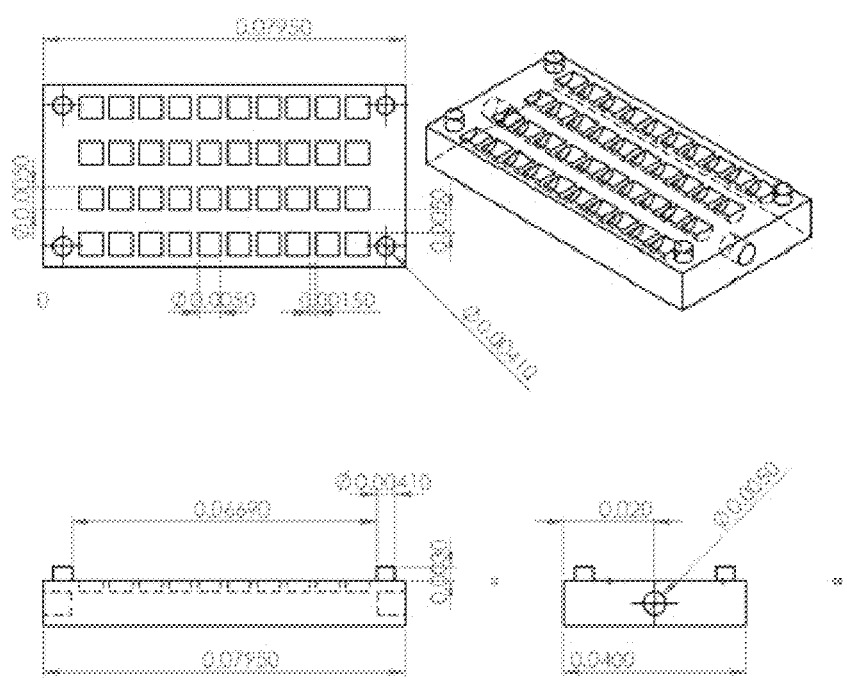
Figures 15A, 15B, 15C, 15D:
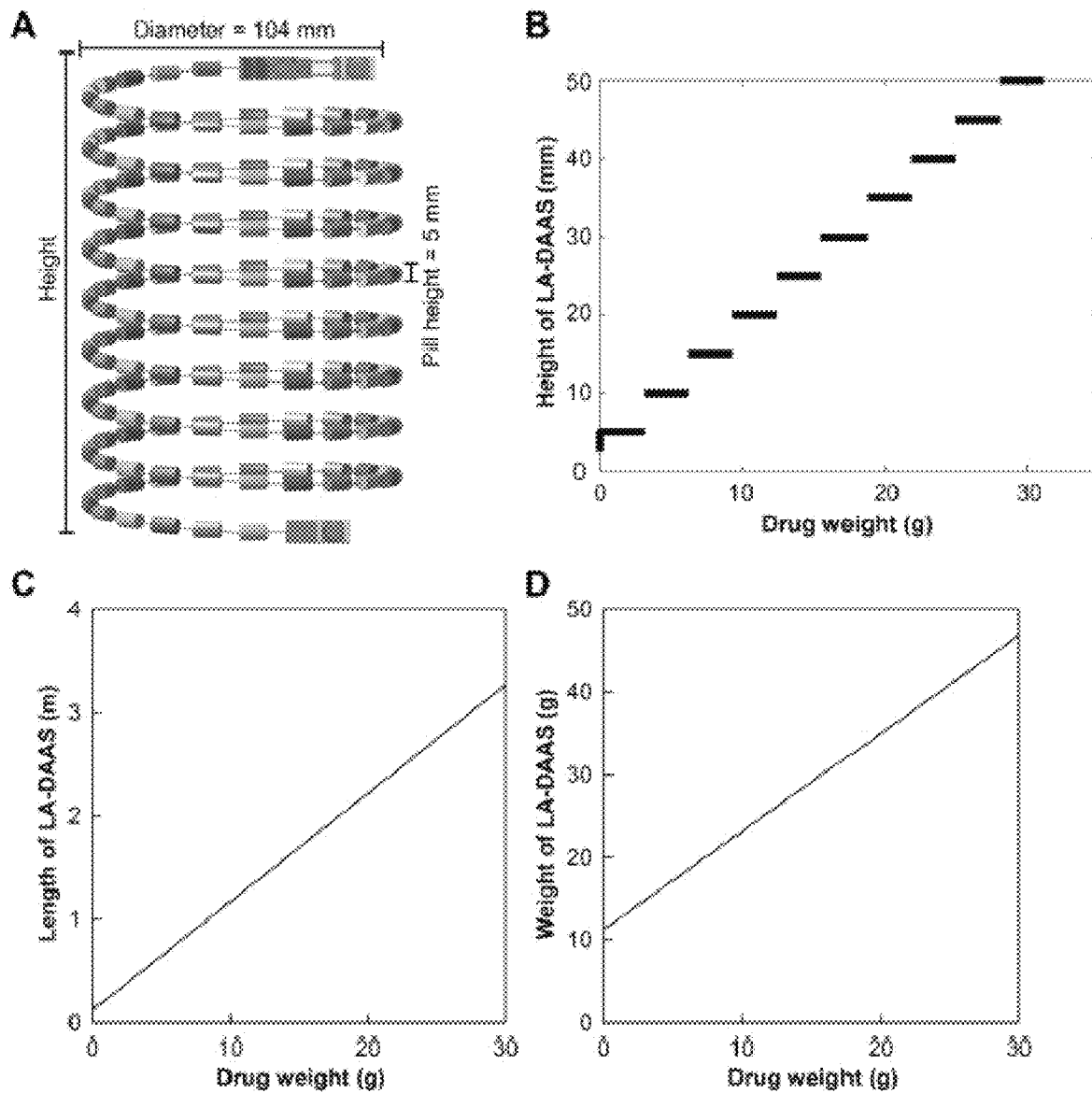
FIGS. 15A-15D show physical parameters of the long-acting direct-acting antiviral system (LA-DAAS) as the drug weight increases, according to one set of embodiments.

LA-DAAS prototyping and in vitro drug release. LA-DAAS were assembled and in vitro drug release was evaluated by High-Performance Liquid Chromatography (HPLC) as previously described, with modifications including novel formulations for DAAs (FIGS. 14A-14B).(17) The following drugs were acquired: sofosbuvir (Hefei Hirisun Pharmatech Co., Ltd, Hefei, China), daclatasvir and ledipasvir (Hangzhou APIChem Technology Co, Ltd., Hangzhou, Zhejiang, China), and ribavirin (ChemShuttle, Hayward, CA). Drug was mixed with either vinylpolysiloxane (VPS) (Zhermack SpA, Badia Polesine, Italy) or poly($\epsilon$-caprolactone) (PCL) obtained from Nexeo Solutions Inc. (The Woodlands, TX) in a SpeedMixer DAC 150.1 FVX-K (FlackTek Inc., Landrum, SC). Drug loading percentages were determined relative to the final polymer mixture weight: sofosbuvir (50%), daclastasvir (40%), ledipasvir (40%), and ribavirin (40%). Individual drug-polymer pills were used to evaluate long-term release kinetics (n=3 per formulation). Pill formulations were incubated in a New Brunswick Innova 44 shaking incubator (Eppendorf, Hauppauge, NY) at 37° C. and 200 rpm in 50 mL of fluid for 28 days, with solution exchanges at specified time intervals. Drug concentrations were then analyzed using an Agilent 1260 Infinity II HPLC system.

In vivo evaluation of the LA-DAAS. All animal experiments were performed in accordance with protocols approved by the Committee on Animal Care at the Massachusetts Institute of Technology as previously described.(17) To assess the oral pharmacokinetics of immediate release formulations and the LA-DAAS, we administered them to female 30-75 kg Yorkshire swine (n=3 per formulation). Animals were fed daily in the morning and in the evening with a diet consisting of pellets (Laboratory mini-pig grower diet, 5081), in addition to a midday snack consisting of various fruits and vegetables. The immediate release formulation was prepared by weighing and filling 400 mg of sofosbuvir in two "00" gelatin capsules 15 minutes prior to dosing. Prior to dosing, the swine were sedated with Telazol® (5 mg/kg IM), xylazine (2 mg/kg IM), and atropine (0.04 mg/kg IM), intubated, and maintained with isoflurane (1 to 3% inhaled). Immediate release formulations and the LA-DAAS were deployed in the stomach via an endoscopic guided overtube. The overtube was removed after the devices were administered. For evaluation of the safety and residence time of the LA-DAAS, the animals were clinically assessed twice a day for evidence of GI obstruction including inappetence, abdominal distension, lack of stool, and vomiting. Additionally, the animals were evaluated radiographically every 3-4 days for evidence of GI obstruction and/or perforation. Tissue samples were collected before and after the device was placed in the stomach for histopathological analysis, and macroscopic images were taken once the device was retrieved to study any possible mucosal damage. At indicated time points, blood samples (3 mL) were collected from a central venous catheter. Serum samples were separated from blood by centrifugation (3220 rpm, 10 min at 4° C.) and were stored at −80° C. for further analysis. Drug concentrations in serum were analyzed using Ultra-Performance Liquid Chromatography-Tandem Mass Spectrometry (UPLC-MS/MS) on a Waters ACQUITY UPLC®-I-Class System aligned with a Waters Xevo®-TQ-S mass spectrometer (Waters Corporation, Milford, MA).

Integration and evaluation of electronic sensors. The MQ3B alcohol sensor and required accessories were purchased from Digi-Key, Thief River Falls, MN The sensor was encapsulated in a 0.5 µm pore polytetrafluoroethylene membrane (Cole-Parmer, Vernon Hills, IL) attached to one end of the LA-DAAS in Tygon tubing and connected to an Arduino Uno microcontroller (Digi-Key) to output the sensor reading. The other end of the LA-DAAS consisted of a TMP36 analog temperature sensor (Analog Devices, Inc., Norwood, MA) soldered to an Adafruit Feather 32u4 Bluefruit (Adafruit Industries, New York, NY), a breakout board for the ATMega32u4 microcontroller (Atmel Corporation, San Jose, CA) and the nRF51822 BLE system (Nordic Semiconductor, Trondheim, Norway). Temperature and elapsed time since administration data were delivered to an iOS-enabled mobile phone (Apple Inc., Cupertino, CA) via an application with a user interface. Long-term stability of the sensors attached to the LA-DAAS were evaluated for 28 days in simulated gastric fluid (SGF). Ex vivo evaluation was conducted in euthanized swine to measure ethanol and temperature in gastric fluid as well as the received signal strength indication (RSSI).

Cost-effectiveness model design. A Markov model of patients treated with either standard DAA therapy or with the LA-DAAS (dosed monthly) was constructed in TreeAge Pro (Williamstown, MA). Model parameters were estimated from the literature and prior published models of HCV.(11, 47, 48) The simulated cohort of 40-year-old non-cirrhotic men was followed over a lifetime time horizon. Three main cohorts were simulated: a base case cohort with average DAA adherence and likelihood of returning for repeat LA-DAAS administration, a cohort of PWID with lower adherence and likelihood of returning, and a cohort of PWID enrolled in a directly observed therapy (DOT) program with improved DAA adherence but lower likelihood of returning for repeat LA-DAAS. After treatment with DAA or LA-DAAS for 12 weeks, patients in each cohort would either complete treatment or not (depending on adherence and likelihood of returning for repeat LA-DAAS), and then either achieve SVR or continue with chronic HCV. Patients could then progress to cirrhosis and then to decompensation, HCC, liver-related death, or liver transplant. All patients in the model could die of non-liver related death. The Markov cycle length was 1 week. The weekly cost of DAA therapy was estimated from wholesale cost estimates of glecapravir/pibrentasvir, discounted by 50% to reflect current real-world costs.(11) The cost of the LA-DAAS included cost of DAA therapy plus monthly device cost and nasogastric administration costs. The primary outcomes of the analysis were unadjusted life-years (overall survival), quality adjusted life years (QALYs), and incremental cost-effectiveness ratio (ICER) per QALY between competing treatment strategies from a healthcare perspective. The willingness to pay (WTP) threshold was $100,000/QALY.(49) Cost estimates were converted to 2019 US dollars using the Consumer Price Index.(50) Future costs and QALYs were discounted by 3% annually. One-way sensitivity analyses were performed for all variables using ranges published in the literature. We also generated a secondary model evaluating single dosing of the LA-DAAS to test future versions of the device that we anticipate will be able to deliver a full course of HCV treatment.

Example 3

The following example relates to an algorithm for automatic detection of alcohol ingestion by doing linear regression analysis on the raw alcohol signal from a semiconductor gas sensor.

Figure 30:
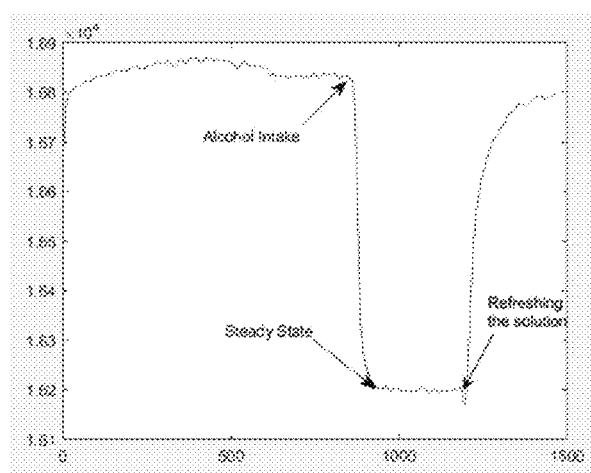
FIG. 30 shows a signature of ethanol detected by a volatile organic compound (VOC) gas sensor, according to one set of embodiments.

FIG. 30 shows a signature of ethanol detected by a volatile organic compound (VOC) gas sensor.

Figures 31A, 31B, 31C, 31D, 31E:
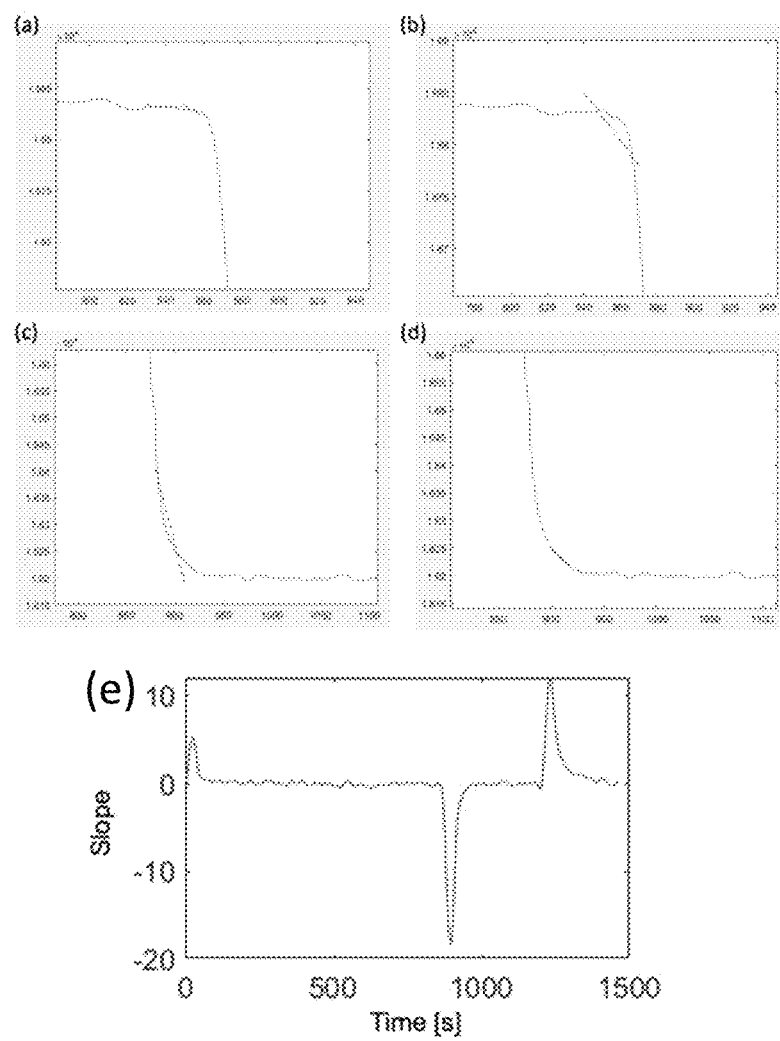
FIGS. 31A-31D shows a linear regression analysis of the ethanol detection using the VOC gas sensor, for captured raw data, according to one set of embodiments.
FIG. 31E shows a linear regression analysis of the raw ethanol signal, according to one set of embodiments.

FIGS. 31A-31D shows a linear regression analysis, indicated by the dotted line, of the ethanol detection using the VOC gas sensor, for captured raw data. FIG. 31A stand by; FIG. 31B alcohol ingestion detected; FIG. 31C wait; FIG. 31D steady state detected.

FIG. 31E shows a linear regression analysis of the raw ethanol signal. Negative slope values represent ethanol ingestion and positive slope values represent removal of ethanol.

Figures 32A, 32B:
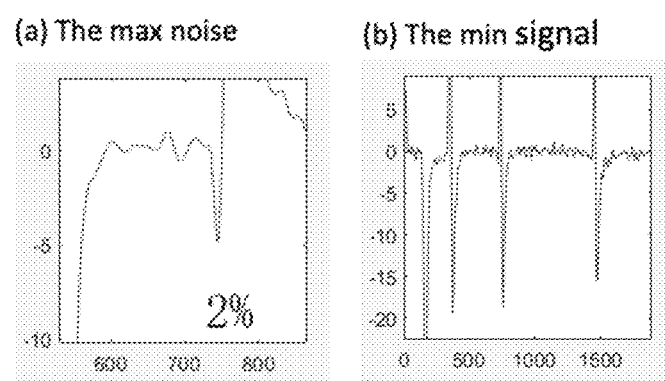
FIGS. 32A-32B shows, according to one set of embodiments.

Signal to noise ratio (SNR) may be defined as the ratio of the minimal signal to the maximum noise. FIGS. 32A-32B shows: FIG. 32A the maximum noise induced by a non-alcohol solution; FIG. 32B the minimum signal induced by an alcohol solution.

Alcohol solutions were tested, the solutions having an ethanol concentration ranging from 0 vol % to 50 vol %. The minimum signal and maximum noise were captured to characterize the signal to noise ratio. In the linear regression analysis, it was studied how the minimum signal, maximum noise, and the signal to noise ratio varied with varying the regression buffer length as shown in FIG. 33. As shown in FIG. 33, the signal to noise ratio increased as the regression buffer length increased.

Figure 34:
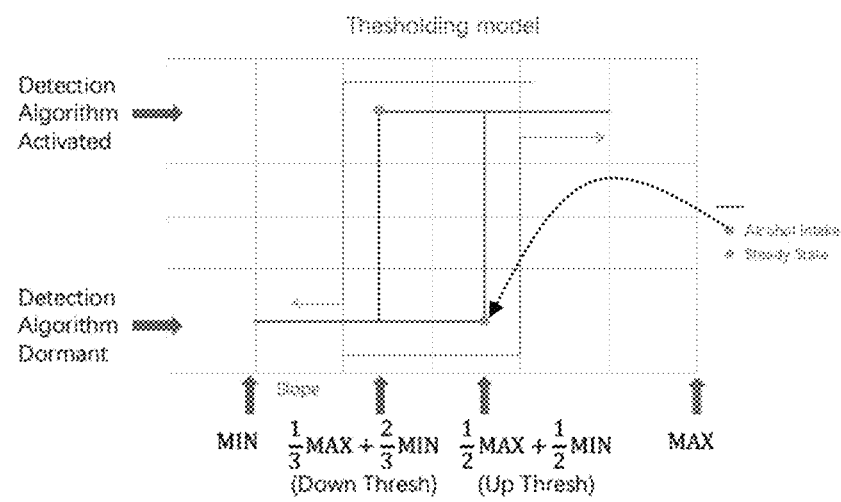
FIG. 34 shows a thresholding model: hysteresis comparator for automatic detection of alcohol ingestion, according to one set of embodiments.

FIG. 34 shows a thresholding model: hysteresis comparator for automatic detection of alcohol ingestion.

Figure 35:
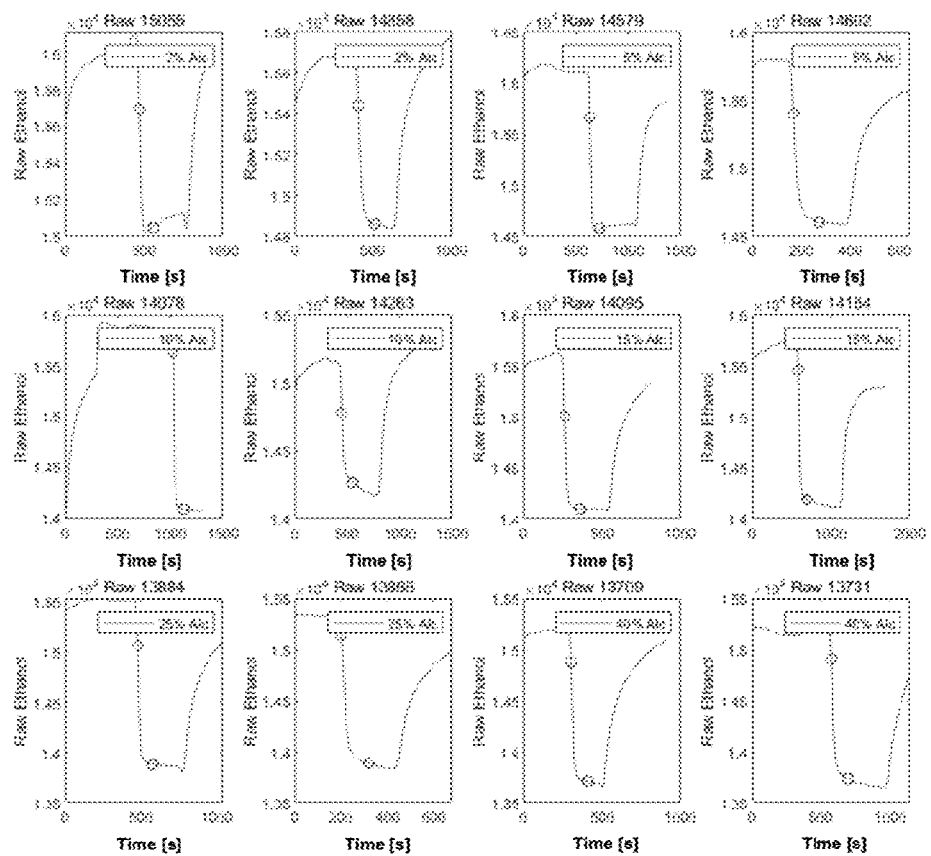
FIG. 35 shows automatic detection of alcohol consumption, according to one set of embodiments. The upper circle is activated by a down threshold and the lower circle is activated by an up threshold.

FIG. 35 shows automatic detection of alcohol consumption. The upper circle is activated by the down threshold (e.g., Down Thresh, FIG. 34) and the lower circle is activated by the up threshold (e.g., Up Thresh, FIG. 34).

Figure 36:
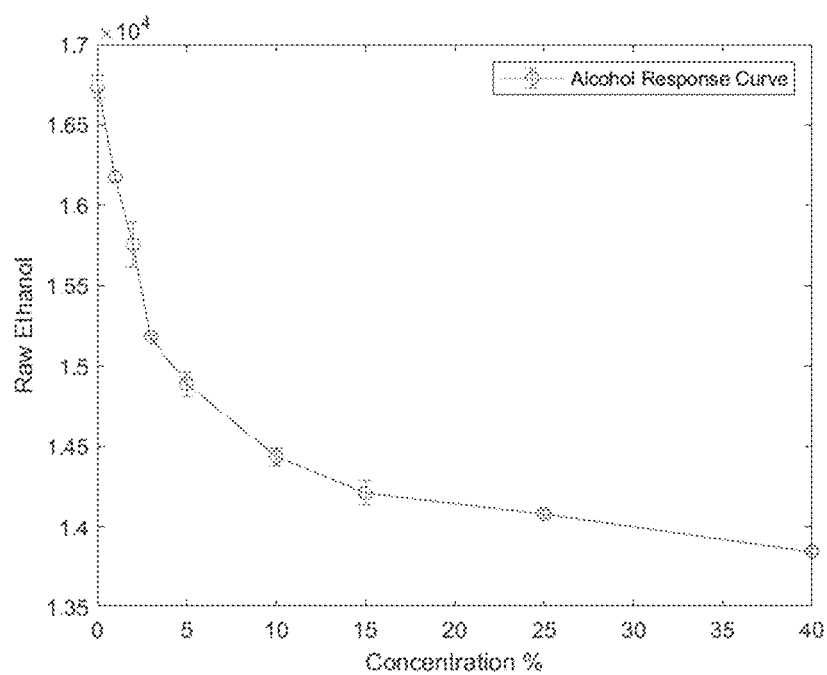
FIG. 36 shows raw ethanol signal versus ethanol solution concentration (weight percentage %) automatically captured by the down thresholding in FIG. 35, according to one set of embodiments.

FIG. 36 shows raw ethanol signal versus ethanol solution concentration (weight percentage %) automatically captured by the down thresholding in FIG. 35.

Figure 37:
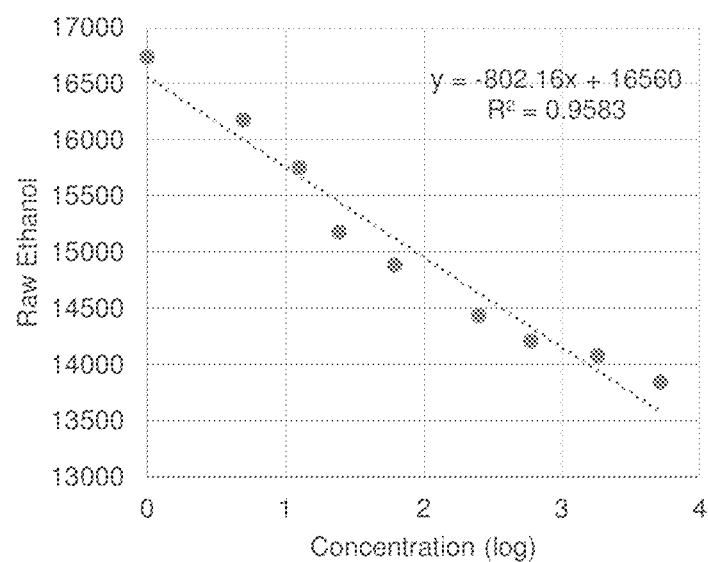
FIG. 37 shows raw ethanol signal versus the logarithm of the ethanol solution concentration of FIG. 36, according to one set of embodiments.

FIG. 37 shows raw ethanol signal versus the logarithm of the ethanol solution concentration of FIG. 36.

Figure 38:
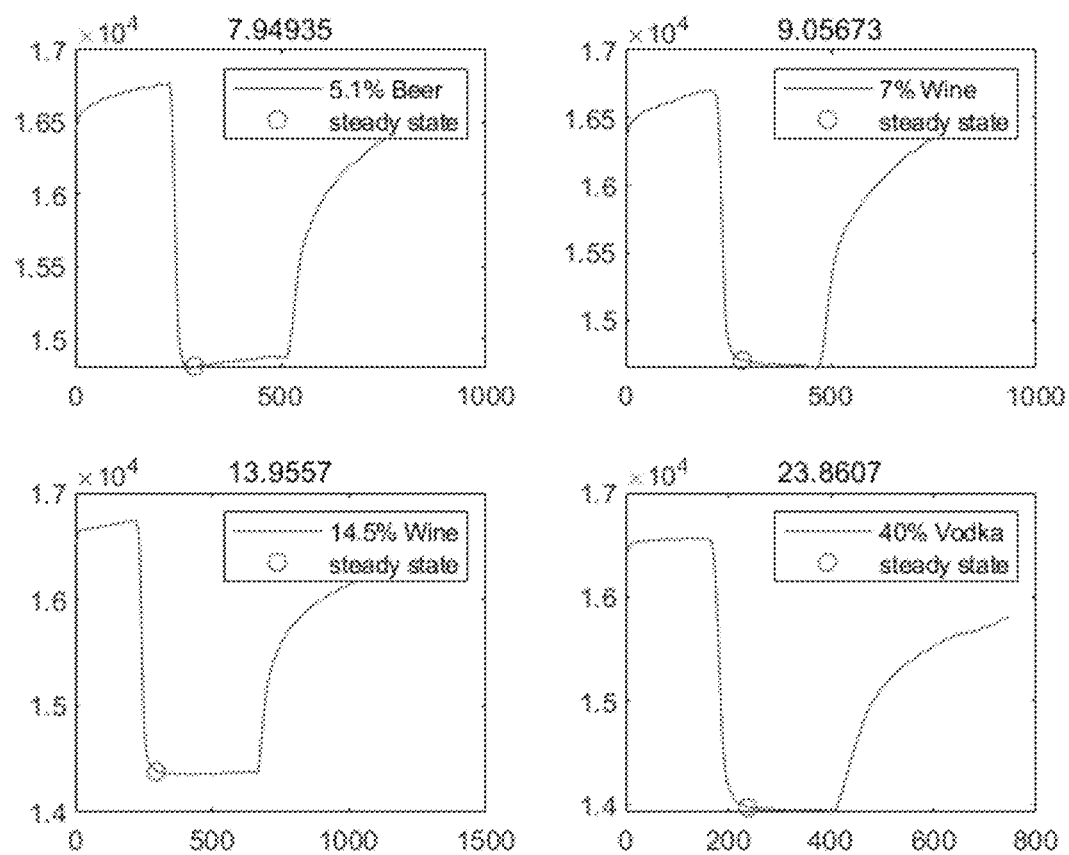
FIG. 38 shows automatic detection and estimation of ethanol concentration using the calibration curve from FIG. 37, according to one set of embodiments.

FIG. 38 shows automatic detection and estimation of ethanol concentration using the calibration curve from FIG. 37. The estimated ethanol concentrations of 5.1% beer, 7% wine, 14.5% wine, and 40% vodka are 7.94935%, 9.05673%, 13.9557%, and 23.8607%, respectively.

The estimation accuracy is particularly low when the ethanol concentration is too high or too low. This is due to the assumption of a linear alcohol-water vapor equilibrium curve. However, the real alcohol-water vapor equilibrium curve is highly non-linear as shown in FIG. 39.

Example 4

The following example relates to an algorithm for estimating ingested alcohol concentration using the alcohol-water vapor equilibrium curve.

Figure 39:
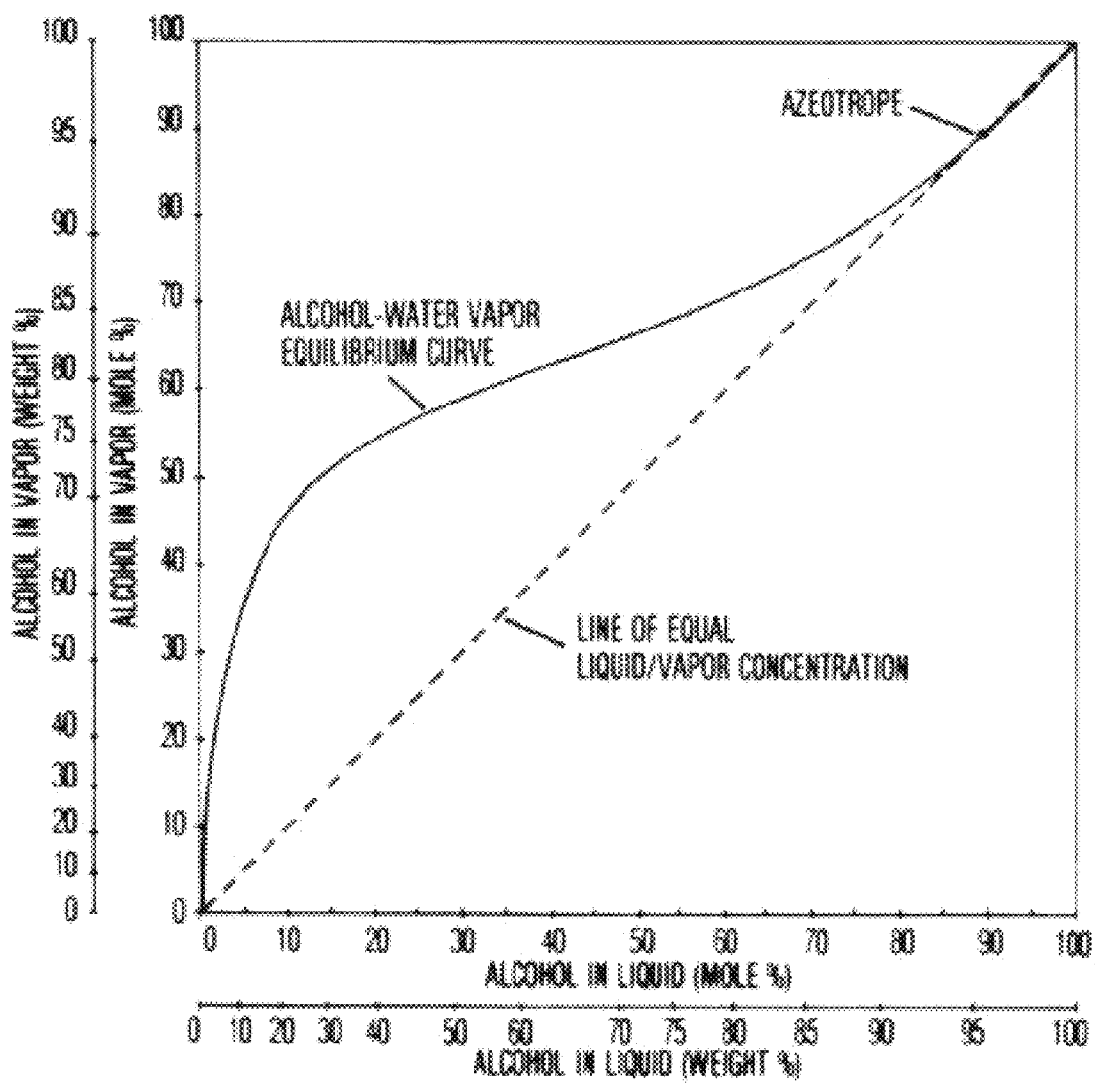
FIG. 39 shows an alcohol-water vapor equilibrium curve, according to one set of embodiments.

FIG. 39 shows an alcohol-water vapor equilibrium curve.

Figure 40:
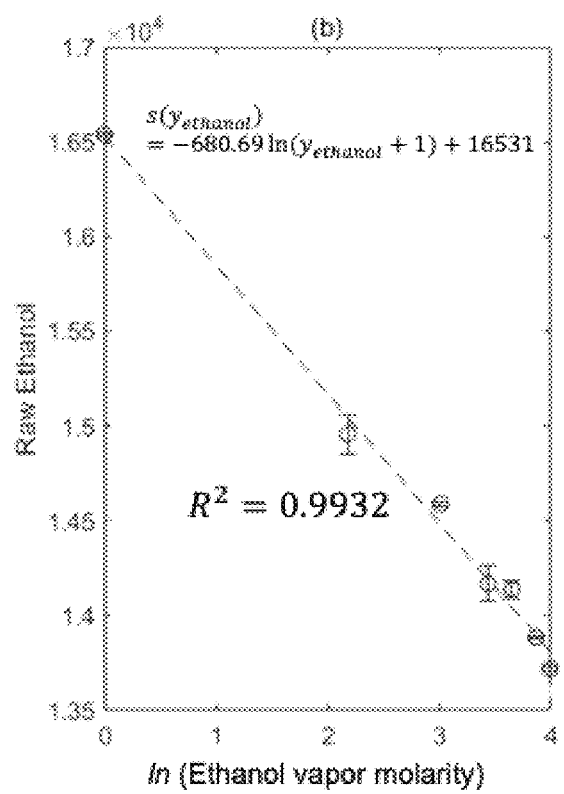
FIG. 40 shows raw ethanol signal versus the logarithm of the ethanol vapor concentration based on the correction of alcohol-water vapor equilibrium curve, according to one set of embodiments.

FIG. 40 shows raw ethanol signal versus the logarithm of the ethanol vapor concentration based on the correction of alcohol-water vapor equilibrium curve.

Figure 41:
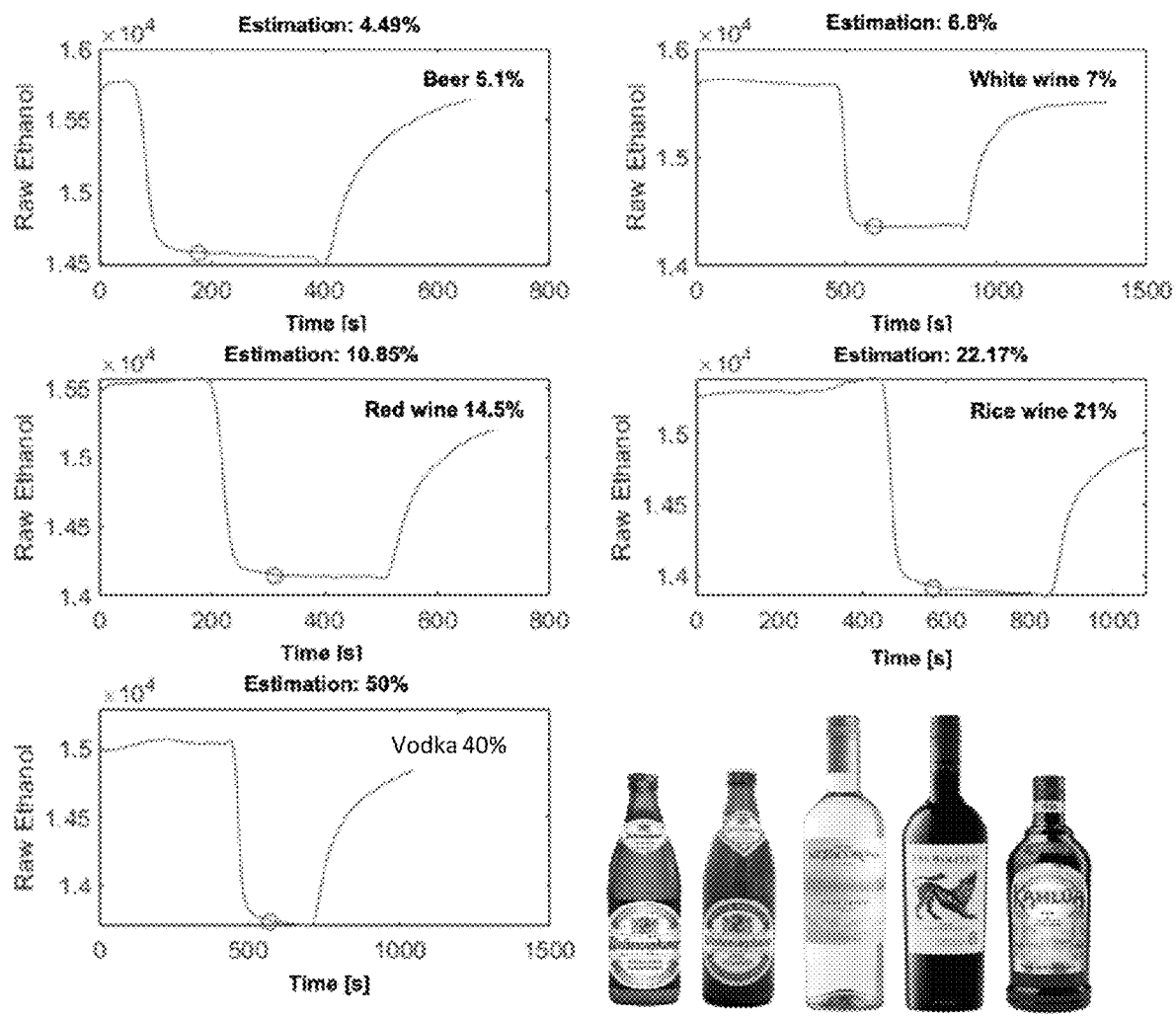
FIG. 41 shows automatic detection and estimation of alcohol ingestion consumption, according to one set of embodiments.

FIG. 41 shows automatic detection and estimation of alcohol ingestion consumption. The estimation of 5.1% beer, 7% white wine, 14.5% red wine, 21% rice wine, and 40% Vodka are 4.49%, 6.8%, 10.85%, 22.17%, and 50%, respectively, an improvement upon the results in FIG. 38 in Example 3.

The estimation accuracy could be further increased by improving the auto-capturing algorithm as the estimation value highly depends on the steady state raw ethanol signal.

Example 5

The following example relates to manufacturing procedures of gastric resident system capable of natural disassembly of ingestible electronics.

Figure 42:
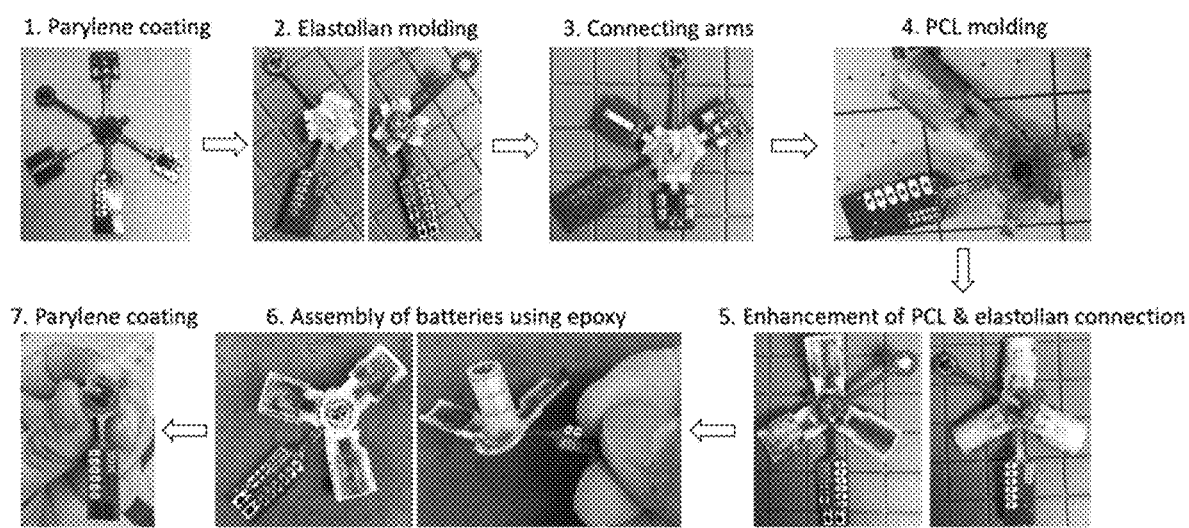
FIG. 42 shows an example of manufacturing procedures of gastric resident ingestible electronics, according to one set of embodiments.

FIG. 42 shows an example of manufacturing procedures of gastric resident ingestible electronics. This example device includes two different injection molding materials: Elastollan® molding and PCL molding. Elastollan® molding is applied on the core printed circuit board (PCB) to impart a resilient folding capability. PCL molding applied on the PCB arms to impart rigidity and biodegradability. The core PCB and arm PCBs are connected via a flexible printed circuit (FPC) connector, respectively.

In some embodiments, a manufacturing procedure includes, as shown in FIG. 42, coating the core PCB and arm PCBs with parylene, applying Elastollan® molding on the core PCB, connecting the core PCB and arm PCBs using a flexible FPC connector, applying PCL molding on the arm PCBs, enhancing the PCL and Elastollan® connection, assembling batteries using epoxy, and a parylene coating.

EXEMPLARY EMBODIMENTS

1. A gastroretentive sensor system comprising a sensor capable of monitoring alcohol intake wherein the sensor is integrated into a wirelessly communicating electric system and protected from gastrointestinal fluid by a gas permeable membrane.
2. Any of the previous embodiments in which gastric retention is achieved by device expansion, unfolding, folding, swelling or combinations thereof.
3. Any of the preceding embodiments in which the sensor is an electrochemical or semiconductor sensor.
4. Any of the preceding embodiments in which the gas permeable membrane comprises Polytetrafluoroethylene or silicone or combinations thereof.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/ tangential, etc.; direction—such as, north, south, east, west, etc.; surface and/or bulk material properties and/or spatial/ temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. A residence article, comprising:
   an alcohol sensor associated with a gastric residence article; and
   one or more drug delivery modules;
   wherein the gastric residence article is configured to be administered to a subject and to be retained at a location internal to the subject for at least 24 hours,
   wherein the residence article has a first configuration sized and adapted for transesophageal administration to a subject,
   wherein the residence article has a second configuration sized and adapted such that the residence article is retained in the stomach and prevented from passing through the pylorus, and
   wherein the alcohol sensor, upon detection of one or more biophysical conditions in the location internal the subject, is configured to trigger release of at least one therapeutic agent from the one or more drug delivery modules to the location internal the subject.

2. A residence article as in claim 1, wherein the residence article is configured to dissociate such that the alcohol sensor dissociates from the gastric residence article and may exit the subject.

3. A residence article as in claim 1, wherein the residence article is configured to be retrieved via the esophagus of the subject from the location internal the subject.

4. A residence article as in claim 1, further comprising a gas permeable membrane located with respect to the alcohol sensor such that the alcohol sensor is protected from gastrointestinal fluid when the residence article is administered to the subject.

5. A residence article as in claim 4, wherein the gas permeable membrane comprises polytetrafluoroethylene, silicone, or combinations thereof.

6. A residence article as in claim 1, comprising an electronic component comprising a wireless transmitter, wherein the wireless transmitter is configured to transmit a signal from the location internal to the subject to a receiver positioned extracorporeal of the subject.

7. A residence article as in claim 1, wherein the residence article comprises a degradable linker.

8. A residence article as in claim 1, wherein the location internal to the subject is the stomach.

9. A residence article as in claim 1, wherein the gastric retention device comprises a linker that degrades, dissolves, disassociates, or mechanically weakens in a gastric environment which results in loss of retention shape integrity of the gastric retention device and facilitates passage of the alcohol sensor and/or gastric retention device out of a gastric cavity.

10. A residence article as in claim 1, comprising polymeric arms configured to maintain structural integrity during the second configuration.

11. A residence article as in claim 1, wherein the gastric retention device comprises a polymeric material having a reconfigurable shape and a hollow core.

12. A residence article as in claim 1, wherein the residence article has a maximum dimension of greater than or equal to 28 cm.

13. A residence article as in claim 1, wherein the at least one therapeutic agent is present in the residence article in an amount greater than or equal to 1 gram.

14. A residence article as in claim 11, further comprising an elastic wire disposed within the hollow core.

15. A residence article as in claim 1, further comprising a magnetic component.

16. A residence article as in claim 14, wherein the elastic wire comprises a superelastic alloy and/or shape memory material.

17. A method, comprising administering, to the subject, a residence article as in claim 1.

18. A residence article as in claim 1, wherein the first configuration has a largest cross-sectional dimension that is between about 10% and 80% less than the largest cross-sectional dimension of the second configuration.

19. A residence article in claim 1, wherein the residence article has a third configuration in which a degradable portion of the gastric residence article dissolves, degrades, and/or mechanically weakens, such that the gastric residence article dissociates from the alcohol sensor, thereby allowing the alcohol sensor to exit the stomach via the pylorus.

* * * * *

UNITED STATES PATENT AND TRADEMARK OFFICE
CERTIFICATE OF CORRECTION

| | |
|---|---|
| PATENT NO. | : 11,850,034 B2 |
| APPLICATION NO. | : 17/318040 |
| DATED | : December 26, 2023 |
| INVENTOR(S) | : Robert S. Langer et al. |

It is certified that error appears in the above-identified patent and that said Letters Patent is hereby corrected as shown below:

In the Specification

Column 1, under the paragraph under the heading "RELATED APPLICATIONS", the below heading and paragraph should be added:
--GOVERNMENT SPONSORSHIP
This invention was made with government support under EB000244 awarded by the National Institutes of Health. The government has certain rights in the invention.--

Signed and Sealed this
Thirtieth Day of April, 2024

Katherine Kelly Vidal
*Director of the United States Patent and Trademark Office*